US 7,829,684 B2

(12) United States Patent
Ernst et al.

(10) Patent No.: US 7,829,684 B2
(45) Date of Patent: Nov. 9, 2010

(54) METHODS FOR PRODUCING SOLUBLE MEMBRANE-SPANNING PROTEINS

(75) Inventors: James A. Ernst, San Francisco, CA (US); Daniel Yansura, Pacifica, CA (US); Hok Seon Kim, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/541,828

(22) Filed: Aug. 14, 2009

(65) Prior Publication Data

US 2010/0081170 A1    Apr. 1, 2010

Related U.S. Application Data

(60) Division of application No. 12/489,343, filed on Jun. 22, 2009, which is a continuation of application No. 11/316,370, filed on Dec. 22, 2005, now Pat. No. 7,691,989.

(60) Provisional application No. 60/639,233, filed on Dec. 22, 2004.

(51) Int. Cl.
  *C12N 15/36* (2006.01)
  *C12N 15/70* (2006.01)
  *C12N 15/72* (2006.01)
  *C12N 15/09* (2006.01)
  *C12N 15/71* (2006.01)
  *A61K 38/00* (2006.01)

(52) U.S. Cl. ............... 536/23.1; 435/320.1; 435/476; 435/69.1; 435/490

(58) Field of Classification Search .................. None
  See application file for complete search history.

(56) References Cited

U.S. PATENT DOCUMENTS

| 4,738,921 | A  | 4/1988  | Belagaje et al. |
| 5,013,653 | A  | 5/1991  | Huston et al. |
| 6,242,177 | B1 | 6/2001  | Simmons et al. |
| 6,537,779 | B1 | 3/2003  | Kara et al. |
| 6,808,925 | B2 | 10/2004 | Calos |
| 7,247,426 | B2 | 7/2007  | Yakhini et al. |
| 7,691,989 | B2 | 4/2010  | Ernst et al. |
| 2003/0148457 | A1 | 8/2003 | Kinrade et al. |
| 2003/0228326 | A1 | 12/2003 | Palomba et al. |
| 2009/0258410 | A1 | 10/2009 | Ernst et al. |

FOREIGN PATENT DOCUMENTS

| EP | 0 300 425 | 1/1989 |
| EP | 0 303 925 | 2/1989 |
| JP | 03-123486 | 5/1991 |
| WO | WO-97/21829 | 6/1997 |
| WO | WO-99/53033 | 10/1999 |
| WO | WO-01/09189 | 2/2001 |
| WO | WO-01/14407 | 3/2001 |
| WO | WO-01/55178 | 8/2001 |
| WO | WO-01/74903 | 10/2001 |
| WO | WO-01/98453 | 12/2001 |
| WO | WO-2006/069403 A2 | 6/2006 |
| WO | WO-2006/069403 A3 | 6/2006 |

OTHER PUBLICATIONS

Bell et al., Nat Struct Biol 7(3):209-214.
Chevalet et al., Biotechnol Bioeng (2000) 69(4):351-358.
Database JPO Proteins [Online], EBI Accession No. JPOP:E50448, Jul. 1, 1997.
Dombrowicz et al., Immunity (1988) 8:517-529.
Donato et al., J. Clin. Invest. (2002) 109:51-58.
Ernst et al., Biochemistry (2005) 44(46):15150-15158.
Hashemzadeh-Bonehi et al., Mol Microbiol 30:673-678.
Hersh et al., PNAS USA 96(5):2396-2401.
Huez et al., Mol Cell Biol 18(11):6178-6190.
International Search Report for PCT/US2005/047653, mailed on Aug. 1, 2006, 9 pages.
Invitrogen (2008, updated) "pcDNA 3.1", Catalog Nos. V790-20 and V795-20, Invitrogen Life Technology, p. 9.
Invitrogen (2008, updated) Vector backbone: pCR3.1, <www.addgene.org/pgvec1?f=c&cmd=showvecinfo&vectorid=6620&pf=true, pp. 1-3>.
Ishibashi et al., Gene (2001) 264:87-93.
Kinet, Annu. Rev. Immunol. (1999) 17:931-972.
Liang et al., Genomics (2001) 72:119-127.
Lin et al., Cell (1996) 85:985-995.
Naider et al., Biopolymers 60(5):334-350.
Polyak et al., Journal of Immunology (1998) 161(7):3242-3248.
Ruberg et al., Microbiology 145(3):603-611.
Saxena et al., J Bacteriol 174(6):1956-1964.
Stashenko et al., J. Immunology (1980) 125:1678-1685.
Stenstrom et al., Gene (2002) 288:1-8.
Taylor et al., Proteomics (2003) 3(7);1303-1312.
Xie et al., Protein Expression and Purification (2004) 38:61-68.
Written Opinion of the International Searching Authority for PCT/US2005/047653, mailed on Aug. 1, 2006, 17 pages.
Glick, B.R. et al. (2002). *Molecular Biotechnology. Principles and Applications*, American Society of Microbiology, (Original document in Russian language, English Translation of pp. 365-367.).

(Continued)

*Primary Examiner*—Anand U Desai
*Assistant Examiner*—Samuel Liu
(74) *Attorney, Agent, or Firm*—Morrison & Foerster LLP

(57) ABSTRACT

Methods for producing membrane-spanning polypeptides in high yields, with native conformation, and/or in soluble form include solubilizing in non-ionic or zwitterionic detergents, as well as use of promoters and expression vectors for expressing high yields of membrane-spanning polypeptides in bacterial cells. Mutated promoters provide tight control of membrane-spanning polypeptides in bacterial cell hosts.

58 Claims, 28 Drawing Sheets

OTHER PUBLICATIONS

Guzman, L.-M. et al. (Jul. 1995). "Tight Regulation, Modulation, and High-Level Expression by Vectors Containing the Arabinose $P_{BAD}$ Promoter," *Journal of Bacteriology* 177(14):4121-4130.

Maniatis, T. et al. (1982). "Vectors That Express Cloned DNA in *Escherichia coli*," Chapter 12 *in Molecular Cloning: A Laboratory Manual*, Cold Spring Harbor Laboratory: New York, NY, pp. 403-433 (with Table of Contents.).

Maniatis, T. et al. (1984). *Molecular Cloning: A Laboratory Manual*, Cold Spring Harbor Laboratory: New York, NY, (Original document in Russian language, p. 360, 361, 364, 383, 385, corresponds with Chapter 12 above.).

Patrushev, L.I. (2004). *Iskusstvennye Geneticheskie Sistemy (Artificial Genetic Systems)*, Moscow, Nauka, (Original document in Russian language, English Translation of 1:108, 111-112.).

Rybchin, V.N. (2002). "Osnovy Geneticheskoi Indgenerii" (Foundations of Genetic Engineering), St. Petersburg, SPbGTU Publ. (Original document in Russian language pp. 317, 329, 339; English Translation two pages.).

Expression of MS4A Class Proteins in *E. coli*

Time Course of RA1C Expression from phoA pEfRA1C

Figure 13  Leakage from Non-induced Promoters – GPR73 Expression

Time Course of GPR73 Expression from *phac* promoter

Leakage from Non-induced Promoter – MS4A4A Expression

Figure 19  MS4A4A Expression from *tphac* promoter pMS4A4ArT phoA vs. tphac Expression of MS4A4A

Figure 22 trpLE leaders

LE LEADER (9 kDa)

```
            - + -  - + -   + + +  + -              -       - + -      - +          +   - +       + -  + +
MKAIFVLKGS  LDRDLDSRIE  LEMRTKHKEL  SEHLMLVDLA  RNDLARICTP  GSRYVADLTK  VDRYSYVMHL  VSRVVGELR
9AA trp leader                                   AA 339-408 trp E polypeptide (69AA)
``` sLE LEADER (5 kDa)

```
            - + -  - + +       -
MKAIFVLKGS  LDRDLARIIV  IRSALVENGI  ATVQAGAGVV  LDSGAAHY         5 kDa
9AA trp leader          discontinous AA trp E polypeptide (38AA)
```

Membrane Protein Extraction of LE.GPR73

1. pBR322 (- CTRL)
2. Microfluidized Total Lysate
3. Sup 1
4. Pellet 1
5. Sup 2
6. Pellet 2

1% FC (brackets lines 4–6)

SEQUENCE LISTING

```
<160> NUMBER OF SEQ ID NOS: 36

<210> SEQ ID NO 1
<211> LENGTH: 297
<212> TYPE: PRT
<213> ORGANISM: Homo sapiens

<400> SEQUENCE: 1

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205
```

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 2
<211> LENGTH: 1473
<212> TYPE: DNA
<213> ORGANISM: Homo sapiens

<400> SEQUENCE: 2
agtgtgcttg agaaacaaac tgcacccact gaactccgca gctagcatcc aaatcagccc       60
ttgagatttg aggccttgga gactcaggag ttttgagagc aaaatgacaa cacccagaaa      120
ttcagtaaat gggactttcc cggcagagcc aatgaaaggc cctattgcta tgcaatctgg      180
tccaaaacca ctcttcagga ggatgtcttc actggtgggc ccacgcaaa gcttcttcat       240
gagggaatct aagactttgg ggctgtcca gattatgaat gggctcttcc acattgccct       300
gggggggtctt ctgatgatcc cagcagggat ctatgcaccc atctgtgtga ctgtgtggta      360
ccctctctgg ggaggcatta tgtatattat ttccggatca ctcctggcag caacggagaa      420
aaactccagg aagtgtttgg tcaaggaaa atgataatg aattcattga gcctctttgc         480
tgccatttct ggaatgattc tttcaatcat ggacatactt aatattaaaa tttcccattt      540
tttaaaaatg gagagtctga attttattag agctcacaca ccatatatta acatatacaa      600
ctgtgaacca gctaatccct ctgagaaaaa ctccccatct acccaatact gttacagcat      660
acaatctctg ttcttgggca ttttgtcagt gatgctgatc tttgccttct tccaggaact      720
tgtaatagct ggcatcgttg agaatgaatg gaaaagaacg tgctccagac ccaaatctaa      780
catagttctc ctgtcagcag aagaaaaaaa agaacagact attgaaataa agaagaagt       840
ggttgggcta actgaaacat cttcccaacc aaagaatgaa gagacattg aaattattcc        900
aatccaagaa gaggaagaag aagaaacaga gacgaacttt ccagaacctc ccaagatca       960
ggaatcctca ccaatagaaa atgacagctc tccttaagtg atttcttctg ttttctgttt     1020
cctttttaa acattagtgt tcatagcttc caagagacat gctgactttc atttcttgag      1080
gtactctgca catacgcacc acatctctat ctggcctttg catggagtga ccatagctcc     1140
ttctctctta cattgaatgt agagaatgta gccattgtag cagcttgtgt tgtcacgctt     1200
cttcttttga gcaactttct tacactgaag aaaggcagaa tgagtgcttc agaatgtgat     1260
ttcctactaa cctgttcctt ggataggctt tttagtatag tattttttttt ttgtcatttt    1320
ctccatcagc aaccagggag actgcacctg atggaaaaga tatatgactg cttcatgaca    1380
ttcctaaact atcttttttt tattccacat ttacgttttt ggtggagtcc cttttgcatc    1440
attgttttaa ggatgataaa aaaaaaaaa aaa                                    1473

<210> SEQ ID NO 3

<211> LENGTH: 291
<212> TYPE: PRT
<213> ORGANISM: Mus musculus

<400> SEQUENCE: 3

```
Met Ser Gly Pro Phe Pro Ala Glu Pro Thr Lys Gly Pro Leu Ala Met
1               5                   10                  15

Gln Pro Ala Pro Lys Val Asn Leu Lys Arg Thr Ser Ser Leu Val Gly
            20                  25                  30

Pro Thr Gln Ser Phe Phe Met Arg Glu Ser Lys Ala Leu Gly Ala Val
        35                  40                  45

Gln Ile Met Asn Gly Leu Phe His Ile Thr Leu Gly Gly Leu Leu Met
    50                  55                  60

Ile Pro Thr Gly Val Phe Ala Pro Ile Cys Leu Ser Val Trp Tyr Pro
65                  70                  75                  80

Leu Trp Gly Gly Ile Met Tyr Ile Ile Ser Gly Ser Leu Leu Ala Ala
                85                  90                  95

Ala Ala Glu Lys Thr Ser Arg Lys Ser Leu Val Lys Ala Lys Val Ile
            100                 105                 110

Met Ser Ser Leu Ser Leu Phe Ala Ala Ile Ser Gly Ile Ile Leu Ser
        115                 120                 125

Ile Met Asp Ile Leu Asn Met Thr Leu Ser His Phe Leu Lys Met Arg
    130                 135                 140

Arg Leu Glu Leu Ile Gln Thr Ser Lys Pro Tyr Val Asp Ile Tyr Asp
145                 150                 155                 160

Cys Glu Pro Ser Asn Ser Ser Glu Lys Asn Ser Pro Ser Thr Gln Tyr
                165                 170                 175

Cys Asn Ser Ile Gln Ser Val Phe Leu Gly Ile Leu Ser Ala Met Leu
            180                 185                 190

Ile Ser Ala Phe Phe Gln Lys Leu Val Thr Ala Gly Ile Val Glu Asn
        195                 200                 205

Glu Trp Lys Arg Met Cys Thr Arg Ser Lys Ser Asn Val Val Leu Leu
    210                 215                 220

Ser Ala Gly Glu Lys Asn Glu Gln Thr Ile Lys Met Lys Glu Glu Ile
225                 230                 235                 240

Ile Glu Leu Ser Gly Val Ser Ser Gln Pro Lys Asn Glu Glu Glu Ile
                245                 250                 255

Glu Ile Ile Pro Val Gln Glu Glu Glu Glu Ala Glu Ile Asn
            260                 265                 270

Phe Pro Ala Pro Pro Gln Glu Gln Glu Ser Leu Pro Val Glu Asn Glu
        275                 280                 285

Ile Ala Pro
    290
```

<210> SEQ ID NO 4
<211> LENGTH: 2838
<212> TYPE: DNA
<213> ORGANISM: Mus musculus

<400> SEQUENCE: 4

```
actcatcttc aagtacttga gatagaagag gccagctgat ctcagctgtg agtggctaat      60
ttggccctta agccttggag ccttggagcc ttggagaccc aggcgtttga aaactcaatg     120
agtggacctt tcccagcaga gcctacaaaa ggtcccctcg ccatgcaacc tgctccaaaa     180
gtgaacctca aaggacatc ttcactggtg ggccccacac aaagcttctt catgagggaa     240
```

```
tcaaaggctt tgggggctgt ccaaatcatg aatggcctct tccatattac cctgggggga      300
ctgctgatga tccccacagg ggtcttcgca cccatctgtt tgagtgtatg gtaccctctc      360
tggggaggca ttatgtacat tatttcagga tcactcctgg cagctgcagc agaaaaaacc      420
tccaggaaga gtttggtcaa agcaaaagtg ataatgagct ctctaagcct ctttgctgcc      480
atttctggaa taattctttc aatcatggac atacttaaca tgacactttc tcattttta       540 aaaatgagaa gactggagct tattcaaact tccaagccgt atgttgatat ctacgactgt      600
gaaccatcta attcctcaga gaaaaactcc ccatctacac agtactgtaa cagcattcag      660
tctgtgttct tgggcattct gtcggcgatg ctgatctctg ccttcttcca gaaacttgtg      720
acagctggta ttgtggagaa tgagtggaaa agaatgtgta ccagatccaa atctaatgtg      780
gttctgctgt cagctggaga aaaaaatgag cagacgatta aaatgaaaga gaaatcatt       840 gagctaagtg gagtatcttc ccaaccaaag aatgaagagg aaattgaaat tattccagtg      900
caggaggaag aagaagaaga agcagaaata aatttttccag cacctcccca agagcaggaa    960
tccttgccag tggaaaatga gatcgctcct taaactcttt tcttttctaa gcattattgt     1020
ttagagagct tccaagacac atagttaccc tcatctcttg tggccttcca caatctattc     1080
tccatatttt cacagcttaa ctttgcatag agaagccaca tctagctctc cttcacattt     1140
gaagaatgca gtgattataa aagattgtct tttgccttgc ttagggagtc ttacactggc     1200
agaaacgctg aagaatccaa ttctcattca ccttttcctt ggatgtgtgt ctcagtagtg     1260
gtaatggttt ttccgcattt cctccatcag cagttacagc agagggaaaa gacacatgac     1320
tgttctgttc atctctgaac tctctgactc cttcttcatg tttggtggag tccctttttgc    1380 atgattgtct taaagaatat gagagaaatt gtttaatgag aattgttta ataatgagag     1440 aaaatgagac acctatatgc ctgtggggaa ggcacaaaat atggcatgtt cttcaagctt     1500
ctgtgtccca cttgggaagc tgtgaaaggc ctagtcctaa gtctgtctct gtacaaaaag     1560
catagcttac acataagcaa gtttcatgtc ttaactttgc ccatctccag tttcttggct     1620
tctggtcaca tcgtttatgt atttgtattc tttagtcaag agaaaaaaga atggtgagac     1680
agaaatgtaa tgggttccca gatctcaaat cctaagcaac agctgtgctt tgagattctt     1740
tccaaatggc agagtagttt atttggtctt tcatgattca cagaaaaaaa acaaaaaaac     1800
aaaaaacaaa aaacctatca ctattttgta atttagttga atgtaagaag caagccaaga     1860
tattcaataa tagttgtggg gacttgagtc aaacccagct cttcaaattc tagaaatgtt     1920
tgaaataacc aaattatcta tgcccatatg cctgtataag ctatatcaaa gtatatactt     1980
tgtgagcaat gtgctgaatc acaaaagagt cagaattgga tttgacacca tatgaataaa    2040
gacacccaga atcttacatc atttggaaaa ctagtcgtga cattaatatg caattagctg    2100
gaaagttata agatgcacca caaacacatc ttatatgcac tataaattac cacacaaaga    2160
tcatgcttaa aaacaacaca gttaaaatcc taaatctcag gccaccatac tttcccaccc    2220
ctgttcctga gcagggatgc tagcacctga cctagaaaca ctgttagcct aaaaagatct    2280
caccatagcc tatcattcag ataccatgac aagtctgctt ctaggcatta tgggtatatg    2340
aacagcttaa gtttcactcc ttggaatatt tctattttat tagaggctac cggtgggagt    2400
tatttcctgt tattacaaag aaactggaag tagcaccttt tccctgtgtg gtcttcaaaa    2460
caagctctaa gtaaataaaa ctttgtgtca gtgcctgcaa tggatactcc accttggatg    2520
tttctttctt ctccataaca tcaaacaatg ggatgcttct gccacataat actaacctgt    2580
gtttgaatag tggcacatcc agtcatattg agctattcct acctatctga cacatgctcc    2640
```

```
caaggagttt actcatccag taggtcttta ctaagttctg cccacttaca agccacagca    2700
cgattctcca tatccattct tctccataga aggtaccta agctaaagaa gataccgcta     2760
tgcctggaga ggatggggag gtgggaggag gagtgtcaag ctgaaaagtt ttaaatgcag    2820
tattcaattt gaaaagtt                                                  2838
```

<210> SEQ ID NO 5
<211> LENGTH: 168
<212> TYPE: DNA
<213> ORGANISM: Artificial Sequence
<220> FEATURE:
<223> OTHER INFORMATION: Synthetic construct
<220> FEATURE:
<223> OTHER INFORMATION: phoA

<400> SEQUENCE: 5

```
gcgattacgt aaagaagtta ttgaagcatc ctcgtcagta aaaagttaat cttttcaaca     60
gctgtcataa agttgtcacg gccgagactt atagtcgctt tgtttttatt ttttaatgta    120
tttgtaacta gtacgcaagt tcacgtaaaa agggtatcta gaattatg                 168
```

<210> SEQ ID NO 6
<211> LENGTH: 297
<212> TYPE: PRT
<213> ORGANISM: Artificial Sequence
<220> FEATURE:
<223> OTHER INFORMATION: Synthetic construct
<220> FEATURE:
<223> OTHER INFORMATION: C2S mutant

<400> SEQUENCE: 6

```
Met Thr Thr Pro Arg Asn Ser Val Asn Gly Thr Phe Pro Ala Glu Pro
 1               5                  10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Ser Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Ser Ser Arg Pro Lys
```

```
            210                 215                 220
Ser Asn Ile Val Leu Leu Ser Ala Glu Glu Lys Glu Gln Thr Ile
225                 230                 235                 240

Glu Ile Lys Glu Glu Val Val Gly Leu Thr Glu Thr Ser Ser Gln Pro
            245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
        290                 295

<210> SEQ ID NO 7
<211> LENGTH: 7
<212> TYPE: PRT
<213> ORGANISM: Artificial Sequence
<220> FEATURE:
<223> OTHER INFORMATION: Synthetic construct
<220> FEATURE:
<223> OTHER INFORMATION: Translation initiator

<400> SEQUENCE: 7

Met Lys His Gln His Gln Gln
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic construct
<220> FEATURE:
<223> OTHER INFORMATION: Octa-His

<400> SEQUENCE: 8

His His His His His His His His
1               5

<210> SEQ ID NO 9
<211> LENGTH: 1550
<212> TYPE: DNA
<213> ORGANISM: Homo sapiens

<400> SEQUENCE: 9
agagccctgc atgcatcaga cctacagcag acattgcagg cctgaagaaa gcaccttttc      60
tgctgccatg acaaccatgc aaggaatgga acaggccatg ccaggggctg ccctggtgt     120 gccccagctg ggaaacatgg ctgtcataca ttcacatctg tggaaaggat gcaagagaa     180 gttcttgaag ggagaaccca agtccttggg ggttgtgcag attctgactg ccctgatgag    240
ccttagcatg gaataacaa tgatgtgtat ggcatctaat acttatggaa gtaaccctat     300
ttccgtgtat atcgggtaca caatttgggg gtcagtaatg tttattattt caggatcctt    360
gtcaattgca gcaggaatta gaactacaaa aggcctggtc cgaggtagtc taggaatgaa    420
tatcaccagc tctgtactgg ctgcatcagg atcttaatc aacacattta gcttggcgtt     480
ttattcattc catcacccctt actgtaacta ctatggcaac tcaaataatt gtcatgggac   540
tatgtccatc ttaatgggtc tggatggcat ggtgctcctc ttaagtgtgc tggaattctg    600
cattgctgtg tccctctctg cctttggatg taaagtgctc tgtttgtaccc ctggtggggt   660 tgtgttaatt ctgccatcac attctcacat ggcagaaaca gcatctccca caccacttaa    720
```

```
tgaggtttga ggccaccaaa agatcaacag acaaatgctc cagaaatcta tgctgactgt    780
gacacaagag cctcacatga gaaattacca gtatccaact tcgatactga tagacttgtt    840
gatattatta ttatatgtaa tccaattatg aactgtgtgt gtatagagag ataataaatt    900
caaaattatg ttctcatttt tttccctgga actcaataac tcatttcact ggctctttat    960
cgagagtact agaagttaaa ttaataaata atgcatttaa tgaggcaaca gcacttgaaa   1020
gtttttcatt catcataaga actttatata aaggcattac attggcaaat aaggtttgga   1080
agcagaagag caaaaaaaag atattgttaa aatgaggcct ccatgcaaaa cacatacttc   1140
cctcccattt atttaacttt ttttttctcc tacctatggg gaccaaagtg ctttttcctt   1200
caggaagtgg agatgcatgg ccatctcccc ctcccttttt ccttctcctg cttttctttc   1260
cccatagaaa gtaccttgaa gtagcacagt ccgtccttgc atgtgcacga gctatcattt   1320
gagtaaaagt atacatggag taaaaatcat attaagcatc agattcaact tatattttct   1380
atttcatctt cttcctttcc cttctcccac cttctactgg gcataattat atcttaatca   1440
tatatggaaa tgtgcaacat atggtatttg ttaaatacgt ttgttttat  tgcagagcaa    1500
aaataaatca aattagaacc aaaaaaaaaa aaaaaaaaa  aaaaaaaaaa              1550
```

<210> SEQ ID NO 10
<211> LENGTH: 239
<212> TYPE: PRT
<213> ORGANISM: Homo sapiens

<400> SEQUENCE: 10

```
Met His Gln Thr Tyr Ser Arg His Cys Arg Pro Glu Glu Ser Thr Phe
1               5                   10                  15

Ser Ala Ala Met Thr Thr Met Gln Gly Met Glu Gln Ala Met Pro Gly
            20                  25                  30

Ala Gly Pro Gly Val Pro Gln Leu Gly Asn Met Ala Val Ile His Ser
        35                  40                  45

His Leu Trp Lys Gly Leu Gln Glu Lys Phe Leu Lys Gly Glu Pro Lys
    50                  55                  60

Val Leu Gly Val Val Gln Ile Leu Thr Ala Leu Met Ser Leu Ser Met
65                  70                  75                  80

Gly Ile Thr Met Met Cys Met Ala Ser Asn Thr Tyr Gly Ser Asn Pro
                85                  90                  95

Ile Ser Val Tyr Ile Gly Tyr Thr Ile Trp Gly Ser Val Met Phe Ile
            100                 105                 110

Ile Ser Gly Ser Leu Ser Ile Ala Ala Gly Ile Arg Thr Thr Lys Gly
        115                 120                 125

Leu Val Arg Gly Ser Leu Gly Met Asn Ile Thr Ser Ser Val Leu Ala
    130                 135                 140

Ala Ser Gly Ile Leu Ile Asn Thr Phe Ser Leu Ala Phe Tyr Ser Phe
145                 150                 155                 160

His His Pro Tyr Cys Asn Tyr Tyr Gly Asn Ser Asn Cys His Gly
                165                 170                 175

Thr Met Ser Ile Leu Met Gly Leu Asp Gly Met Val Leu Leu Leu Ser
            180                 185                 190

Val Leu Glu Phe Cys Ile Ala Val Ser Leu Ser Ala Phe Gly Cys Lys
        195                 200                 205

Val Leu Cys Cys Thr Pro Gly Gly Val Val Leu Ile Leu Pro Ser His
    210                 215                 220

Ser His Met Ala Glu Thr Ala Ser Pro Thr Pro Leu Asn Glu Val
```

```
                        225                 230                 235

<210> SEQ ID NO 11
<211> LENGTH: 1152
<212> TYPE: DNA
<213> ORGANISM: Homo sapiens
<220> FEATURE:
<221> NAME/KEY: misc_feature
<222> LOCATION: (29)..(29)
<223> OTHER INFORMATION: n is a, c, g, or t

<400> SEQUENCE: 11
ttttactgac cttgctagaa gtttacagnc acggaagtgc aggaacattt cacaaatcta      60
caatctgtga gtatcacatc ctgtatagct gtaaacactg gaataaggaa gggctgatga     120 cttcagaag atgaaggtaa gtagaaaccg ttgatgggac tgagaaacca gagttaaaac      180
ctctttggag cttctgagga ctcagctgga accaacgggc acagttggca acaccatcat     240
gacatcacaa cctgttccca atgagaccat catagtgctc ccatcaaatg tcatcaactt     300
ctcccaagca gagaaacccg aacccaccaa ccaggggcag gatagcctga gaaacatct     360 acacgcagaa attaaagtta ttgggactat ccagatcttg tgtggcatga tggtattgag     420
cttggggatc attttggcat ctgcttcctt ctctccaaat tttacccaag tgacttctac     480
actgttgaac tctgcttacc cattcatagg accctttttt tttatcatct ctggctctct     540
atcaatcgcc acagagaaaa ggttaaccaa gcttttggtg catagcagcc tggttggaag     600
cattctgagt gctctgtctg ccctggtggg tttcattatc ctgtctgtca acaggccac      660 cttaaatcct gcctcactgc agtgtgagtt ggacaaaaat aatataccaa caagaagtta     720
tgtttcttac ttttatcatg attcacttta taccacggac tgctatacag ccaaagccag     780
tctggctgga actctctctc tgatgctgat ttgcactctg ctggaattct gcctagctgt     840
gctcactgct gtgctgcggt ggaaacaggc ttactctgac ttccctggga gtgtactttt     900
cctgcctcac agttacattg gtaattctgg catgtcctca aaaatgactc atgactgtgg     960
atatgaagaa ctattgactt cttaagaaaa aagggagaaa tattaatcag aaagttgatt    1020
cttatgataa tatggaaaag ttaaccatta tagaaaagca aagcttgagt ttcctaaatg    1080
taagctttta aagtaatgaa cattaaaaaa aaccattatt tcactgtcaa aaaaaaaaa    1140 aaaaaaaaaa aa                                                       1152

<210> SEQ ID NO 12
<211> LENGTH: 248
<212> TYPE: PRT
<213> ORGANISM: Homo sapiens

<400> SEQUENCE: 12

Met Thr Ser Gln Pro Val Pro Asn Glu Thr Ile Ile Val Leu Pro Ser
1               5                   10                  15

Asn Val Ile Asn Phe Ser Gln Ala Glu Lys Pro Glu Pro Thr Asn Gln
            20                  25                  30

Gly Gln Asp Ser Leu Lys Lys His Leu His Ala Glu Ile Lys Val Ile
        35                  40                  45

Gly Thr Ile Gln Ile Leu Cys Gly Met Met Val Leu Ser Leu Gly Ile
    50                  55                  60

Ile Leu Ala Ser Ala Ser Phe Ser Pro Asn Phe Thr Gln Val Thr Ser
65                  70                  75                  80

Thr Leu Leu Asn Ser Ala Tyr Pro Phe Ile Gly Pro Phe Phe Phe Ile
                85                  90                  95
```

```
Ile Ser Gly Ser Leu Ser Ile Ala Thr Glu Lys Arg Leu Thr Lys Leu
            100                 105                 110
Leu Val His Ser Ser Leu Val Gly Ser Ile Leu Ser Ala Leu Ser Ala
        115                 120                 125
Leu Val Gly Phe Ile Ile Leu Ser Val Lys Gln Ala Thr Leu Asn Pro
    130                 135                 140
Ala Ser Leu Gln Cys Glu Leu Asp Lys Asn Asn Ile Pro Thr Arg Ser
145                 150                 155                 160
Tyr Val Ser Tyr Phe Tyr His Asp Ser Leu Tyr Thr Thr Asp Cys Tyr
                165                 170                 175
Thr Ala Lys Ala Ser Leu Ala Gly Thr Leu Ser Leu Met Leu Ile Cys
            180                 185                 190
Thr Leu Leu Glu Phe Cys Leu Ala Val Leu Thr Ala Val Leu Arg Trp
        195                 200                 205
Lys Gln Ala Tyr Ser Asp Phe Pro Gly Ser Val Leu Phe Leu Pro His
    210                 215                 220
Ser Tyr Ile Gly Asn Ser Gly Met Ser Ser Lys Met Thr His Asp Cys
225                 230                 235                 240
Gly Tyr Glu Glu Leu Leu Thr Ser
                245

<210> SEQ ID NO 13
<211> LENGTH: 1228
<212> TYPE: DNA
<213> ORGANISM: Homo sapiens

<400> SEQUENCE: 13
agattgttct ggcaaggaac agccagtggg aggttccagc tgagcgctcc ccagaggtga      60
gctgatcccc agccacagca cacaggacca ggctgcgaga acagcatcat cagcatcatg     120
ctattacaat cccaaaccat gggggtttct cacagcttta caccaaaggg catcactatc     180
cctcaaagag agaaacctgg acacatgtac caaaacgaag attacctgca gaacgggctg     240
ccaacagaaa ccaccgttct ggggactgtc agatcctgtg ttgcctgttg atttcaagt     300
ctgggggcca tcttggtttt tgctccctac ccctcccact tcaatccagc aatttccacc     360
actttgatgt ctgggtaccc attttttagga gctctgtgtt ttggcattac tggatccctc     420
tcaattatct ctggaaaaca atcaactaag cccttttgacc tgagcagctt gacctcaaat     480
gcagtgagtt ctgttactgc aggagcaggc ctcttcctcc ttgctgacag catggtagcc     540
ctgaggactg cctctcaaca ttgtggctca gaaatggatt atctatcctc attgccttat     600
tcggagtact attatccaat atatgaaatc aaagattgtc tcctgaccag tgtcagttta     660
acaggtgtcc tagtggtgat gctcatcttc actgtgctgg agctcttatt agctgcatac     720
agttctgtct tttggtggaa acagctctac tccaacaacc tgggagttc attttcctcg     780
acccagtcac aagatcatat ccaacaggtc aaaaagagtt cttcacggtc ttggatataa     840
gtaactcttg gcctcagagg aaggaaaagc aactcaacac tcatggtcaa gtgtgattag     900
actttcctga aatctctgcc attttagata ctgtgaaaca aactaaaaaa aaaaaagctt     960
ttgttttgta tttgttttact atgagtcgtt atttaatttc tcttgaaaat aatttcctca    1020
aagcccaagt caataaatgt tatcagccag tcttccaaaa tggtcataaa ctttataaac    1080
tgctttgggt aaactgagca gaaggtgata cacagaaggg aaaatgtgca ctcatgctag    1140
tgtgaatttg gtaagtcgcg tgactctgca ggctgttcct gtattatttt cacactcata    1200
```
ttgcttaaat attacatatt agggattg 1228

<210> SEQ ID NO 14
<211> LENGTH: 240
<212> TYPE: PRT
<213> ORGANISM: Homo sapiens

<400> SEQUENCE: 14

Met Leu Leu Gln Ser Gln Thr Met Gly Val Ser His Ser Phe Thr Pro
1               5                   10                  15

Lys Gly Ile Thr Ile Pro Gln Arg Glu Lys Pro Gly His Met Tyr Gln
            20                  25                  30

Asn Glu Asp Tyr Leu Gln Asn Gly Leu Pro Thr Glu Thr Thr Val Leu
        35                  40                  45

Gly Thr Val Gln Ile Leu Cys Cys Leu Leu Ile Ser Ser Leu Gly Ala
    50                  55                  60

Ile Leu Val Phe Ala Pro Tyr Pro Ser His Phe Asn Pro Ala Ile Ser
65                  70                  75                  80

Thr Thr Leu Met Ser Gly Tyr Pro Phe Leu Gly Ala Leu Cys Phe Gly
                85                  90                  95

Ile Thr Gly Ser Leu Ser Ile Ile Ser Gly Lys Gln Ser Thr Lys Pro
            100                 105                 110

Phe Asp Leu Ser Ser Leu Thr Ser Asn Ala Val Ser Ser Val Thr Ala
        115                 120                 125

Gly Ala Gly Leu Phe Leu Leu Ala Asp Ser Met Val Ala Leu Arg Thr
    130                 135                 140

Ala Ser Gln His Cys Gly Ser Glu Met Asp Tyr Leu Ser Ser Leu Pro
145                 150                 155                 160

Tyr Ser Glu Tyr Tyr Tyr Pro Ile Tyr Glu Ile Lys Asp Cys Leu Leu
                165                 170                 175

Thr Ser Val Ser Leu Thr Gly Val Leu Val Val Met Leu Ile Phe Thr
            180                 185                 190

Val Leu Glu Leu Leu Leu Ala Ala Tyr Ser Ser Val Phe Trp Trp Lys
        195                 200                 205

Gln Leu Tyr Ser Asn Asn Pro Gly Ser Ser Phe Ser Ser Thr Gln Ser
    210                 215                 220

Gln Asp His Ile Gln Gln Val Lys Lys Ser Ser Ser Arg Ser Trp Ile
225                 230                 235                 240

<210> SEQ ID NO 15
<211> LENGTH: 165
<212> TYPE: DNA
<213> ORGANISM: Artificial Sequence
<220> FEATURE:
<223> OTHER INFORMATION: Synthetic construct
<220> FEATURE:
<223> OTHER INFORMATION: phac

<400> SEQUENCE: 15
gcgattacgt aaagaagtta ttgaagcatc ctcgtcagta aaaagttaat cttttcaaca   60
gctgtcataa agttgtcacg gccgagactt atagtcgctt taattgtgag cggataacaa  120
tttgtaacta gtacgcaagt tcacgtaaaa agggtatcta gaatt                  165

<210> SEQ ID NO 16
<211> LENGTH: 217
<212> TYPE: DNA
<213> ORGANISM: Artificial Sequence
<220> FEATURE:

```
<223> OTHER INFORMATION: Synthetic construct
<220> FEATURE:
<223> OTHER INFORMATION: tphac

<400> SEQUENCE: 16
aggcctaacg ctcggttgcc gccgggcgtt ttttattgtt aaccatggag cgattacgta      60
aagaagttat tgaagcatcc tcgtcagtaa aaagttaatc ttttcaacag ctgtcataaa     120
gttgtcacgg ccgagactta tagtcgcttt aattgtgagc ggataacaat ttgtaactag     180
tacgcaagtt cacgtaaaaa gggtatctag aattatg                              217

<210> SEQ ID NO 17
<211> LENGTH: 31
<212> TYPE: DNA
<213> ORGANISM: Artificial Sequence
<220> FEATURE:
<223> OTHER INFORMATION: Synthetic construct
<220> FEATURE:
<223> OTHER INFORMATION: Lambda transcriptional terminator

<400> SEQUENCE: 17
aacgctcggt tgccgccggg cgttttttat t                                     31

<210> SEQ ID NO 18
<211> LENGTH: 19
<212> TYPE: DNA
<213> ORGANISM: Escherichia coli

<400> SEQUENCE: 18
aattgtgagc ggataacaa                                                   19

<210> SEQ ID NO 19
<211> LENGTH: 49
<212> TYPE: DNA
<213> ORGANISM: Artificial Sequence
<220> FEATURE:
<223> OTHER INFORMATION: Synthetic construct
<220> FEATURE:
<223> OTHER INFORMATION: tphac Upstream sequence

<400> SEQUENCE: 19
aggcctaacg ctcggttgcc gccgggcgtt ttttattgtt aaccatgga                  49

<210> SEQ ID NO 20
<211> LENGTH: 19
<212> TYPE: DNA
<213> ORGANISM: Artificial Sequence
<220> FEATURE:
<223> OTHER INFORMATION: Synthetic construct
<220> FEATURE:
<223> OTHER INFORMATION: Pho box

<400> SEQUENCE: 20
gctgtcataa agttgtcac                                                   19

<210> SEQ ID NO 21
<211> LENGTH: 2253
<212> TYPE: DNA
<213> ORGANISM: Homo sapiens

<400> SEQUENCE: 21
aatctaaagc ctcctcagcc ttctgagtca gcctgaaagg aacaggccga actgctgtat      60
gggctctact gccagtgtga cctcacccte tccagtcacc cctcctcagt tccagctatg     120
agttcctgca acttcacaca tgccaccttt gtgcttattg gtatcccagg attagagaaa     180
```

-continued

```
gcccatttct gggttggctt cccctcctt tccatgtatg tagtggcaat gtttggaaac    240
tgcatcgtgg tcttcatcgt aaggacggaa cgcagcctgc acgctccgat gtacctcttt    300
ctctgcatgc ttgcagccat tgacctggcc ttatccacat ccaccatgcc taagatcctt    360
gcccttttct ggtttgattc ccgagagatt agctttgagg cctgtcttac ccagatgttc    420
tttattcatg ccctctcagc cattgaatcc accatcctgc tggccatggc ctttgaccgt    480
tatgtggcca tctgccaccc actgcgccat gctgcagtgc tcaacaatac agtaacagcc    540
cagattggca tcgtggctgt ggtccgcgga tccctctttt ttttcccact gcctctgctg    600
atcaagcggc tggccttctg ccactccaat gtcctctcgc actcctattg tgtccaccag    660
gatgtaatga agttggccta tgcagacact ttgcccaatg tggtatatgg tcttactgcc    720
attctgctgg tcatgggcgt ggacgtaatg ttcatctcct tgtcctattt tctgataata    780
cgaacggttc tgcaactgcc ttccaagtca gagcgggcca aggcctttgg aacctgtgtg    840
tcacacattg gtgtggtact cgccttctat gtgccactta ttggcctctc agttgtacac    900
cgctttggaa acagccttca tcccattgtg cgtgttgtca tgggtgacat ctacctgctg    960
ctgcctcctg tcatcaatcc catcatctat ggtgccaaaa ccaaacagat cagaacacgg   1020
gtgctggcta tgttcaagat cagctgtgac aaggacttgc aggctgtggg aggcaagtga   1080
cccttaacac tacacttctc cttatctttta ttggcttgat aaacataatt atttctaaca   1140
ctagcttatt tccagttgcc cataagcaca tcagtacttt tctctggctg aatagtaaa    1200 ctaaagtatg gtacatctac ctaaaggact attatgtgga ataatacata ctaatgaagt   1260
attacatgat ttaaagacta caataaaacc aaacatgctt ataacattaa gaaaaacaat   1320
aaagatacat gattgaaacc aagttgaaaa atagcatatg ccttggagga aatgtgctca   1380
aattactaat gatttagtgt tgtccctact ttctctctct tttttctttc tttttttta    1440 ttatggttag ctgtcacata caactgcact ccagcctggg caacagagca agaccctgtc   1500
tcaaagcata aaatggaata acatatcaaa tgaaacaggg aaaatgaagc tgacaattta   1560
tggaagccag ggcttgtcac agtctctact gttattatgc attacctggg aatttatata   1620
agcccttaat aataatgcca atgaacatct catgtgtgct cacaatgttc tggcactatt   1680
ataagtgctt cacaggtttt atgtgttctt cgtaacttta tggagtaggt accatttgtg   1740
tctctttatt ataagtgaga gaaatgaagt ttatattatc aaggggacta aagtcacacg   1800
gcttgtgggc actgtgccaa gatttaaaat taaatttgat ggttgaatac agttacttaa   1860
tgaccatgtt atattgcttc ctgtgtaaca tctgccattt atttcctcag ctgtacaaat   1920
cctctgtttt ctctctgtta cacactaaca tcaatggctt tgtacttgtg atgagagata   1980
accttgccct agttgtgggc aacacatgca gaataatcct gttttacagc tgcctttcgt   2040
gatcttattg cttgctttt tccagattca gggagaatgt tgttgtctat ttgtctctta    2100
catctccttg atcatgtctt cattttttaa tgtgctctgt acctgtcaaa aattttgaat   2160
gtacaccaca tgctattgtc tgaacttgag tataagataa aataaatttt tattttaaat   2220
tgtaaaaaaa aaaaaaaaaa aaaaaaaaaa aaa                                2253
```

<210> SEQ ID NO 22
<211> LENGTH: 320
<212> TYPE: PRT
<213> ORGANISM: Homo sapiens

<400> SEQUENCE: 22

```
Met Ser Ser Cys Asn Phe Thr His Ala Thr Phe Val Leu Ile Gly Ile
1               5                   10                  15

Pro Gly Leu Glu Lys Ala His Phe Trp Val Gly Phe Pro Leu Leu Ser
            20                  25                  30

Met Tyr Val Val Ala Met Phe Gly Asn Cys Ile Val Val Phe Ile Val
        35                  40                  45

Arg Thr Glu Arg Ser Leu His Ala Pro Met Tyr Leu Phe Leu Cys Met
    50                  55                  60

Leu Ala Ala Ile Asp Leu Ala Leu Ser Thr Ser Thr Met Pro Lys Ile
65              70                  75                  80

Leu Ala Leu Phe Trp Phe Asp Ser Arg Glu Ile Ser Phe Glu Ala Cys
                85                  90                  95

Leu Thr Gln Met Phe Phe Ile His Ala Leu Ser Ala Ile Glu Ser Thr
                100                 105                 110

Ile Leu Leu Ala Met Ala Phe Asp Arg Tyr Val Ala Ile Cys His Pro
            115                 120                 125

Leu Arg His Ala Ala Val Leu Asn Asn Thr Val Thr Ala Gln Ile Gly
    130                 135                 140

Ile Val Ala Val Val Arg Gly Ser Leu Phe Phe Phe Pro Leu Pro Leu
145                 150                 155                 160

Leu Ile Lys Arg Leu Ala Phe Cys His Ser Asn Val Leu Ser His Ser
                165                 170                 175

Tyr Cys Val His Gln Asp Val Met Lys Leu Ala Tyr Ala Asp Thr Leu
            180                 185                 190

Pro Asn Val Val Tyr Gly Leu Thr Ala Ile Leu Leu Val Met Gly Val
    195                 200                 205

Asp Val Met Phe Ile Ser Leu Ser Tyr Phe Leu Ile Ile Arg Thr Val
210                 215                 220

Leu Gln Leu Pro Ser Lys Ser Glu Arg Ala Lys Ala Phe Gly Thr Cys
225                 230                 235                 240

Val Ser His Ile Gly Val Val Leu Ala Phe Tyr Val Pro Leu Ile Gly
                245                 250                 255

Leu Ser Val Val His Arg Phe Gly Asn Ser Leu His Pro Ile Val Arg
            260                 265                 270

Val Val Met Gly Asp Ile Tyr Leu Leu Leu Pro Pro Val Ile Asn Pro
    275                 280                 285

Ile Ile Tyr Gly Ala Lys Thr Lys Gln Ile Arg Thr Arg Val Leu Ala
290                 295                 300

Met Phe Lys Ile Ser Cys Asp Lys Asp Leu Gln Ala Val Gly Gly Lys
305                 310                 315                 320

<210> SEQ ID NO 23
<211> LENGTH: 1182
<212> TYPE: DNA
<213> ORGANISM: Homo sapiens

<400> SEQUENCE: 23
atggagacca ccatggggtt catggatgac aatgccacca acacttccac cagcttcctt     60
tctgtgctca accctcatgg agcccatgcc acttccttcc cattcaactt cagctacagc    120
gactatgata tgccttttga tgaagatgag gatgtgacca attccaggac gttctttgct    180
gccaagattg tcattgggat ggccctggtg gcatcatgc tggtctgcgg cattggaaac     240
ttcatcttta tcgctgccct ggtccgctac aagaaactgc gcaacctcac caacctgctc    300
atcgccaacc tggccatctc tgacttcctg gtggccattg tctgctgccc ctttgagatg    360
```

```
gactactatg tggtgcgcca gctctcctgg gagcacggcc acgtcctgtg cacctctgtc    420
aactacctgc gcactgtctc tctctatgtc tccaccaatg ccctgctggc catcgccatt    480
gacaggtatc tggctattgt ccatccgctg agaccacgga tgaagtgcca aacagccact    540
ggcctgattg ccttggtgtg gacggtgtcc atcctgatcg ccatcccttc cgcctacttc    600
accaccgaga cggtcctcgt cattgtcaag agccaggaaa agatcttctg cggccagatc    660
tggcctgtgg accagcagct ctactacaag tcctacttcc tctttatctt tggcatagaa    720
ttcgtgggcc ccgtggtcac catgaccctg tgctatgcca ggatctcccg ggagctctgg    780
ttcaaggcgg tccctggatt ccagacagag cagatccgca agaggctgcg ctgccgcagg    840
aagacggtcc tggtgctcat gtgcatcctc accgcctacg tgctatgctg ggcgcccttc    900
tacggcttca ccatcgtgcg cgacttcttc cccaccgtgt ttgtgaagga aagcactac    960 ctcactgcct tctacatcgt cgagtgcatc gccatgagca acagcatgat caacactctg    1020
tgcttcgtga ccgtcaagaa cgacaccgtc aagtacttca aaaagatcat gttgctccac    1080
tggaaggctt cttacaatgg cggtaagtcc agtgcagacc tggacctcaa gacaattggg    1140
atgcctgcca ccgaagaggt ggactgcatc agactaaaat aa                       1182
```

<210> SEQ ID NO 24
<211> LENGTH: 393
<212> TYPE: PRT
<213> ORGANISM: Homo sapiens

<400> SEQUENCE: 24

```
Met Glu Thr Thr Met Gly Phe Met Asp Asp Asn Ala Thr Asn Thr Ser
1               5                   10                  15

Thr Ser Phe Leu Ser Val Leu Asn Pro His Gly Ala His Ala Thr Ser
                20                  25                  30

Phe Pro Phe Asn Phe Ser Tyr Ser Asp Tyr Asp Met Pro Leu Asp Glu
            35                  40                  45

Asp Glu Asp Val Thr Asn Ser Arg Thr Phe Phe Ala Ala Lys Ile Val
        50                  55                  60

Ile Gly Met Ala Leu Val Gly Ile Met Leu Val Cys Gly Ile Gly Asn
65                  70                  75                  80

Phe Ile Phe Ile Ala Ala Leu Val Arg Tyr Lys Lys Leu Arg Asn Leu
                85                  90                  95

Thr Asn Leu Leu Ile Ala Asn Leu Ala Ile Ser Asp Phe Leu Val Ala
            100                 105                 110

Ile Val Cys Cys Pro Phe Glu Met Asp Tyr Tyr Val Val Arg Gln Leu
        115                 120                 125

Ser Trp Glu His Gly His Val Leu Cys Thr Ser Val Asn Tyr Leu Arg
    130                 135                 140

Thr Val Ser Leu Tyr Val Ser Thr Asn Ala Leu Leu Ala Ile Ala Ile
145                 150                 155                 160

Asp Arg Tyr Leu Ala Ile Val His Pro Leu Arg Pro Arg Met Lys Cys
                165                 170                 175

Gln Thr Ala Thr Gly Leu Ile Ala Leu Val Trp Thr Val Ser Ile Leu
            180                 185                 190

Ile Ala Ile Pro Ser Ala Tyr Phe Thr Thr Glu Thr Val Leu Val Ile
        195                 200                 205

Val Lys Ser Gln Glu Lys Ile Phe Cys Gly Gln Ile Trp Pro Val Asp
    210                 215                 220
```

```
Gln Gln Leu Tyr Tyr Lys Ser Tyr Phe Leu Phe Ile Phe Gly Ile Glu
225                 230                 235                 240

Phe Val Gly Pro Val Val Thr Met Thr Leu Cys Tyr Ala Arg Ile Ser
            245                 250                 255

Arg Glu Leu Trp Phe Lys Ala Val Pro Gly Phe Gln Thr Glu Gln Ile
        260                 265                 270

Arg Lys Arg Leu Arg Cys Arg Lys Thr Val Leu Val Leu Met Cys
    275                 280                 285

Ile Leu Thr Ala Tyr Val Leu Cys Trp Ala Pro Phe Tyr Gly Phe Thr
    290                 295                 300

Ile Val Arg Asp Phe Phe Pro Thr Val Phe Val Lys Glu Lys His Tyr
305                 310                 315                 320

Leu Thr Ala Phe Tyr Ile Val Glu Cys Ile Ala Met Ser Asn Ser Met
                325                 330                 335

Ile Asn Thr Leu Cys Phe Val Thr Val Lys Asn Asp Thr Val Lys Tyr
                340                 345                 350

Phe Lys Lys Ile Met Leu Leu His Trp Lys Ala Ser Tyr Asn Gly Gly
            355                 360                 365

Lys Ser Ser Ala Asp Leu Asp Leu Lys Thr Ile Gly Met Pro Ala Thr
    370                 375                 380

Glu Glu Val Asp Cys Ile Arg Leu Lys
385                 390

<210> SEQ ID NO 25
<211> LENGTH: 79
<212> TYPE: PRT
<213> ORGANISM: Escherichia coli

<400> SEQUENCE: 25

Met Lys Ala Ile Phe Val Leu Lys Gly Ser Leu Asp Arg Asp Leu Asp
1               5                   10                  15

Ser Arg Ile Glu Leu Glu Met Arg Thr Lys His Lys Glu Leu Ser Glu
            20                  25                  30

His Leu Met Leu Val Asp Leu Ala Arg Asn Asp Leu Ala Arg Ile Cys
        35                  40                  45

Thr Pro Gly Ser Arg Tyr Val Ala Asp Leu Thr Lys Val Asp Arg Tyr
    50                  55                  60

Ser Tyr Val Met His Leu Val Ser Arg Val Val Gly Glu Leu Arg
65                  70                  75

<210> SEQ ID NO 26
<211> LENGTH: 48
<212> TYPE: PRT
<213> ORGANISM: Escherichia coli

<400> SEQUENCE: 26

Met Lys Ala Ile Phe Val Leu Lys Gly Ser Leu Asp Arg Asp Leu Ala
1               5                   10                  15

Arg Ile Ile Val Ile Arg Ser Ala Leu Val Glu Asn Gly Ile Ala Thr
            20                  25                  30

Val Gln Ala Gly Ala Gly Val Val Leu Asp Ser Gly Ala Ala His Tyr
        35                  40                  45

<210> SEQ ID NO 27
<211> LENGTH: 10
<212> TYPE: PRT
<213> ORGANISM: Artificial Sequence
<220> FEATURE:
```

```
<223> OTHER INFORMATION: Synthetic construct

<400> SEQUENCE: 27

Met Lys Ala Ile Phe Val Leu Lys Gly Ser
1               5                  10

<210> SEQ ID NO 28
<211> LENGTH: 21
<212> TYPE: DNA
<213> ORGANISM: Escherichia coli

<400> SEQUENCE: 28
atgaaacacc aacaccaaca a                                              21

<210> SEQ ID NO 29
<211> LENGTH: 69
<212> TYPE: PRT
<213> ORGANISM: Escherichia coli

<400> SEQUENCE: 29

Leu Asp Arg Asp Leu Asp Ser Arg Ile Glu Leu Glu Met Arg Thr Lys
1               5                   10                  15

His Lys Glu Leu Ser Glu His Leu Met Leu Val Asp Leu Ala Arg Asn
            20                  25                  30

Asp Leu Ala Arg Ile Cys Thr Pro Gly Ser Arg Tyr Val Ala Asp Leu
        35                  40                  45

Thr Lys Val Asp Arg Tyr Ser Tyr Val Met His Leu Val Ser Arg Val
    50                  55                  60

Val Gly Glu Leu Arg
65

<210> SEQ ID NO 30
<211> LENGTH: 38
<212> TYPE: PRT
<213> ORGANISM: Escherichia coli

<400> SEQUENCE: 30

Leu Asp Arg Asp Leu Ala Arg Ile Ile Val Ile Arg Ser Ala Leu Val
1               5                   10                  15

Glu Asn Gly Ile Ala Thr Val Gln Ala Gly Ala Gly Val Val Leu Asp
            20                  25                  30

Ser Gly Ala Ala His Tyr
        35

<210> SEQ ID NO 31
<211> LENGTH: 6
<212> TYPE: PRT
<213> ORGANISM: Artificial Sequence
<220> FEATURE:
<223> OTHER INFORMATION: Synthetic construct
<220> FEATURE:
<223> OTHER INFORMATION: Thrombin recognition site

<400> SEQUENCE: 31

Leu Val Pro Arg Gly Ser
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic construct
```

```
<220> FEATURE:
<223> OTHER INFORMATION: Flag tag

<400> SEQUENCE: 32

Asp Tyr Lys Asp Asp Asp Lys
1               5

<210> SEQ ID NO 33
<211> LENGTH: 10
<212> TYPE: PRT
<213> ORGANISM: Artificial Sequence
<220> FEATURE:
<223> OTHER INFORMATION: Synthetic construct
<220> FEATURE:
<223> OTHER INFORMATION: Translation initiation sequence

<400> SEQUENCE: 33

Met Gly Ser Ser His His His His His
1               5                   10

<210> SEQ ID NO 34
<211> LENGTH: 30
<212> TYPE: DNA
<213> ORGANISM: Artificial Sequence
<220> FEATURE:
<223> OTHER INFORMATION: Synthetic construct
<220> FEATURE:
<223> OTHER INFORMATION: Translation initiation sequence

<400> SEQUENCE: 34
atgggcagca gccatcatca tcatcatcat                                      30

<210> SEQ ID NO 35
<211> LENGTH: 30
<212> TYPE: DNA
<213> ORGANISM: Artificial Sequence
<220> FEATURE:
<223> OTHER INFORMATION: Synthetic construct
<220> FEATURE:
<223> OTHER INFORMATION: Translation initiation sequence

<400> SEQUENCE: 35
atgaaagcaa ttttcgtact gaaaggttca                                      30

<210> SEQ ID NO 36
<211> LENGTH: 9
<212> TYPE: PRT
<213> ORGANISM: Escherichia coli

<400> SEQUENCE: 36

Lys Ala Ile Phe Val Leu Lys Gly Ser
1               5
```

METHODS FOR PRODUCING SOLUBLE MEMBRANE-SPANNING PROTEINS

CROSS-REFERENCE TO RELATED APPLICATIONS

This application is a divisional of U.S. Ser. No. 12/489,343, filed Jun. 22, 2009, currently pending, which is a continuation of U.S. Ser. No. 11/316,370, filed Dec. 22, 2005, now pending, which claims the benefit of priority under 35 U.S.C. §119(e) of U.S. Provisional Application Ser. No. 60/639,233, filed Dec. 22, 2004. The aforementioned applications are explicitly incorporated herein by reference in their entirety and for all purposes.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 146392001210Seqlist.txt | Jun. 8, 2009 | 42,185 bytes |

BACKGROUND

Complex, membrane-spanning proteins are difficult to express in host cells. In general, these proteins are toxic to the host, and various expression systems yield low quantities of expressed protein. In addition, these membrane-spanning polypeptides are difficult to solubilize, with aggregation and denaturing causing difficulties in producing a protein product of sufficient quality and quantity for effective use.

One example of a membrane-spanning protein is the 4-domain subfamily A (MS4A) gene family that includes CD20, high affinity IgE receptor β chain, HTm4, and the like. These proteins are structurally related, at least in the four membrane-spanning domains in the cell surface (Ishibashi et al., 2001, *Gene* 264:87-93). Although overall amino acid sequence identity ranges from 25-40% in the polypeptides of the MS4A family, amino acids of the first three membrane-spanning domains share higher identity and homology than the overall polypeptide (Ishibashi et al., 2001, Supra; Liang et al., 2001, *Genomics* 72:119-127). Structurally, the MS4A polypeptides also share a common motif of an extracellular loop. Both the N- and C-termini of the MS4A polypeptide are found on the cytoplasm side of the cell membrane (Ishibashi et al., 2001, Supra). The N- and C-termini display a much greater sequence divergence among polypeptides of the MS4A gene family (Ishibashi et al., 2001, Supra).

Despite many structural similarities, polypeptides of the MS4A gene family are not uniformly expressed in individual cell types (Liang et al., 2001, Supra). CD20 is expressed exclusively in B cells (Stashenko et al., 1980, *J. Immunol.*, 125: 1678-1685). High-affinity IgE receptor β chain (FcεRIβ) is expressed exclusively in mast cells and basophils (Kinet, 1999, *Annu. Rev. Immunol.*, 17: 931-972). FcεRIβ binds IgE and mediates intracellular signaling (i.e., degranulation) triggered by antigen binding (Dombrowicz et al., 1998, *Immunity*, 8: 517-529; Lin et al., 1996, *Cell*, 85: 985-995). HTm4 is expressed in hematopoietic tissue and serves as a hematopoietic cell cycle regulator (Donato et al., 2002, *J. Clin. Invest.*, 109: 51-58). These proteins do share a common feature, the complex structure of membrane-spanning peptides. This feature makes the protein very difficult to express in a host cell and to solubilize from the cell membrane in a "native" configuration.

Membrane-spanning polypeptides, for example CD20, are potential targets for therapeutics in the treatment of diseases such as cancer and autoimmune diseases. CD20 was first identified as a marker for B cells over 20 years ago and is now established as a marker present on the majority of B cell lymphomas. CD20 is a target for monoclonal antibody therapy in the treatment of non-Hodgkins lymphoma (NHL), and specifically, it is the target for the chimeric antibody rituximab (RITUXAN®), a lead therapeutic in the treatment of NHL. Rituximab recognizes CD20 expressed on B cells. Binding of rituximab is conformation-dependent and binds to CD20 having dependent, loop structure between the third and fourth transmembrane helical regions containing cysteine residues at positions 167 and 183.

A significant hurdle in the development of therapeutics that target membrane-spanning polypeptides, such as CD20, is the inability to produce sufficient quantities of these polypeptides in host cells, particularly in bacterial cells, and the inability to produce purified recombinant or naturally occurring membrane-spanning polypeptides in a native conformation. Methods for producing and solubilizing naturally occurring and/or recombinant membrane-spanning polypeptides in a native conformation are needed.

SUMMARY OF THE INVENTION

It has now been discovered that membrane-spanning polypeptides, for example, those consisting of single or multiple membrane-spanning domains, can be efficiently produced in bacterial cell hosts and solubilized from bacterial cell membranes with good yield and with sufficient native conformation to be useful as immunogens and as ligands, for example, in quantitative assays. Membrane-spanning polypeptides can be produced, isolated, and solubilized by the methods described herein, in useful quantities and with a useful "native" conformation.

Methods for producing membrane-spanning polypeptides include expression in cells, for example in bacterial cells, under a strong, tightly controlled promoter, for example the phoA promoter in *E. coli*. In an embodiment, the tightly controlled promoter contains both a positive control element and a negative control element, and may contain a plurality of these. The promoter may be a mutant promoter, for example, where a heterologous positive or negative control element has been inserted. The promoter may further comprise transcriptional terminators, for example, lambda transcriptional terminators, positioned so as to prevent possible read-through of a potential upstream promoter. For expression of protein in *E. coli*, the promoter may be, for example, phoA, or mutations thereof containing added negative control elements, such as phac and tphac, mutant promoters disclosed in the Examples below that contain an added lac operator.

Vectors for expressing the membrane-spanning polypeptides include a polynucleotide sequence encoding the membrane-spanning polypeptide under the control of the tightly controlled promoter. Such polypeptides include, for example, those having at least four membrane-spanning domains, such as CD20 and the C2S-CD20 mutant disclosed in the Examples below. The encoded polypeptides may have one, two, three, four, five, six, seven, eight, nine, ten, eleven, twelve or twenty four or more membrane-spanning domains. Further examples include the endocrine gland-derived vascular endothelial growth factor (EG-VEGF) receptor, GPR73, having seven membrane-spanning domains, the high affinity IgE receptor beta chain (FcεRIβ), HTm4, MS4A4A, MS4A6, MS4A7, and RA1c. The vector may also include rare-codon tRNA genes of the host bacterial cell, and/or a polynucleotide sequence positioned adjacent to the first codon, encoding a leader peptide for enhancing translation initiation. The leader sequence generally contains a strong translation initiation sequence (TIS) and a spacer sequence for efficient elongation. A translation initiation sequence is referred to as TIS in this application but is also referred to as a translation initiation region (TIR).

In an embodiment, the leader sequence contains a strong TIS, encoding at least a portion of the trp leader sequence, for example, about 6 to about 12 amino acids. A spacer sequence separates the translation initiation sequence from the first transmembrane region, and generally encodes a small, internal portion of a protein known to be well expressed in the host cell, such as the "E" protein in *E. coli*, for example. The spacer sequence is generally unstructured and largely hydrophilic.

In one embodiment, a vector for expressing soluble, multi-membrane spanning proteins contains a tightly controlled promoter, such as the phoA promoter or a mutant thereof, negative and/or positive regulatory elements, and contains a polynucleotide sequence encoding a leader sequence containing a strong translation initiation sequence and a translation elongation spacer sequence positioned between the TIS and the first transmembrane region of the protein.

Vectors can contain, for example, a phoA, phac, or tphac promoter, a negative control element such as the lac operator, a leader sequence encoding a translation initiation sequence, for example, a portion of the trp leader such as the nine amino acid sequence KAIFVLKGS (SEQ ID NO: 36), and a spacer sequence encoding a translation elongation sequence such as a portion of the trp E gene, for example, as found in the LE leader (SEQ ID NO: 25) or sLE leader (SEQ ID NO: 26) described herein.

Membrane-spanning polypeptides may be harvested and purified from host cell membranes by solubilizing in detergent. In one embodiment, non-ionic or zwitterionic detergents, such as n-dodecylphosphocholine, (DDPC), are used to solubilize membrane-spanning polypeptides. Isolated multi-membrane-spanning polypeptides such as CD20 are soluble in these detergents. Isolated, soluble multi-membrane-spanning polypeptides contain sufficient "native" structure to be recognized by antibodies that recognize the polypeptides when expressed on cells, and are useful as immunogens and as assay ligands.

Binding was determined by competition of unlabeled rituximab IgG against $^{125}$I-IgG for donor 1 (panel a) or unlabeled rituximab Fab against $^{125}$I-Fab for donor 4 (panel b). See Table 4 for affinities and number of receptors from each donor.

Figure 8:
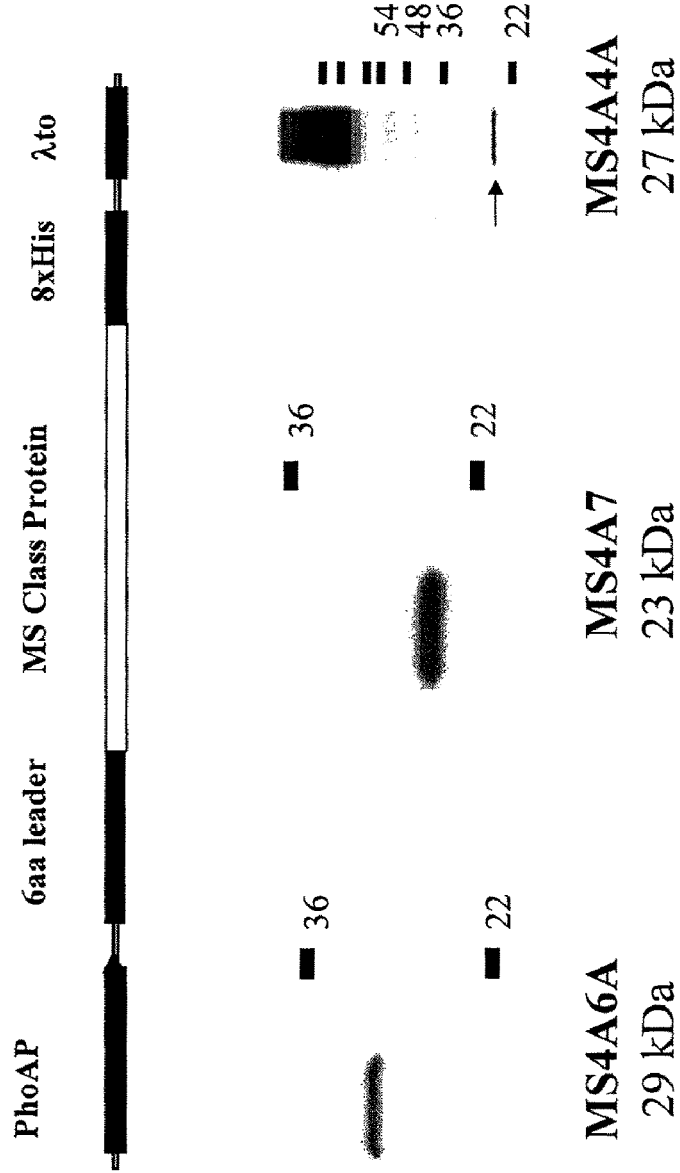

FIG. 8 shows an expression vector construct and a Western blot showing expression of MS4A family polypeptides in *E. coli*, including MS4A6A, MS4A7, and MS4A4A polypeptides.

Figure 9:
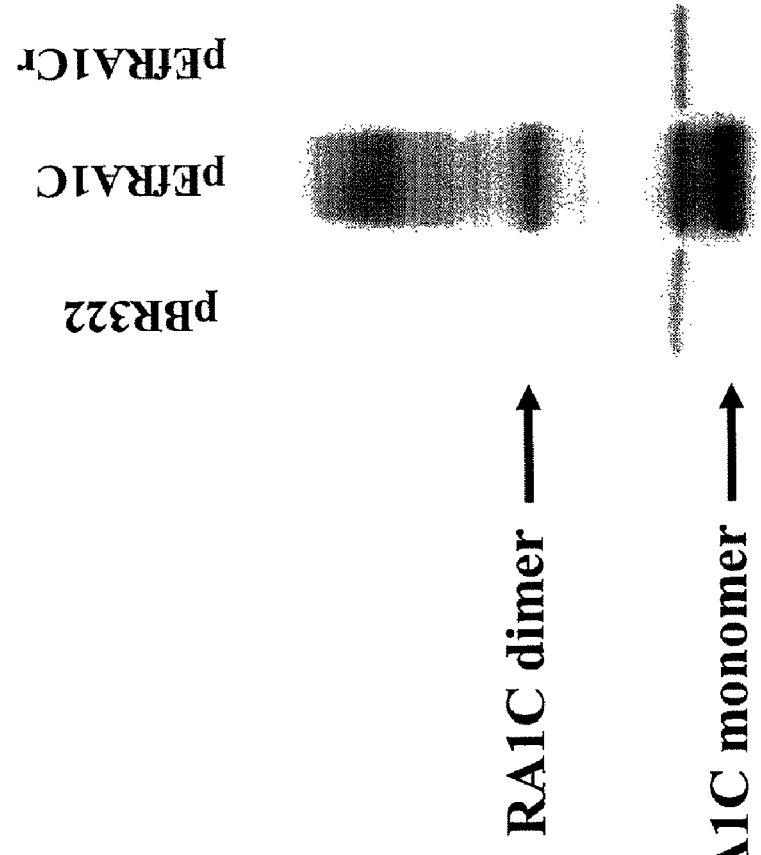

FIG. 9 is a Western blot showing RA1c polypeptide expressed due to leakage from non-induced phoA promoter (pEfRA1C) and mutant promoter, phac (pEfRA1Cr), as detected by an anti-His tag antibody.

Figure 10:
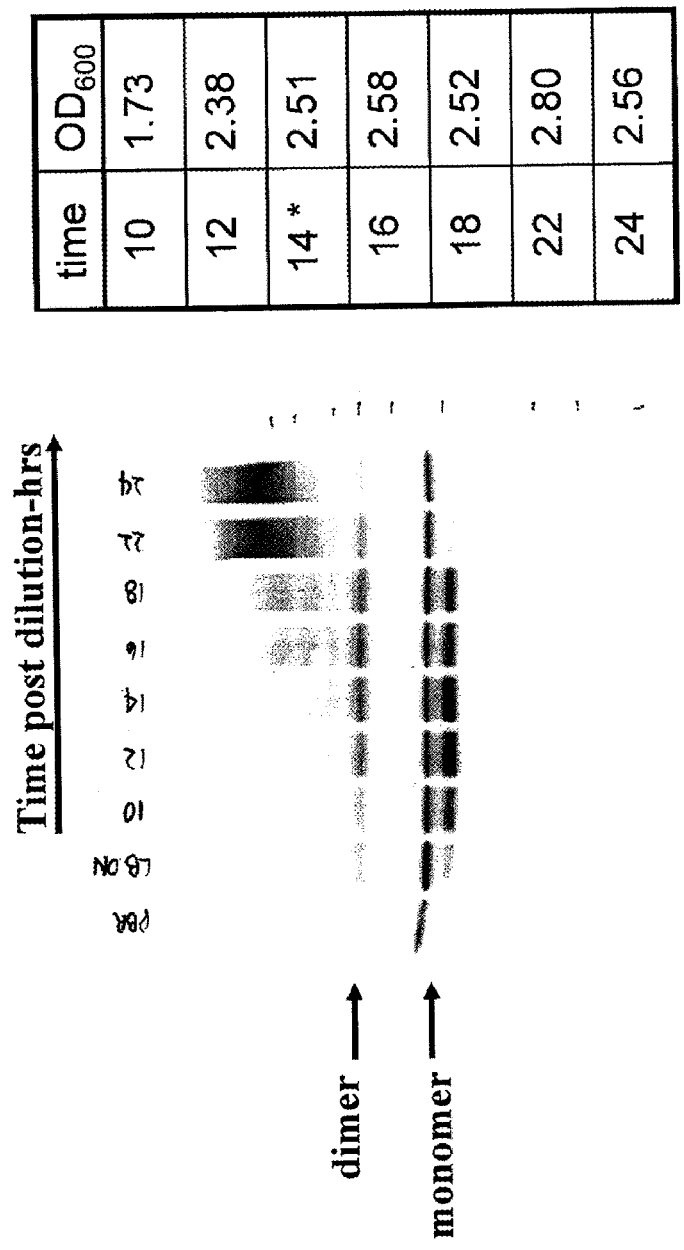

FIG. 10 is a Western blot showing a time course of RA1c polypeptide expression from phoA promoter (pEfRA1C) induced by dilution into phosphate-limiting media.

Figure 11:
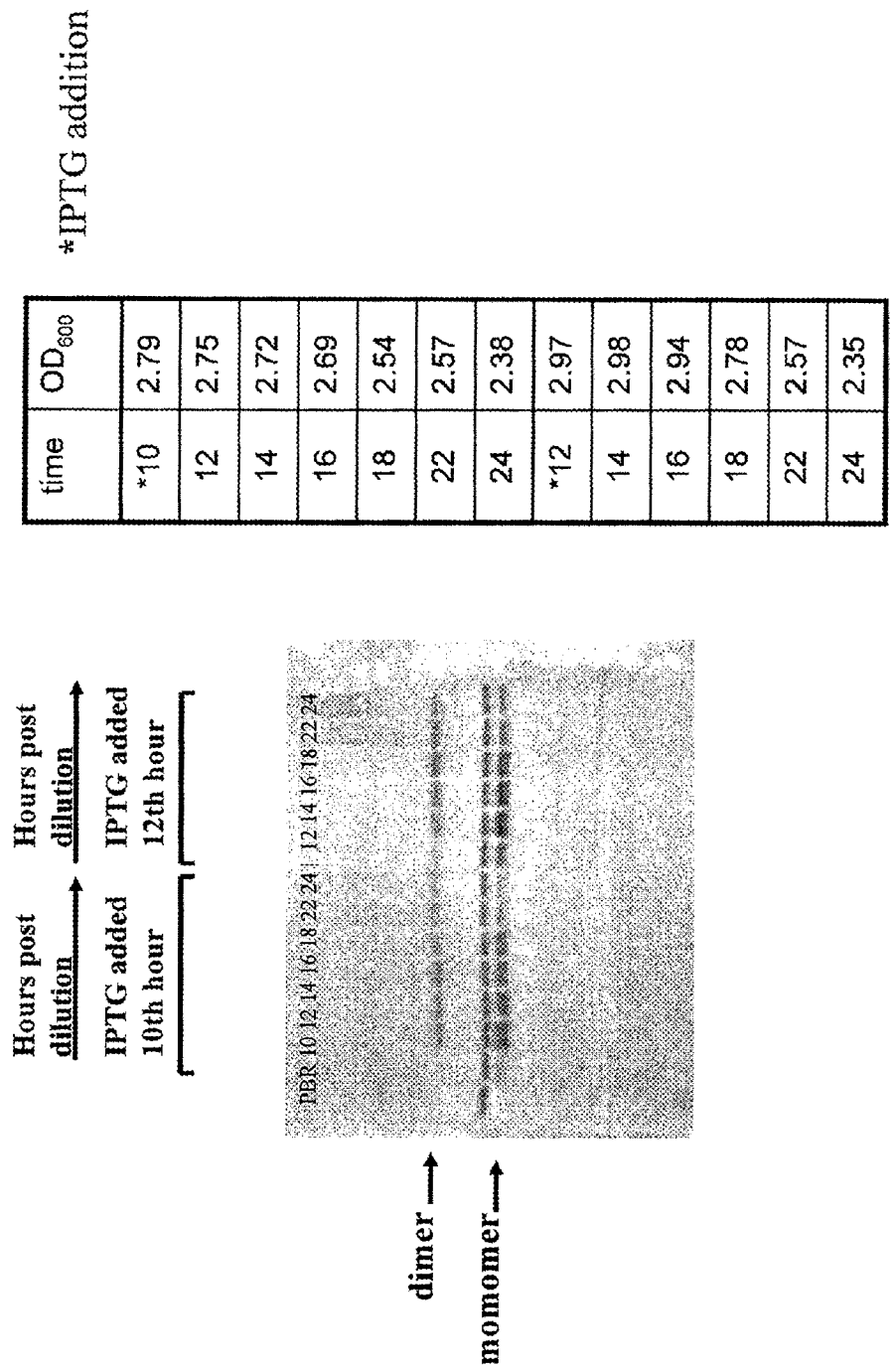

FIG. 11 is a Western blot showing a time course of RA1c polypeptide expression from phac promoter (pEfRA1Cr) induced by dilution into phosphate-limiting media and by IPTG addition.

Figure 12:
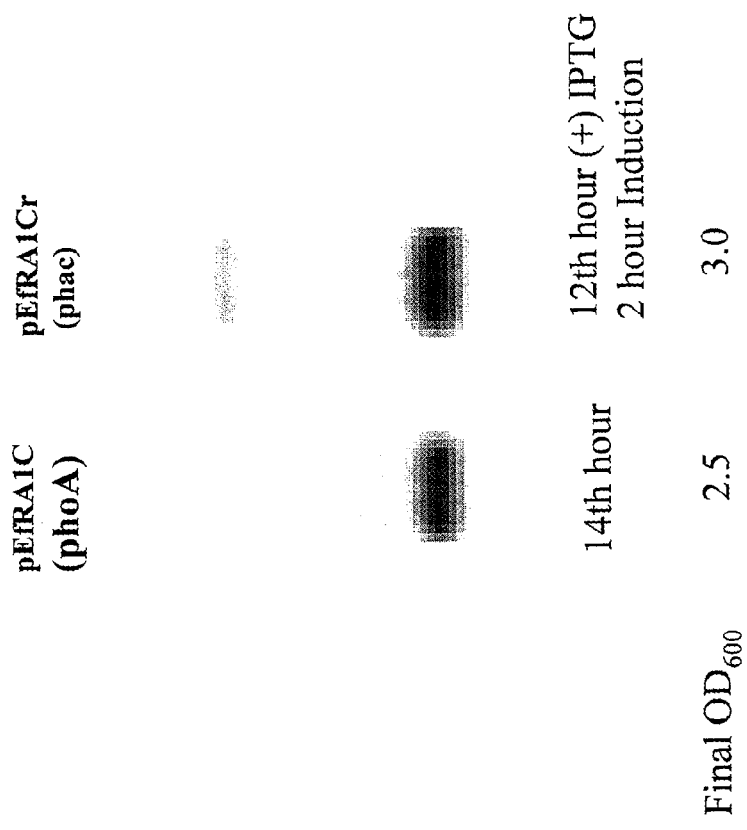

FIG. 12 is a Western blot comparing maximal expression of RA1c from induced phoA and phac promoters.

Figure 13:
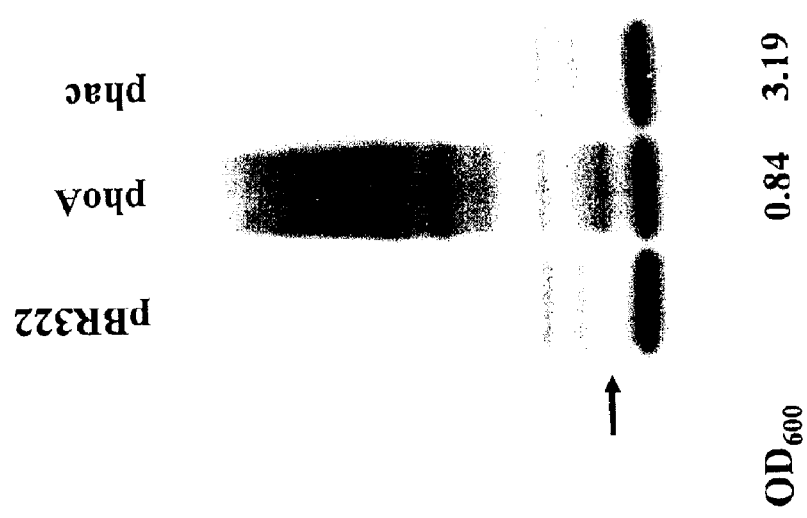

FIG. 13 is a Western blot showing EG-VEGF receptor, GPR73 polypeptide, expressed in E. coli due to leakage from non-induced phoA promoter (middle lane) and mutant promoter, phac (right lane).

Figure 14:
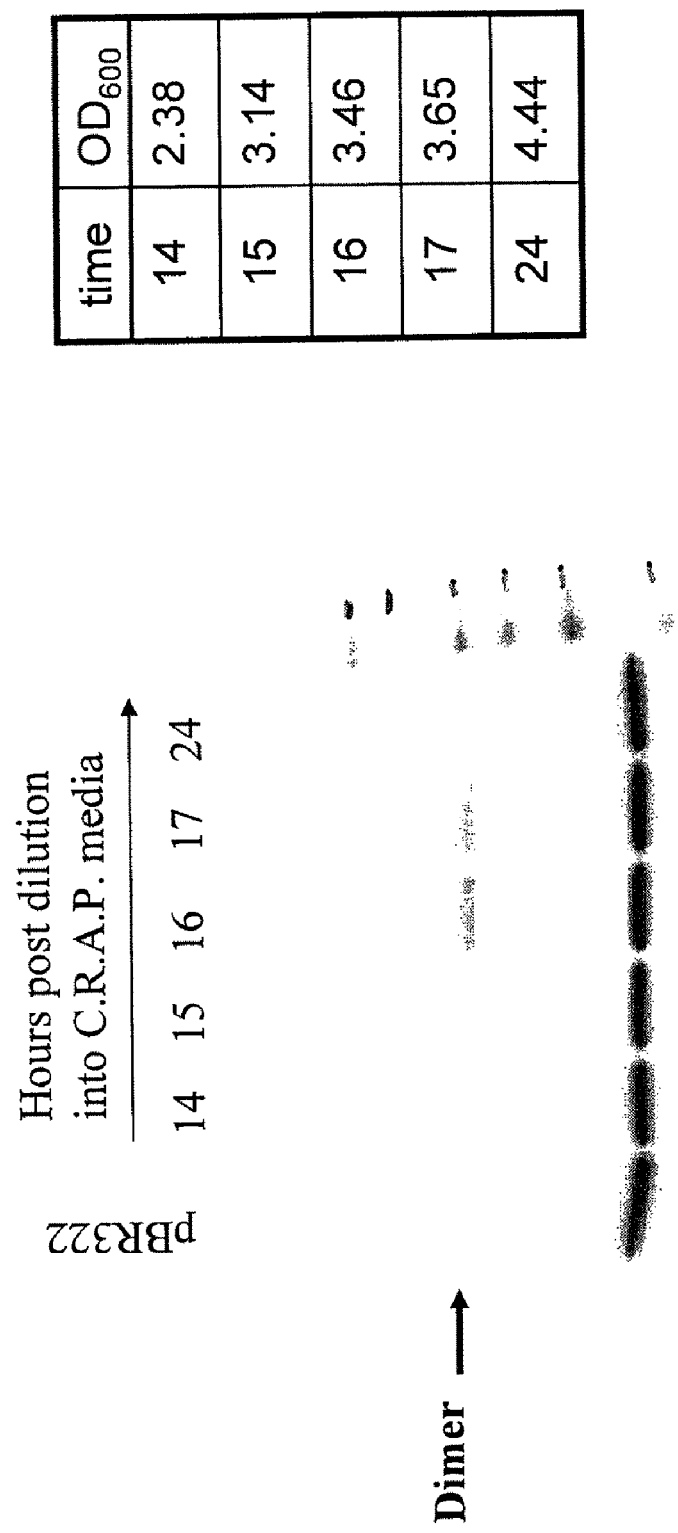

FIG. 14 is a Western blot showing a time course of GPR73 polypeptide expression from phoA promoter induced by dilution into phosphate-limiting media.

Figure 15:
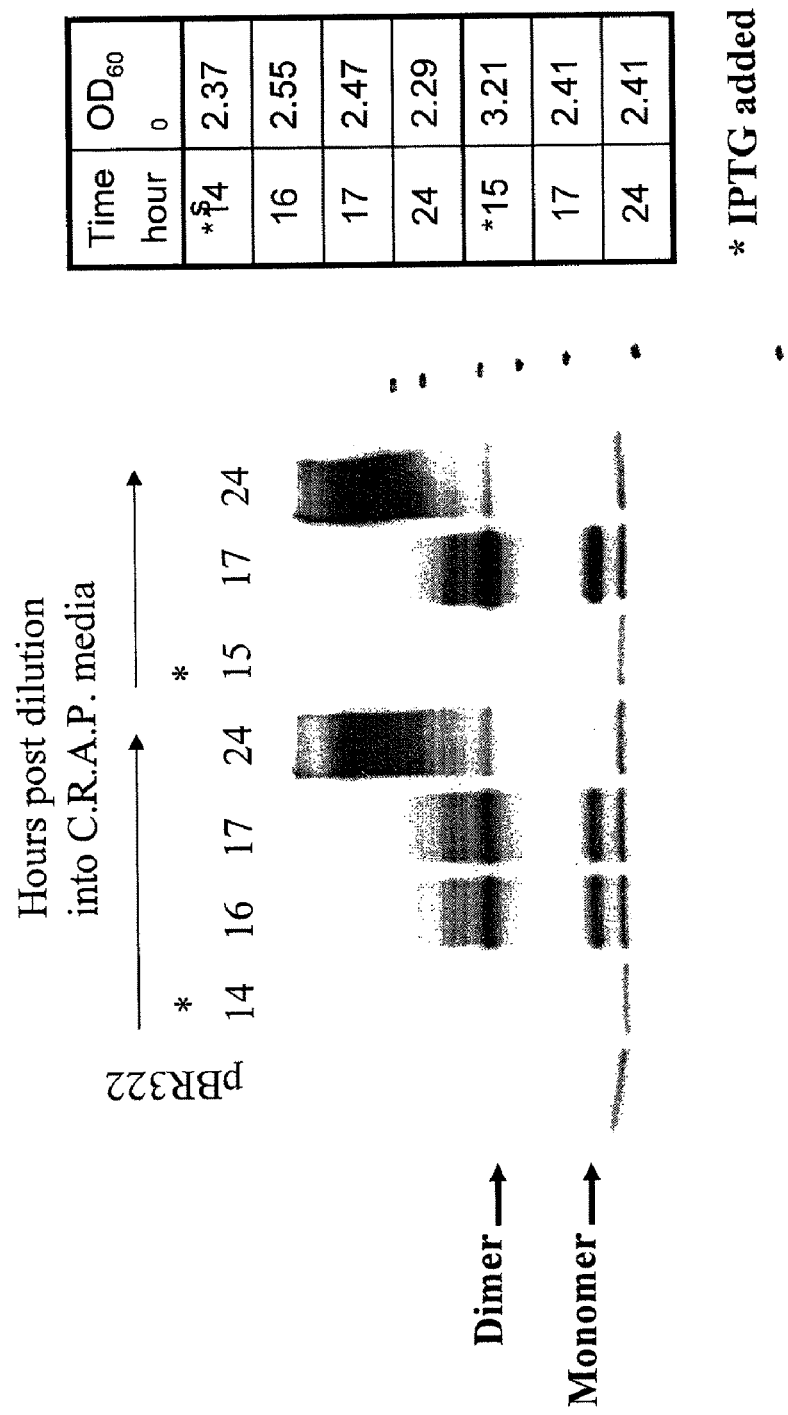

FIG. 15 is a Western blot showing a time course of GPR73 polypeptide expression from phac promoter induced by dilution into phosphate-limiting media and by addition of IPTG.

Figure 16:
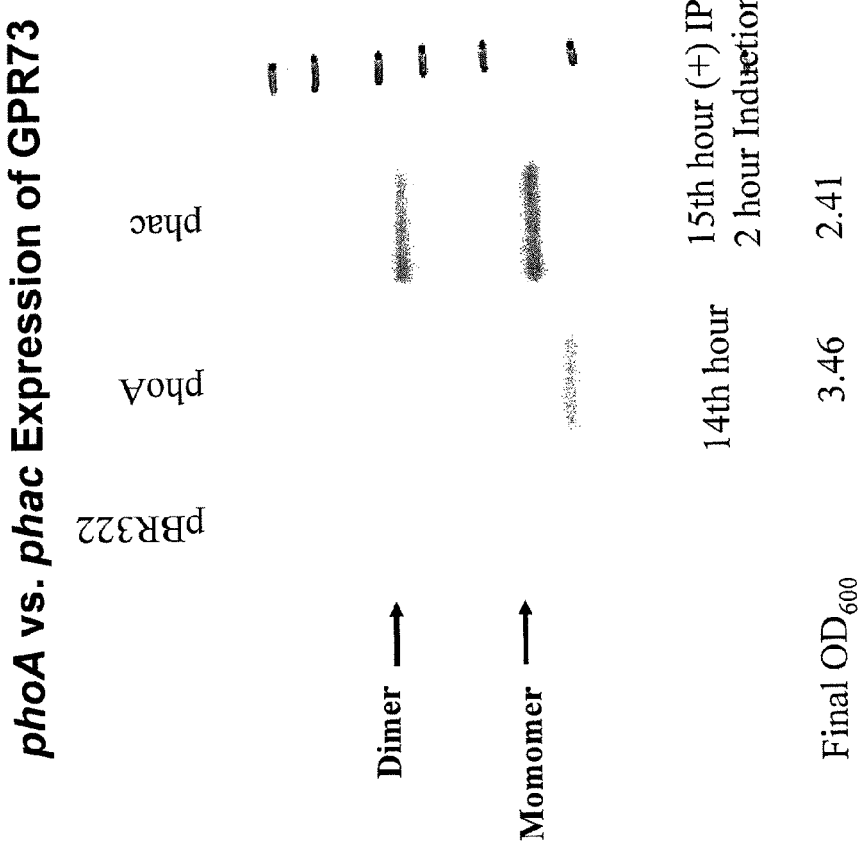

FIG. 16 is a Western blot comparing maximal expression of GPR73 from induced phoA and phac promoters.

Figure 17:
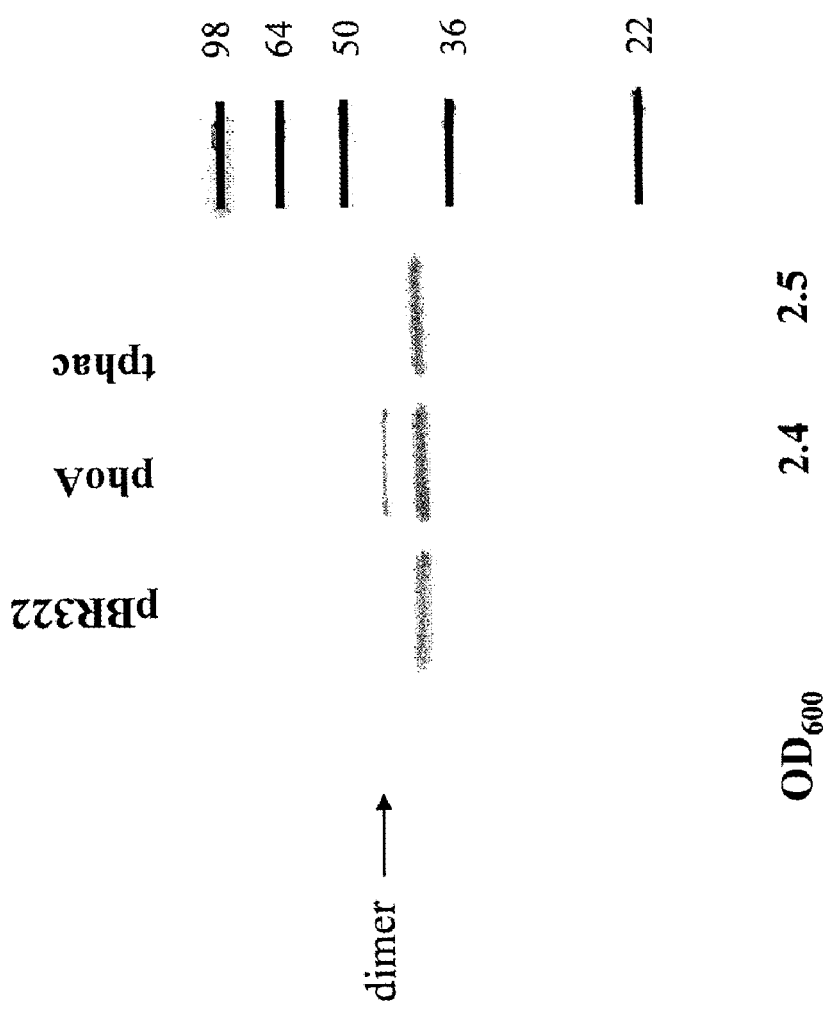

FIG. 17 is a Western blot showing MS4A4A polypeptide expressed due to leakage from non-induced phoA promoter (middle lane) and mutant promoter, tphac (right lane).

Figure 18:
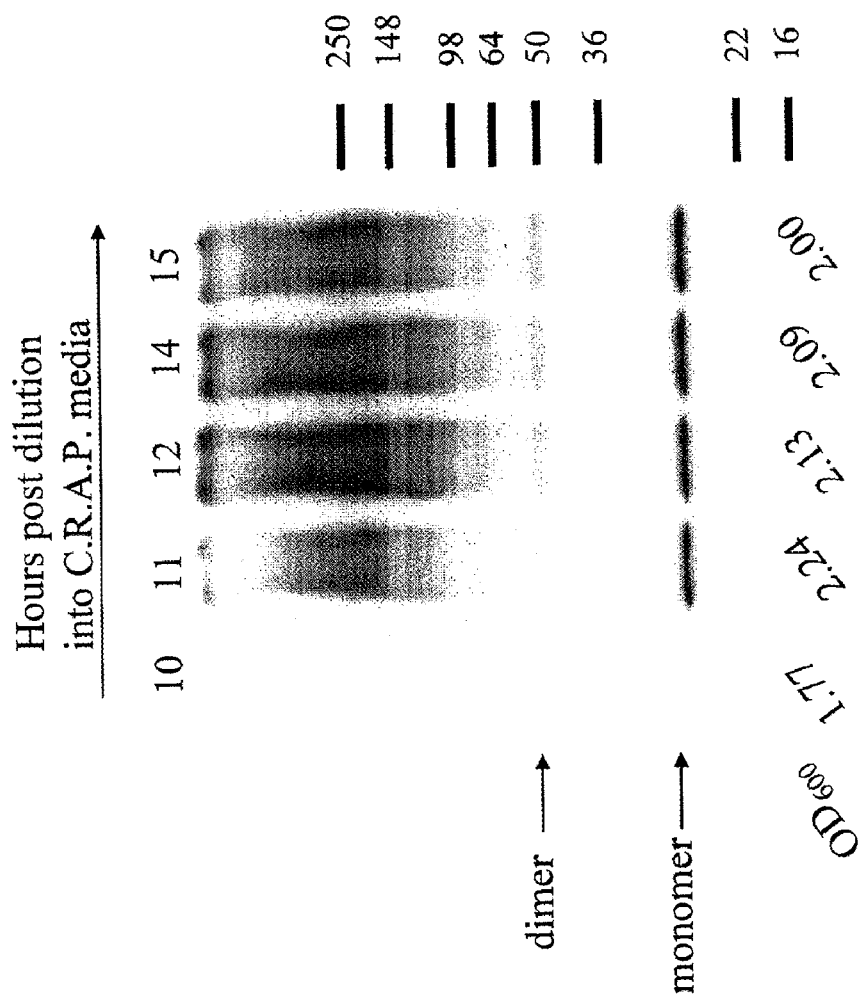

FIG. 18 is a Western blot showing a time course of MS4A4A polypeptide expression from phoA promoter induced by dilution into phosphate-limiting media.

Figure 19:
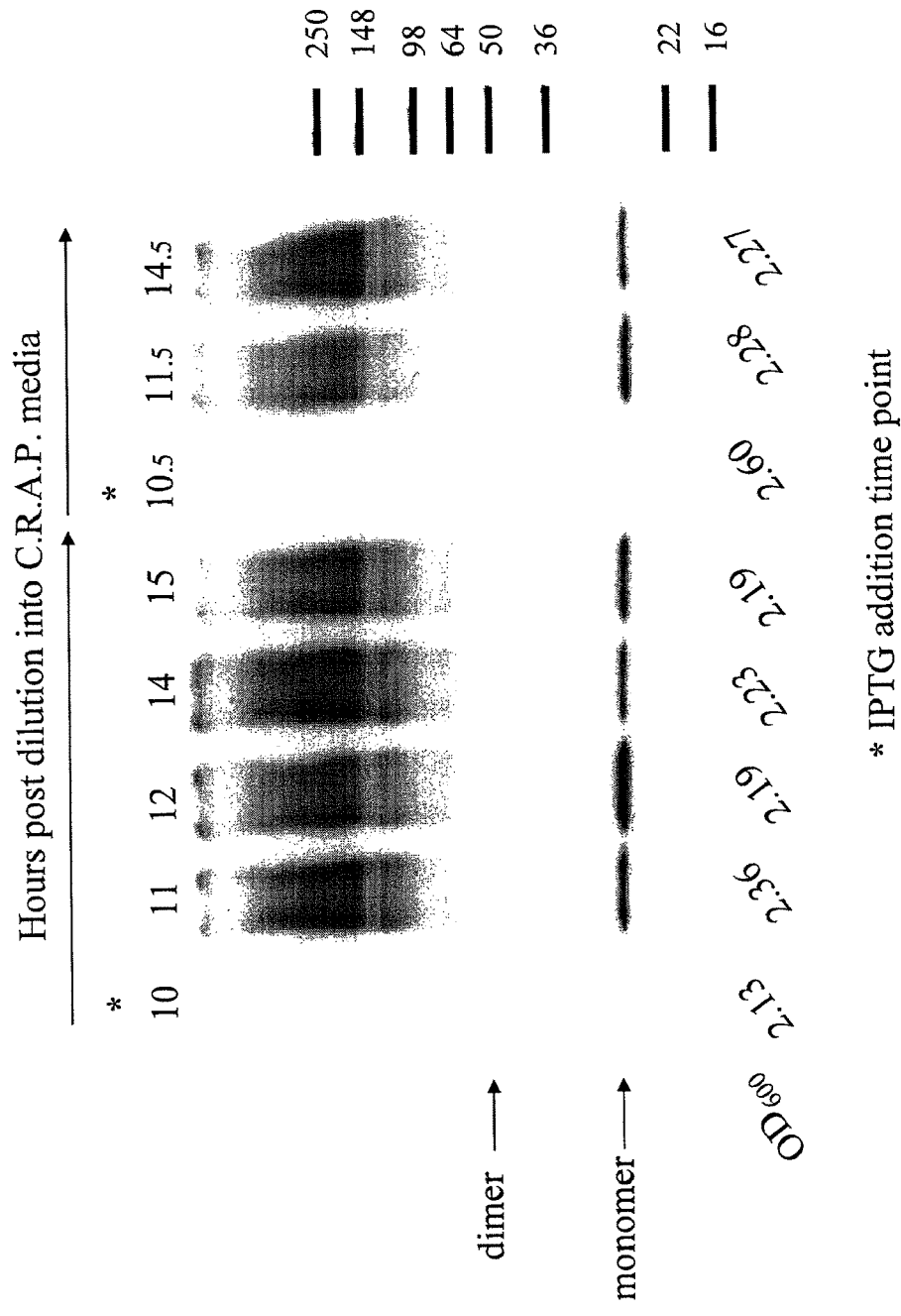

FIG. 19 is a Western blot showing a time course of MS4A4A polypeptide expression from tphac promoter induced by dilution into phosphate-limiting media and by addition of IPTG.

Figure 20:
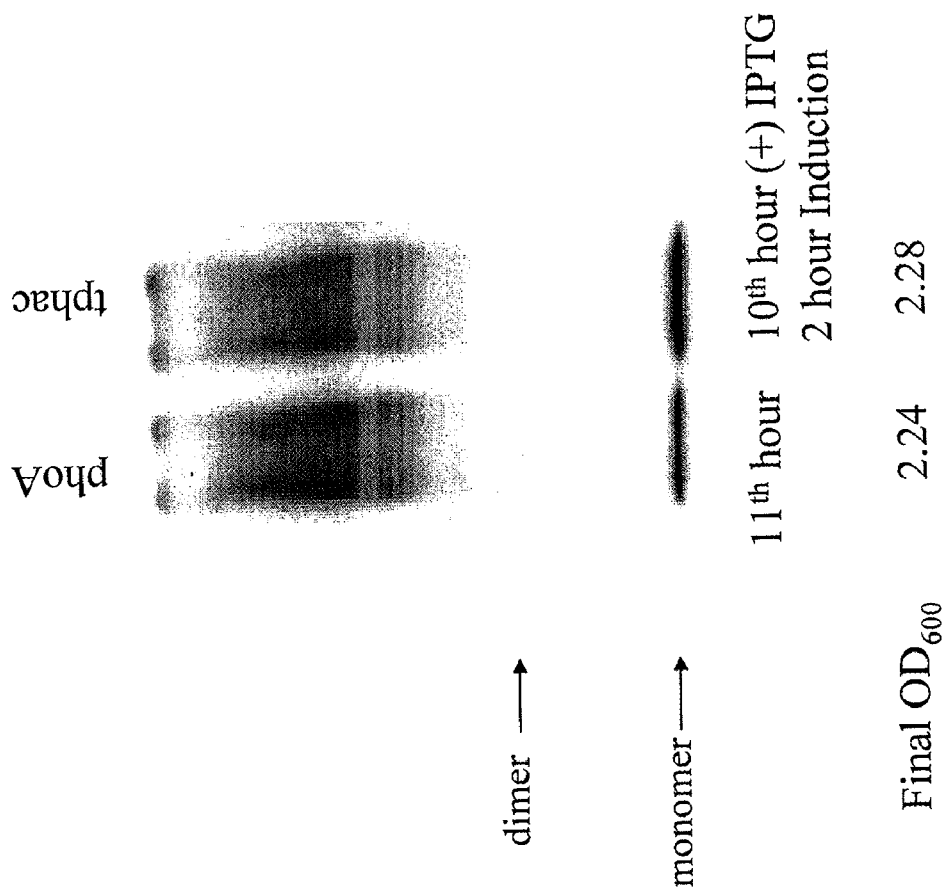

FIG. 20 is a Western blot comparing maximal expression of MS4A4A from induced phoA and tphac promoters.

Figure 21:
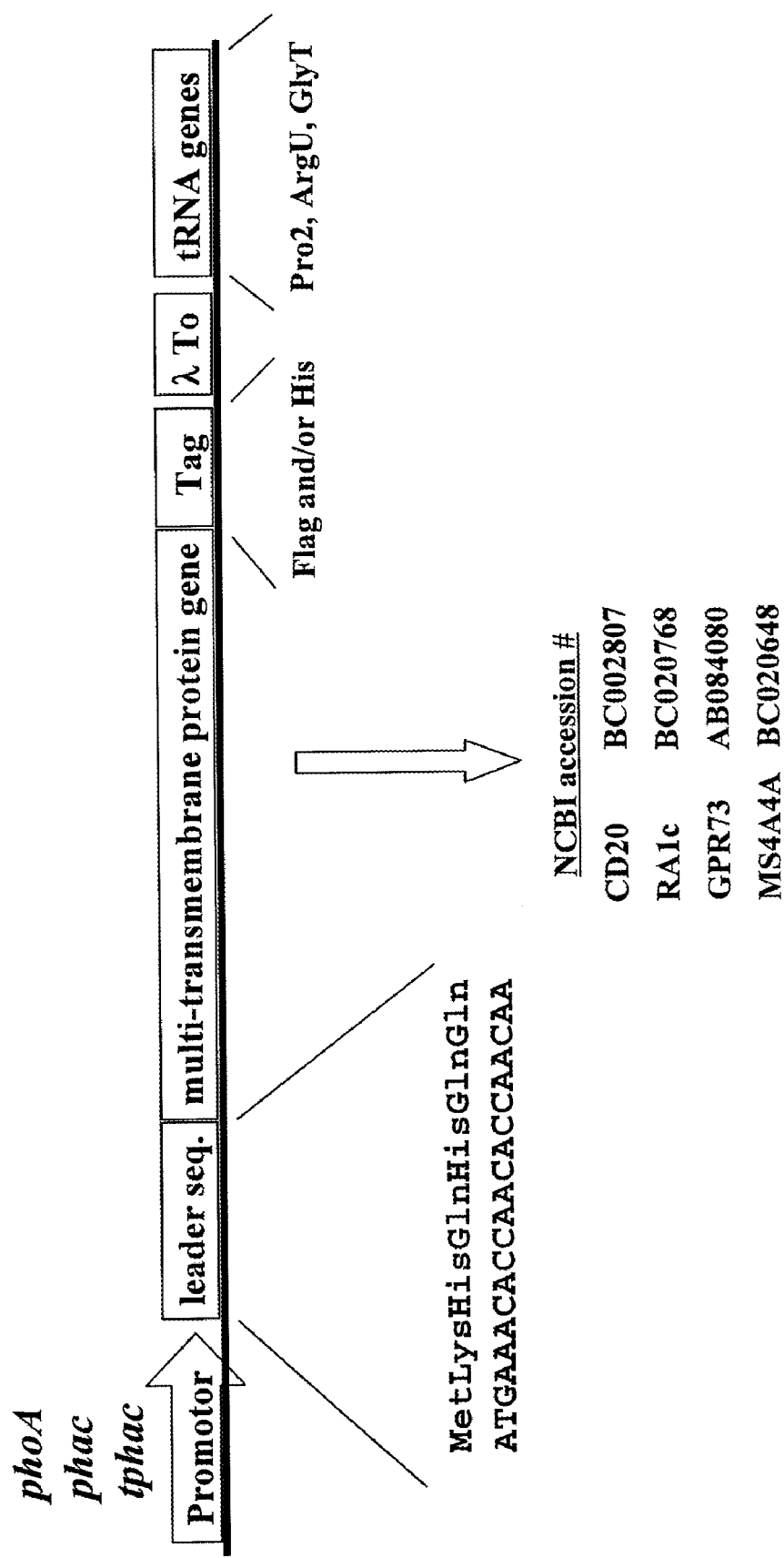

FIG. 21 is a diagrammatic representation of expression constructs for expressing multi-membrane-spanning polypeptides. Exemplary components of expression vectors are indicated.

FIG. 22 shows the amino acid sequence of the trpLE (SEQ ID NO: 25) and sLE (SEQ ID NO: 26) leaders.

Figure 23:
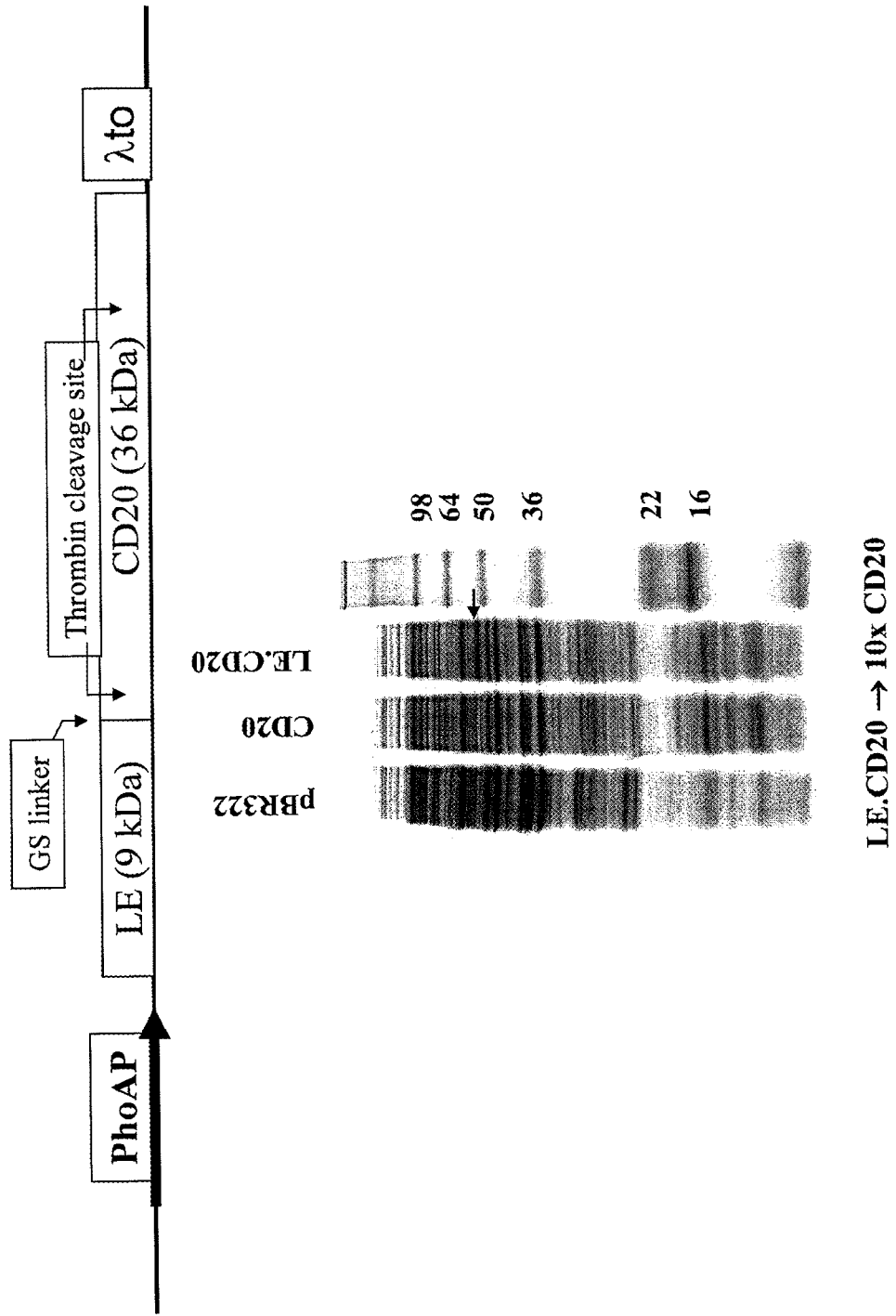

FIG. 23 shows a schematic diagram of an expression vector for expression of CD20 and a Coomassie-blue-stained gel showing expression and production of CD20 and LE.CD20 in E. coli cells.

Figure 24:
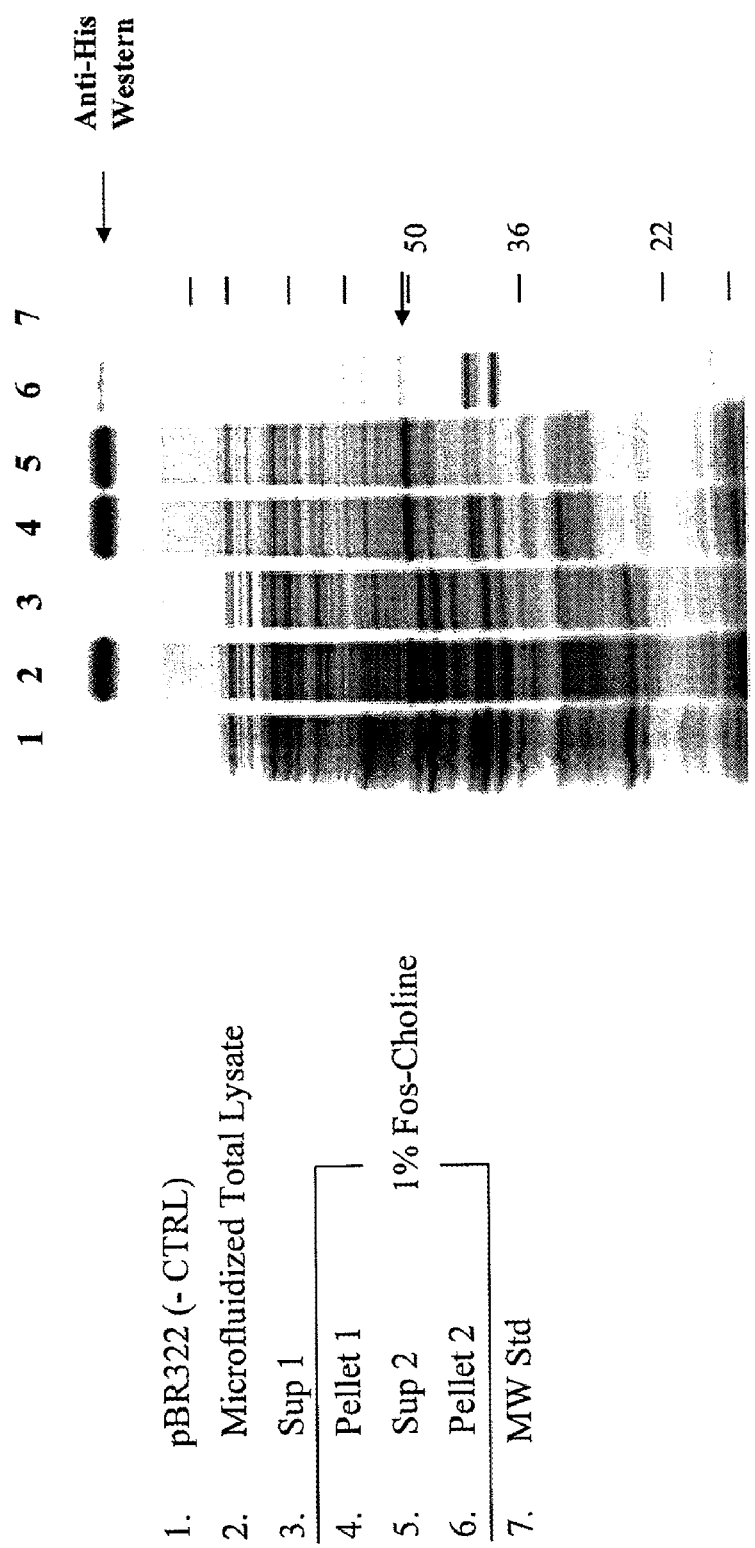

FIG. 24 shows a Western blot and a Coomassie-blue-stained gel demonstrating extraction of LE.CD20 expressed in E. coli cells.

Figure 25:
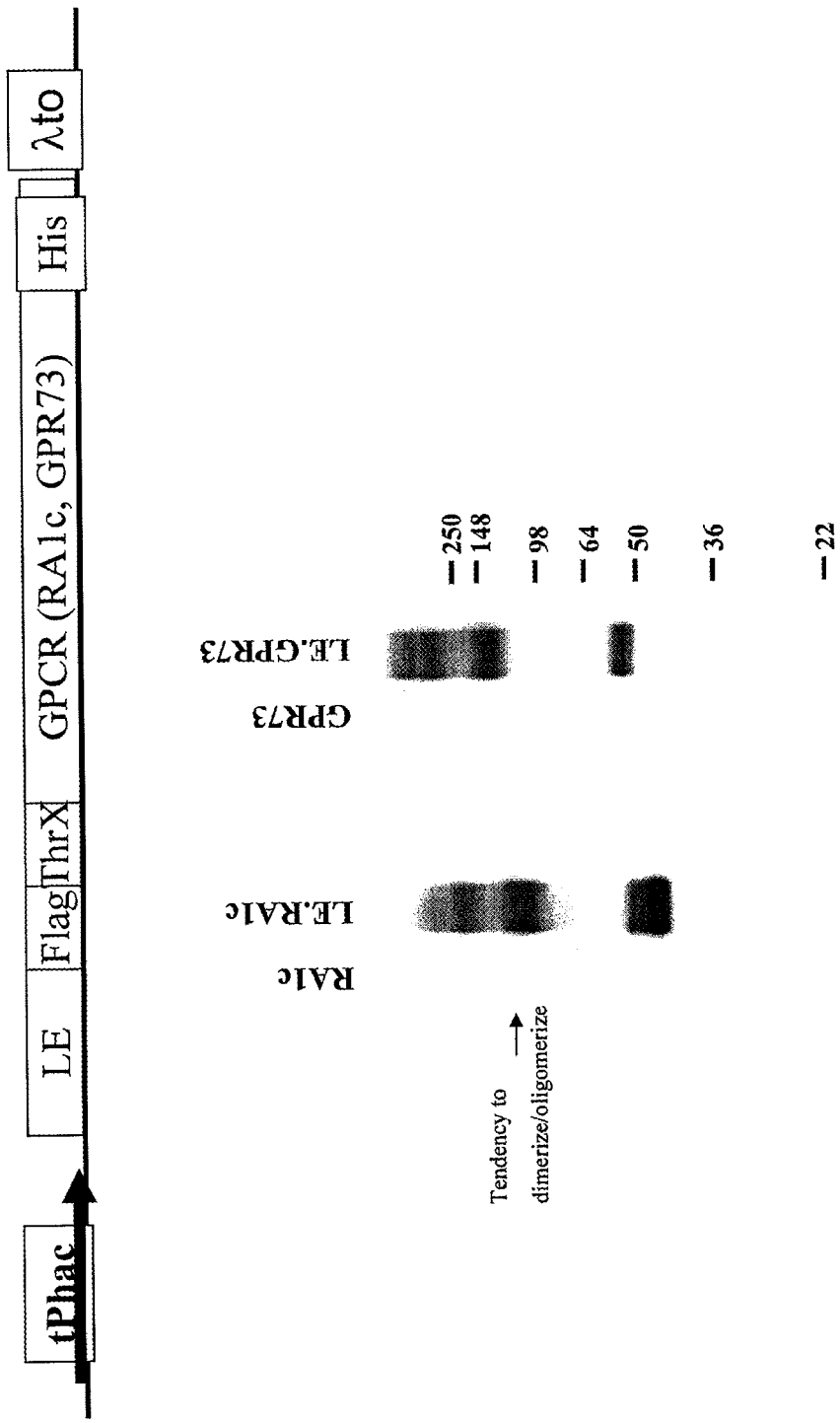

FIG. 25 shows a schematic diagram of an expression vector for expressing RA1c or GPR73 and a Western blot showing expression of LE.RA1c and LE.GPR73 as compared with control proteins.

Figure 26:
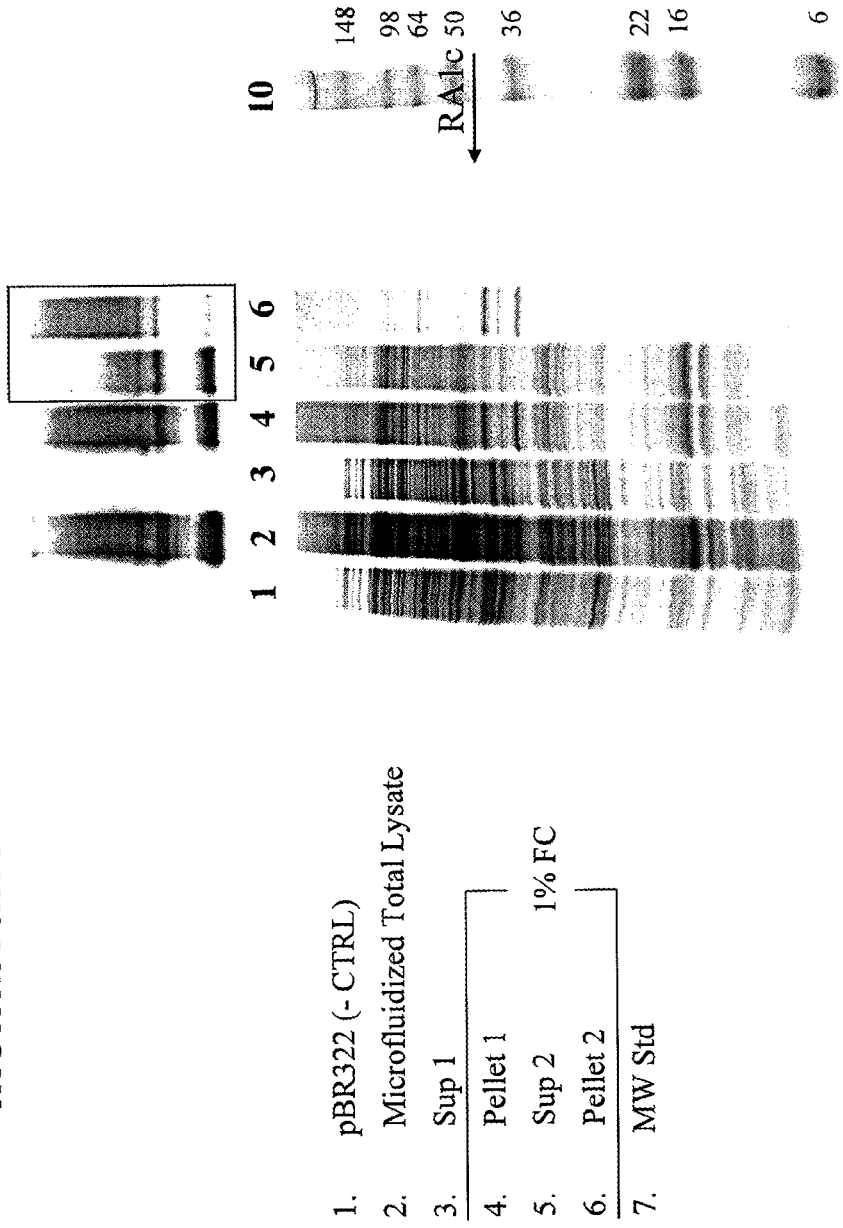

FIG. 26 is a Coomassie-blue-gel showing LE.RA1c protein expressed and extracted from E. coli cell membranes.

Figure 27:
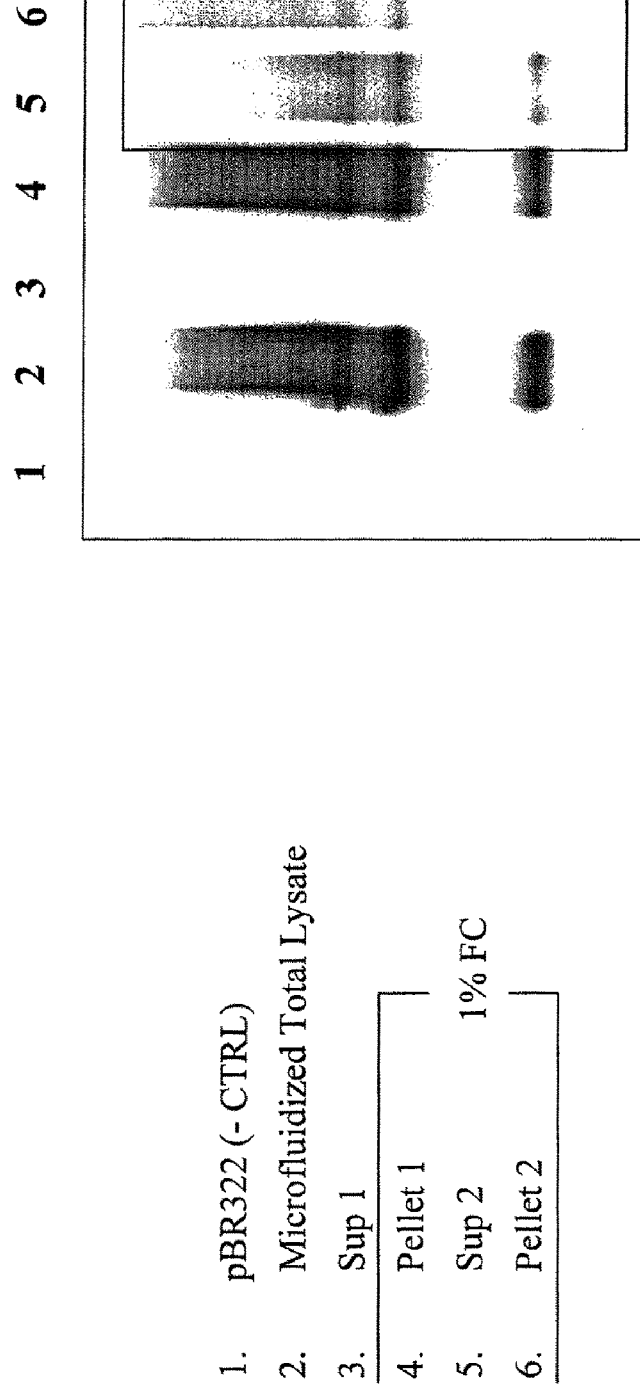

FIG. 27 is a Western blot showing LE.GPR73 extracted from E. coli cell membranes.

Figure 28:
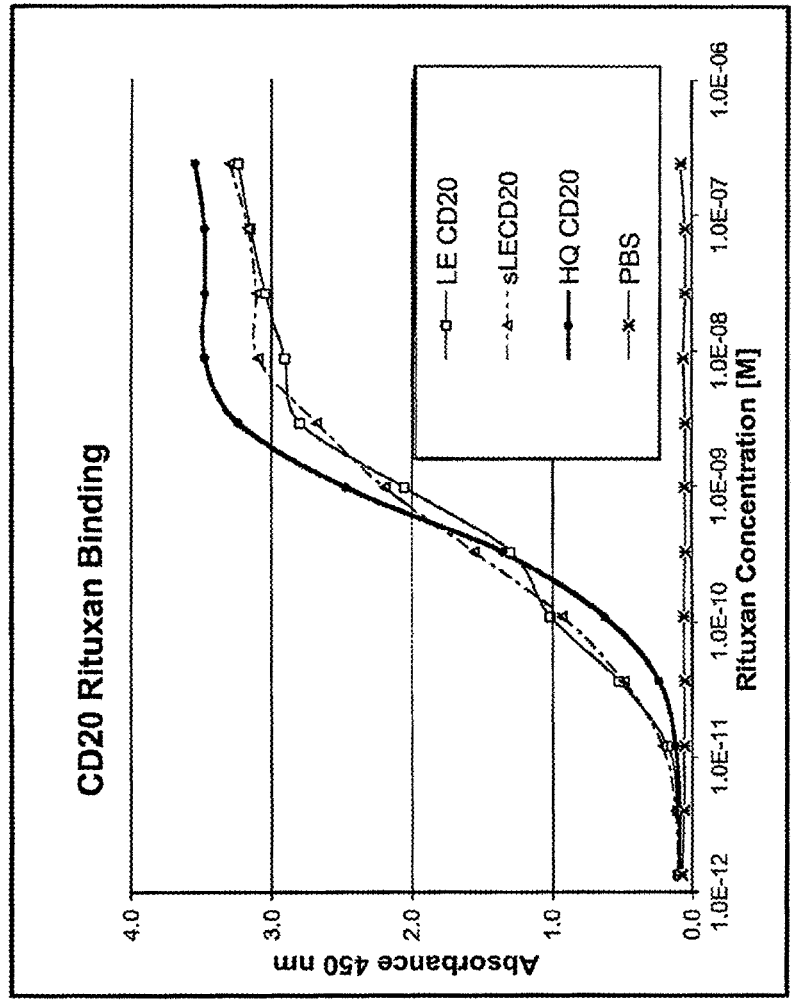

FIG. 28 is a graph showing binding of a CD20 conformation-specific antibody, rituximab, to LE.CD20 and sLECD20 expressed in E. coli and extracted as described in Example 10. For the sLE and LE samples, the LE tag was removed by digestion with thrombin, and the samples oxidized by dialysis. Open circles; hCD20 expressed with LE tag, open triangles; hCD20 expressed with sLE tag, closed circles; hCD20 expressed with HQ tag (on LE leader), and x; PBS control.

Table of Sequences

| SEQ ID NO: | Name | | Sequence Reference |
|---|---|---|---|
| 1 | human CD20 | Protein | NP_068769 Table 2, p. 53 |
| 2 | human CD20 | DNA | NCBI BC002807 |
| 3 | murine CD20 | Protein | Table 2, p. 53 |
| 4 | murine CD20 | DNA | NCBI NM_007641 |
| 5 | E. coli phoA promoter | DNA | Table 5, p. 63 |
| 6 | human C2S mutant | Protein | Table 2, p. 53 |
| 7 | MKHQHQQ | Peptide | 44, 63, 67 |
| 8 | Octa-His | Peptide | 44, Example 7 |
| 9 | human MS4A4A | DNA | NCBI BC020648 |
| 10 | human MS4A4A | Protein | NCBI AAH20648 |
| 11 | human MS4A6A | DNA | NCBI AF237908 |
| 12 | human MS4A6A | Protein | NCBI AAK37417 |
| 13 | human MS4A7 | DNA | NCBI AF237916 |
| 14 | human MS4A7 | Protein | NCBI AAK37599 |
| 15 | phac promoter | DNA | Table 5, p. 63 |
| 16 | tphac promoter | DNA | Table 5, p. 63 |

-continued

Table of Sequences

| SEQ ID NO: | Name | Sequence | Reference |
|---|---|---|---|
| 17 | Lambda transcriptional terminator | DNA | Table 5, p. 63 |
| 18 | Lac operator | DNA | Table 5, p. 63 |
| 19 | Upstream sequence with transcriptional terminator | DNA | Table 5, p. 63 |
| 20 | pho box | DNA | Table 5, p. 63 |
| 21 | human RA1c | DNA | NCBI BC020768 |
| 22 | human RA1c | Protein | NCBI AAH20768 |
| 23 | human GPR73 | DNA | NCBI AB084080 |
| 24 | human GPR73 | Protein | BAC24021 |
| 25 | LE | Protein | Example 7 |
| 26 | sLE | Protein | Example 7 |
| 27 | (M)KAIFVLKGS (TIS) | Protein | Example 7 |
| 28 | (ATG) AAA CAC CAA CAC CAA CAA (TIS) | DNA | FIG. 21 |
| 29 | AA 339-408 trpE (LE spacer) | Protein | Example 7 |
| 30 | 38 discontinuous amino acids of trpE (sLE spacer) | Protein | Example 7 |
| 31 | LVPRGS (thrombin recognition site) | Protein | Example 7 |
| 32 | DYKDDDDK (flag tag) | Protein | Example 8 |
| 33 | MGSSHHHHHH | peptide | 29 |
| 34 | ATGGGCAGCAGCCATCAT CATCATCATCAT | DNA | 29 |
| 35 | ATGAAAGCAATTTTCGTAC TGAAAGGTTCA | DNA | 30 |
| 36 | KAIFVLKGS | Protein | 3 |

DETAILED DESCRIPTION

I. Definitions

An "affinity matured" antibody is an antibody containing one or more alterations in one or more hypervariable regions that increases the binding affinity of the antibody for a target antigen. Affinity matured antibodies can have nanomolar or picomolar affinities for the target antigen. Affinity matured antibodies can be produced by methods known in the art, such as for example, VH and VL domain shuffling (Marks et al., 1992, Bio/Technology, 10:779-783), random mutagenesis of CDR and/or framework residues (Barbas et al., 1994, Proc. Nat. Acad. Sci. USA, 91:3809-3813; Scier et al., 1995, Gene, 169: 147-155; Yelton et al., 1995, J. Immunol., 155: 1994-2004; Jackson et al., 1995, J. Immunol., 154: 3310-3319; and Hawkins et al., 1992, J. Mol. Biol., 226: 889-896), and phage display techniques (Lowman et al., 1991, Biochemistry, 30: 10832-10838; Hawkins et al., 1992, J. Mol. Biol., 226, 889-896; U.S. Pat. No. 6,172,213).

The terms "antibody" and "immunoglobulin" are used interchangeably in the broadest sense and include monoclonal antibodies (full-length or intact monoclonal antibodies), polyclonal antibodies, humanized, multivalent antibodies, multispecific antibodies (e.g., bispecific antibodies so long as they exhibit the desired biological activity), and antibody fragments.

"Antibody fragments" contain a portion of an intact antibody, generally the antigen binding or variable region of the intact antibody. Examples of antibody fragments include, but are not limited to Fab fragments, Fab' fragments, Fd' fragment, Fv fragment, Fd fragment, F(ab')$_2$ fragment, dAb fragment, hingeless antibodies, single chain antibodies, diabodies, single arm antigen binding molecules (containing a light chain, a heavy chain and a N-terminally truncated heavy chain constant region sufficient to form a Fc region capable of increasing the half life of the single arm antigen binding molecule), and linear antibodies.

The term "monoclonal antibody" as used herein refers to an antibody obtained from a population of substantially homogeneous antibodies, i.e., the individual antibodies comprising the population are essentially identical except for variants that may arise during production of the antibody.

The term "monoclonal antibodies" specifically includes "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., 1984, *Proc. Natl. Acad. Sci. USA*, 81:6851-6855).

The term "biological sample" refers to a body sample from any animal, such as a mammal, for example, a human. The biological sample can be obtained from vascular, diabetic, or cancer patients, for example. A biological sample can be, for example, biological fluids such as serum, plasma, vitreous fluid, lymph fluid, synovial fluid, follicular fluid, seminal fluid, amniotic fluid, milk, whole blood, urine, cerebro-spinal fluid, saliva, sputum, tears, perspiration, mucus, and tissue culture medium, as well as tissue extracts such as homogenized tissue, cellular extracts, or whole cells or tissue. The biological sample can be, for example, serum, plasma, or urine.

As used herein, "buffer" refers to a buffered solution that resists changes in pH by the action of its acid-base conjugate components.

The term "CD20 mutant" or "CD20 variant" refers to a CD20 polypeptide that contains an amino acid sequence that differs from a reference CD20 amino acid sequence or is encoded by a nucleic acid sequence that differs from a reference CD20 nucleic acid sequence. CD20 mutants include a change of amino acid sequence that can be produced by substitution, deletion, or insertion of one or more amino acid in the reference sequence.

The term "capture reagent" refers to a reagent capable of binding and capturing a target molecule in a sample. The capture reagent-target molecule complex can be separated from the rest of the sample under suitable conditions. The capture reagent can be immobilized or immobilizable. In a sandwich immunoassay, for example, the capture reagent can be an antibody or a mixture of different antibodies against a target antigen.

The term "detergent" refers to an agent that may comprise salts of long-chain aliphatic bases or acids, or hydrophilic moieties such as sugars, and that possess both hydrophilic and hydrophobic properties. Having both hydrophilic and hydrophobic properties, the detergent can exert particular effects. As used herein, detergents have the ability to disrupt cellular membranes and solubilize polypeptides.

The term "detectable antibody" refers to an antibody that is capable of being detected either directly through a label amplified by a detection means, or indirectly through, e.g., another antibody that is labeled. For direct labeling, the antibody is typically conjugated to a moiety that is detectable by some means. The antibody typically can be labeled with a detectable label including, but not limited to, a fluorescent label, a radioisotope, or an enzyme-substrate label. The label may be indirectly conjugated with the antibody. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody).

The term "detection reagent" refers to a moiety or agent used to detect the presence of a label and includes detection agents that amplify the immobilized label such as label captured onto a microtiter plate. The detection means can be, for example, a detection agent such as avidin or streptavidin labeled with a fluorescent or chromophoric moiety.

The term "expression tag" refers to a peptide sequence or label fused to the N or C-terminus of a mature polypeptide or conjugated to specific residues in the mature polypeptide that provides one means to identify and/or isolate an expressed polypeptide. The expression tag may be encoded as a component of a vector, or comprise a portion of a polypeptide coding sequence inserted into an expression vector. Examples of expression tags include, but are not limited to, poly-His tags (U.S. Pat. No. 4,569,794), FLAG, myc, biotin, avidin, and the like. Such tags are well known and commercially available (See, for example, Qiagen, Valencia, Calif.).

The term "heterologous" refers to elements occurring where they are not normally found. For example, a promoter may be linked to a heterologous nucleic acid sequence, e.g., a sequence that is not normally found operably linked to the promoter. When used herein to describe a promoter element, heterologous means a promoter element that differs from that normally found operably linked to the native promoter, either in sequence, species, or number. For example, a heterologous control element in a promoter sequence may be a control/regulatory element of a different promoter added to enhance promoter control, or an additional control element of the same promoter.

As used herein, the phrase "induce expression" means to increase the amount or rate of transcription and/or translation from specific genes by exposure of the cells containing such genes to an effector or inducer reagent or condition.

An "inducer" is a chemical or physical agent which, when applied to a population of cells, will increase the amount of transcription from specific genes. These are usually small molecules whose effects are specific to particular operons or groups of genes, and can include sugars, phosphate, alcohol, metal ions, hormones, heat, cold, and the like. For example, isopropyl (beta)-D-thiogalactopyranoside (IPTG) and lactose are inducers of the tacII promoter, and L-arabinose is a suitable inducer of the arabinose promoter. A pho gene promoter, such as phoA (Chang et al., 1987, *Gene*, 55: 189-196) and pho5, is inducible by low phosphate concentrations in the medium.

A reagent may be "immobilized" on or in a support by forming a covalent bond between a functional group of the reagent and a reactive group on the surface of the solid phase. In other embodiments, the reagent is "immobilized" on the solid phase by adsorption and ionic binding or may be entrapped in the solid phase, e.g., within cells or lattice type polymers or microcapsules (See Holenberg et al., in Enzymes as Drugs, John Wiley & Sons NY (1981), pages 396-411). The reagent should essentially retain its ability to bind to and/or modify the polypeptide of interest once immobilized to the solid phase.

The term "isolated," when used to describe the various polypeptides disclosed herein, means a polypeptide that has been identified and separated and/or recovered from a component of its natural environment. The isolated polypeptide is free of association with at least one component with which it is naturally associated. Contaminant components of its natural environment are materials that would typically interfere with diagnostic or therapeutic uses for the polypeptide and may include enzymes, and other proteinaceous or non-proteinaceous solutes. An isolated polypeptide includes polypeptide in situ within recombinant cells. Ordinarily, however, an isolated polypeptide will be prepared by at least one purification step.

"Isolated CD20," as used herein, refers to a CD20 protein that is free of cells or membranes, and can be, for example, in soluble form in a detergent solution.

An "isolated" nucleic acid molecule or polynucleotide is a nucleic acid molecule that is identified and separated from at least one contaminant nucleic acid molecule with which it is ordinarily associated in the natural source. The isolated nucleic can be, for example, free of association with all components with which it is naturally associated. An isolated nucleic acid molecule is other than in the form or setting in which it is found in nature.

"IPTG" is the compound "isopropyl (beta)-D-thiogalactopyranoside", and is used herein as an inducer of lac operon. IPTG binds to a lac repressor effecting a conformational change in the lac repressor that results in dissociation of the lac repressor from the lac operator. With the lac repressor unbound, an operably linked promoter is activated and downstream genes are transcribed.

The term "lac operator" refers to a nucleic acid sequence that can be bound by a lac repressor, lad, as described, for example, in Jacob et al., 1961, *J. Mol. Biol.*, 3: 318-356. A promoter is not activated when the lac repressor is bound to the lac operator. When the lac repressor is induced to dissociate from the operator, the promoter is activated.

The term "leader sequence" refers to a nucleic acid sequence positioned upstream of a coding sequence of interest. Leader sequences described herein contain specific sequences known to bind efficiently to ribosomes, thus delivering a greater efficiency of translation initiation of some polynucleotides. As described herein, a leader sequence contains a translation initiation sequence and a spacer sequence for enhancing translation elongation as defined herein.

The term "low phosphate media" or "phosphate-limiting media" as used herein, refers to media containing a low concentration of phosphate in solution. For example, the phoA promoter turns on when the medium concentration of phosphate drops to about 4 μM (micromolar) or less. However, phosphate-limiting media is designed to contain more than 4 μM (micromolar) of phosphate to give cells a chance to grow before the promoter turns on. Examples of phosphate-limiting media include, but are not limited to C.R.A.P. media described in Simmons et al., 2002, *J. Immunol. Methods*, 263: 133-147 (containing about 1.9 M initial phosphate concentration due to trace contaminants from yeast extract and other sources) and media as described in Chang et al., 1987, *Gene* 55:189-196.

As used herein, the term "mammal" refers to any animal classified as a mammal, including humans, domestic and farm animals, and zoo, sports, or pet animals, such as dogs, horses, cats, cows, etc. The mammal can be, for example, human.

The term "MS4A polypeptide" refers to a polypeptide encoded by a gene of the Membrane-Spanning 4-domains, subfamily A (MS4A) gene family. See, for example, Ishibashi et al., 2001, *Gene*, 264:87-93. The MS4A polypeptide can be naturally occurring or a variant of a naturally occurring MS4A polypeptide. Members of the MS4A gene family have polypeptides with structural similarities. Each spans the cell membrane four times, both N- and C-termini are located on the cytoplasmic side of the cellular membrane, and both contain an extracellular loop approximately 50 amino acids in length. MS4A polypeptides include CD20, high-affinity IgE receptor β chain, HTm4, MS4A4A, MS4A7, and the like. The term also includes variants and isoforms of the polypeptides encoded by MS4A genes. This gene family is conserved in mammals, and "MS4A polypeptide" includes human, mouse, rat, and the like polypeptides.

A "variant" of MS4A polypeptide refers to an MS4A polypeptide that contains an amino acid sequence that differs from a reference sequence or is encoded by a nucleic acid sequence that differs from a reference sequence. The reference sequence can be a full-length native MS4A polypeptide sequence, an extracellular domain of a MS4A polypeptide, or any other fragment of a full-length MS4A polypeptide sequence. In some embodiments, the reference sequence is a nucleic acid sequence or amino acid sequence of a naturally occurring CD20, such as for example SEQ ID NO: 1 (amino acid sequence) or SEQ ID NO: 2 (nucleic acid sequence). A MS4A polypeptide variant generally has at least about 80% amino acid sequence identity with the reference sequence.

MS4A polypeptide variants include "naturally occurring" variants, including allelic variants, as well as variants that are prepared by alteration of one more nucleotides or amino acids. A variant polypeptide can be prepared by modifying a nucleic acid sequence or an amino acid sequence of a MS4A polypeptide. For example, the variant can be prepared by addition, substitution, and/or deletion of nucleotides or amino acids. A variant MS4A polypeptide useful in the methods of the invention can have, for example, at least 80%, at least about 85%, at least about 90%, at least 91%, at least 92%, at least 93%, at least 94%, at least 95%, at least 96%, at least 97%, at least 98%, at least 99% sequence identity to a MS4A reference sequence, for example, to a reference sequence for human CD20 such as SEQ ID NO: 1.

The term "membrane spanning protein" or "transmembrane protein" refers to a polypeptide that comprises one or more segments embedded in the phospholipid bilayer of a cellular membrane. A membrane spanning protein may further comprise an intracellular domain, an extracellular domain, or both. The cellular membrane may be a membrane of bacteria, yeast, mammalian cells, and the like.

The term "membrane spanning domain" or "transmembrane domain" refers to a portion of a membrane spanning protein that is embedded in the phospholipid bilayer of a cellular membrane.

The term "native conformation" refers to a polypeptide's three-dimensional shape in its natural state. Native conformation can refer to a polypeptide's tertiary or quaternary structure. As used herein, "native conformation" of a solubilized transmembrane polypeptide is sufficient to permit the solubilized polypeptide to be useful as an immunogen to produce antibodies that recognize the transmembrane polypeptide in a cell or useful as a binding ligand to bind antibodies that recognize the transmembrane polypeptide in a cell.

The term "non-ionic" refers to a molecule that does not ionize in solution, i.e., is "ionically" inert.

A nucleic acid sequence or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading frame. Linking can be accomplished by ligation at convenient restriction sites. If such sites do not exist, synthetic oligonucleotide adaptors or linkers are used in accordance with conventional practice.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Percent (%) amino acid sequence identity" with respect to the polypeptides identified herein is defined as the percentage of amino acid residues in a candidate sequence that are identical with the amino acid residues in the reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. The ALIGN-2 program is publicly available through Genentech, Inc., South San Francisco, Calif.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y, where X is the number of amino acid residues scored as identical matches by the sequence alignment program in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"Percent (%) nucleic acid sequence identity" is defined as the percentage of nucleotides in a candidate sequence that are identical with the nucleotides in a reference polypeptide-encoding nucleic acid sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z, where W is the number of nucleotides scored as identical matches by the sequence alignment program in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

The term "phoA promoter" refers to a promoter of the structural gene for alkaline phosphatase, phoA. A variety of bacteria, particularly Enterobacteriaceae, possess a phoA gene and phoA promoter. The $E.$ $coli$ phoA promoter is exemplified herein and has the nucleic acid sequence of SEQ ID NO: 5.

The term "mutant promoter" or "variant promoter" refers to a promoter having a nucleic acid sequence that differs from a reference sequence. For example, the mutant phac and tphac promoters differ from the phoA reference promoter, as shown in Table 5. A change in the nucleic acid sequence of a promoter can result from substitution, deletion, or insertion of one or more nucleic acid.

The term "phoA" refers to a gene encoding an alkaline phosphatase metalloenzyme. In $E.$ $coli$, the phoA enzyme is part of a phosphate regulon in which phoA expression is upregulated more than 100-fold upon starvation of inorganic phosphate (See, for example, Kriakov et al., 2003, $J.$ $Bacteriol.$, 185: 4983-4991). Bacterial species other than $E.$ $coli$ possess phoA homologues (for example, $Klebsiella$ spp., $Shigella$ spp., $Mycobacterium$ $smegmatis$).

The term "poly-His" generally refers to amino acid residues comprising multiple histidine residues, generally 6-10 histidine residues. Multiple histidine residues are often used as an expression tag, thus termed a "poly-His tag" (See U.S. Pat. No. 4,569,794). Poly-his tags can be used to detect and/or purify polypeptides, for example by applying a sample to an affinity column, such as a nickel column.

As used herein, "polypeptide" refers generally to peptides and proteins having more than about ten amino acids. The polypeptides can be "exogenous," meaning that they are "heterologous," i.e., foreign to the host cell being utilized, such as human polypeptide produced by a bacterial cell.

"Primate" is construed to mean any of an order of mammals comprising humans, apes, monkeys, and related forms, such as lemurs and tarsiers.

"Purifying" means increasing the degree of purity, for example, of a membrane-spanning polypeptide in a composition by removing (completely or partially) at least one contaminant from the composition. A "purification step" may be part of an overall purification process resulting in an "essentially pure" composition. An essentially pure composition contains at least about 90% by weight of the polypeptide of interest, based on total weight of the composition, and can contain at least about 95% by weight.

The term "rare codons" or "minor tRNAs" refers to specific codons or tRNAs that are low in abundance in a particular cell type. See for example, Dong et al., 1996, $J.$ $Mol.$ $Biol.$, 260: 649-663, describing tRNA abundance and codon usage in $E.$ $coli$ cells.

The term "regulatory element" or "control element" refers to DNA sequences controlling initiation of transcription. Examples of control or regulatory elements include, but are not limited to, a TATA box, operators, enhancers, and the like. Regulatory or control elements include negative control elements and positive control elements. A negative control element is one that is removed for transcription activation. Many such negative control elements are known, for example operator/repressor systems. For example, binding of IPTG to the lac repressor dissociates from the lac operator to activate and permit transcription. Other negative elements include the *E. coli* trp and lambda systems. A positive control element is one that is added for transcription activation. Many such positive control elements are known, including the *E. coli* pho Box and variations of the pho Box that bind phoB, the MalT DNA binding site, the AraC DNA binding site, and the like. For example, binding of phoB to the pho box of the phoA promoter induces activation of the promoter.

Promoters naturally containing both positive and negative regulatory elements are rare. The metE promoter is one example. See, for example, Neidhardt, Ed., 1996, *Escherishia coli and Salmonella*, Second Ed., pages 1300-1309. Descriptions of known positive and negative control elements can be found, for example, in this reference. In some embodiments, the promoter has both positive and negative control elements that provide for direct control of basal expression. Positioning of a positive or negative control element within or adjacent to the promoter to achieve added regulation of the promoter is known, and is described, for example, in *Escherichia coli and Salmonella* (Supra) at pages 1232-1245.

The terms "rituximab" or "RITUXAN®" herein refer to the genetically engineered chimeric murine/human monoclonal antibody directed against the CD20 antigen and designated "C2B8" in U.S. Pat. No. 5,736,137, expressly incorporated herein by reference. The antibody is an $IgG_1$ kappa immunoglobulin containing murine light and heavy chain variable region sequences and human constant region sequences. Rituximab has a binding affinity for the CD20 antigen of approximately 8.0 nM.

The term "solubilizing" refers to dissolving a molecule in a solution. In an embodiment of the invention, a recombinant transmembrane polypeptide expressed in a bacterial host is solubilized in a non-ionic or zwitterionic detergent.

The term "spacer sequence" refers to a sequence of polynucleotides encoding an amino acid sequence positioned between the translation initiation sequence and the first transmembrane domain.

The term "tightly controlled promoter" or "tightly regulated promoter" refers to a promoter exhibiting little or no basal expression of operably linked genes. A tightly controller or regulated promoter activates expression under specifically defined, controlled conditions.

The term "transcriptional terminator" refers to nucleic acid sequence that signals RNA polymerase to terminate transcription. Transcriptional terminators are well known and include, but are not limited to, the lambda λ0 (tao zero) transcriptional terminator (SEQ ID NO: 17), *E. coli* rrnB1 T1 and rrnB2 T2 transcriptional terminators, and the strong His operon terminator, for example.

The term "translation initiation enhancer sequence or "translation initiation sequence" (TIS) as used herein, refers to a nucleic acid sequence that can determine a site and efficiency of initiation of translation of a gene (See, for example, McCarthy et al., 1990, *Trends in Genetics*, 6: 78-85). A "translation initiation sequence" may also be referred to as a translation initiation region (TIR).

The term "zwitterionic" or "dipolar" refers to molecules having charged groups of opposite polarity.

II. Modes for Carrying Out the Invention

A. Membrane-Spanning Polypeptides

Membrane-spanning polypeptides, such as CD20, MS4A4A, RA1c, GPR73, and the like, are potential targets for therapeutics in the treatment of diseases and disorders, such as cancer. CD20 is the target for the chimeric antibody rituximab (RITUXAN®), a lead therapeutic in the treatment of non-Hodgkins lymphoma. Rituximab recognizes CD20 in a native conformation expressed on B cells. Binding of rituximab is dependent on a loop structure between the third and fourth transmembrane helical region of CD20 that contains cysteine residues at positions 167 and 183 (see FIG. 1).

A significant hurdle in the development of therapeutics that target membrane-spanning polypeptides, for example CD20, is the inability to produce useful isolated and purified recombinant or naturally occurring membrane-spanning polypeptides. For example, to be useful as an immunogen or binding antigen, the isolated and purified polypeptide should have sufficient "native" conformation to be recognized by a binding partner. The polypeptide retains sufficient native conformation to be recognized by a ligand whose binding is dependent upon a structural feature present in the native conformation of the polypeptide. The present invention provides vectors comprising novel promoters for producing membrane-spanning polypeptides in a bacterial host, methods of producing membrane-spanning polypeptides in a bacterial host, and methods of isolating membrane-spanning polypeptides from bacterial hosts. The methods of the invention provide membrane-spanning polypeptides at high yields and with sufficient "native" conformation to be useful, for example as immunogens and binding antigens.

A membrane-spanning polypeptide contains one or more of membrane-spanning domains, and may have 1, 2, 3, 4, 5, 6, 7, 8, 9, 10, 11, 12, or 24 or more such domains. In an embodiment, the membrane-spanning polypeptide has at least four membrane-spanning domains. In another embodiment, the membrane-spanning polypeptide has 7 membrane-spanning domains, such as the EG-VEGF receptor, GPR73 and the RA1c receptor. Membrane-spanning polypeptides having four membrane-spanning domains include, for example, members of the MS4 family of polypeptides. In another embodiment, the membrane-spanning polypeptide is a CD20 polypeptide or variant thereof.

The following description uses CD20 as one example of the membrane-spanning polypeptides useful in the invention. Additional polypeptides are similarly useful in the methods of expression and solubilization described herein, including those disclosed in the Examples below as well as other non-disclosed membrane-spanning polypeptides.

1. CD20

CD20 is a phosphoprotein of approximately 35 kDa, found on the surface of greater than 90% of B cells from peripheral blood or lymphoid organs. Other names for CD20 in the literature include "B-lymphocyte-restricted antigen" and "Bp35". CD20 is described in Clark et al., 1985, *Proc. Natl. Acad. Sci. USA*, 82: 1766-1770, for example. CD20 is expressed during early pre-B cell development and remains until plasma cell differentiation. B-cell activation results in an additional increase in CD20 expression (Valentine et al., 1987, *Proc. Natl. Acad. Sci. USA*, 84: 8085-8097). CD20 is not expressed in plasma cells. CD20 is present on normal as well as malignant B cells.

The present invention provides isolated mammalian CD20 that is free of cells and cellular membranes and retains sufficient native conformation so as to bind rituximab or an antigen-binding fragment thereof. Examples of mammalian CD20 include, but are not limited to, human CD20 and murine CD20 shown below in Table 2 as SEQ ID NOs: 1 and 3. Reference nucleic acid sequences encoding human CD20 (NCBI Accession No. BC002807) and murine CD20 (NCBI Accession No. NM_007641) are found in the NCBI database. Human CD20 exists in various phosphorylation states in B cells, for example, but there are no known splice variants.

Figure 1:
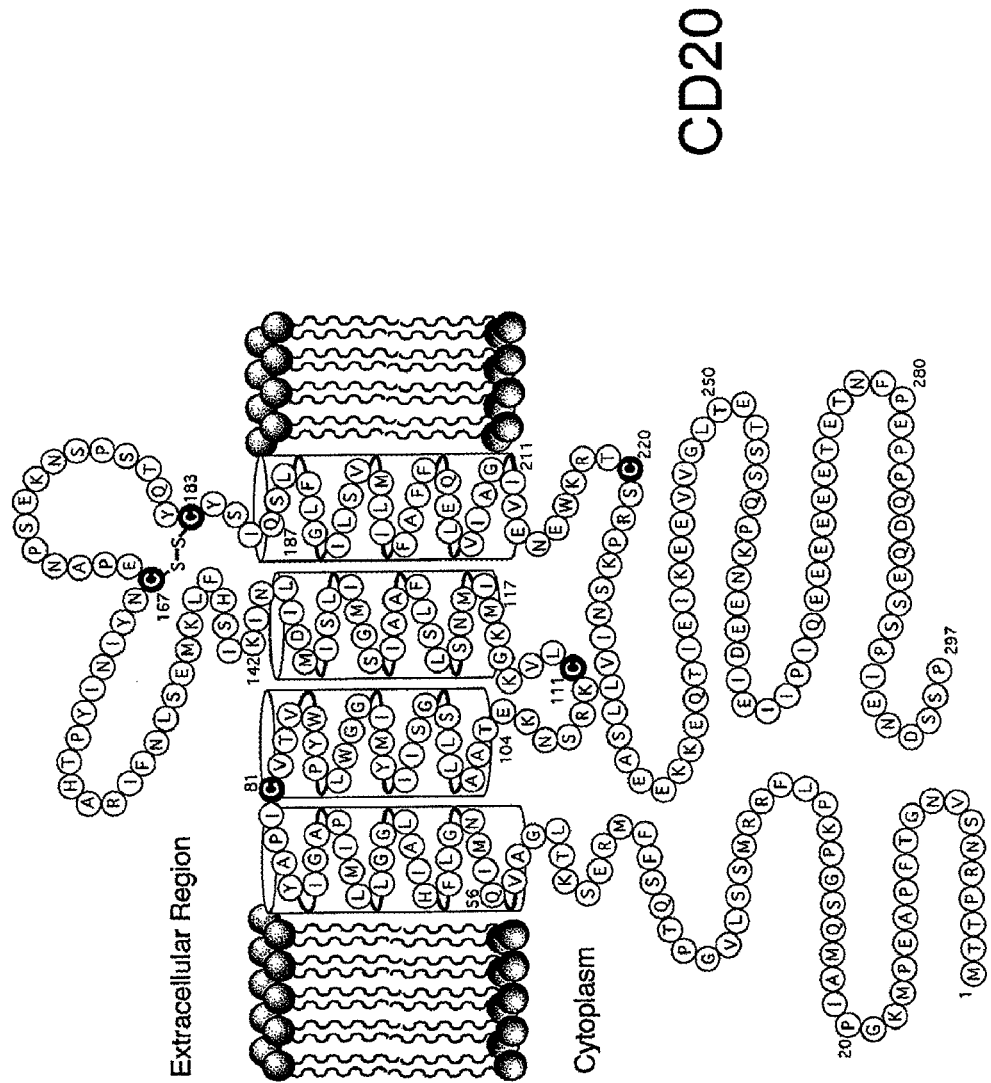
FIG. 1 is a diagrammatic representation of CD20 presented in a B cell membrane. Sequence and proposed overall topology of CD20 are presented in relation to the cell surface membrane.

As shown diagrammatically in FIG. 1, CD20 is a tetra-spanning membrane polypeptide with both termini on the cytoplasm side of the cell membrane. A first extracellular loop (loop A) is formed between the first and second membrane-spanning domains and a second extracellular loop (loop B) is formed between the third and fourth membrane-spanning domains. Loop B is larger than loop A. Loop A does not protrude extensively from the membrane-spanning domains. Loop B is about 46 amino acids in length and protrudes extensively from the membrane-spanning domains. Loop B extends from about Asn140 to about Ser185 and contains a disulfide bond between Cys167 and Cys183. Binding of CD20 by rituximab is dependent on loop B. See, for example, Polyak and Deans, 2002, *Blood* 99:3256-3262.

CD20 polypeptides of the invention are soluble in non-ionic or zwitterionic detergent and retain sufficient "native" loop B structure in the detergent such that rituximab or an antigen binding rituximab fragment can bind the polypeptide. In an embodiment, the loop formed between the third and fourth transmembrane-spanning domains is retained in the isolated CD20. The loop contains a disulfide bond between Cys167 and Cys183, and includes, for example, residues I164 through Y184 of CD20, as shown in FIG. 1. The loop can contain, for example, about 40 to about 60 amino acids, and can be about 40 to about 50 amino acids in length, about 45 to about 50 amino acids in length, or about 46 amino acids in length. In an embodiment, the loop extends from Asn140 to Ser185 and contains a disulfide bond between Cys167 and Cys183. In one embodiment, the loop can be bound by rituximab or by an antigen-binding fragment thereof.

2. Variant Membrane-Spanning Polypeptides

The present invention also provides variants of membrane-spanning polypeptides such as CD20 that may be naturally occurring or recombinant. Variants include, for example, deletions, insertions, or substitutions of amino acid residues in a mammalian reference sequence.

A variant membrane-spanning polypeptide comprises an amino acid sequence having at least about 80%, 85%, 90%, 91%, 92%, 93%, 94%, 95%, 96%, 97%, 98%, 99%, or greater identity to a mammalian reference sequence. For example, a CD20 reference sequence can be a murine or human CD20 sequence. In an embodiment, the CD20 reference sequence is that of SEQ ID NO: 1. In another embodiment, the CD20 reference sequence is that of SEQ ID NO: 3.

A CD20 fragment that includes the third and fourth membrane-spanning domains and the loop formed between these (loop B) can be a reference sequence, for example, including residues K116 through N214. The CD20 reference sequence comprises, for example, residues I164 through Y184 of loop B. The CD20 fragment can include, for example, residues X to Y of SEQ ID NO: 1, where X is any residue of the sequence T104 to I128 corresponding to the sequence of human CD20 shown in FIG. 1, and Y is any residue of the sequence V196 to P297, having a disulfide bond between residues C167 and C183 under non-reducing conditions. For example, the CD20 fragment can include residues N140 to S185 of FIG. 1, with a disulfide bond between residues C167 and C183 under non-reducing conditions.

The membrane-spanning variants, for example variants of CD20, are soluble in non-ionic or zwitterionic detergent, such as DDPC, and retain sufficient "native" loop structure in the detergent to bind a known detecting antibody, such as rituximab (for example, RITUXAN®) or antigen binding fragment thereof, binds CD20 variants. In an embodiment, membrane-spanning variants include a loop in the extracellular domain, for example, in CD20, the loop formed between the third and fourth transmembrane-spanning domains. The loop can be about 30 to about 100 amino acids in length, about 40 to about 60 amino acids in length, about 40 to about 50 amino acids in length, about 45 to about 50 amino acids in length, or about 46 amino acids in length, for example. In an embodiment, the loop contains a disulfide bond, for example, for CD20, a disulfide bond at residues corresponding to Cys167 and Cys183 of SEQ ID NO: 1.

A membrane-spanning variant polypeptide can include amino acid substitutions, for example, in full length CD20 or the truncation mutants discussed above, that improve expression of the polypeptide. For example, substituting one or more of Cys111 and Cys220 of CD20 improves expression of human CD20 (see Example 1). A useful CD20 variant thus comprises an amino acid sequence substituted at one or both cysteine residues corresponding to Cys 111 and Cys220 of the human CD20 amino acid sequence of SEQ ID NO: 1. The cysteine residue can be non-conservatively substituted to prevent potential disulfide bonding. In the Examples below, Cys is replaced with Ser. The C2S-CD20 (also referred to as "C2S") mutant (SEQ ID NO: 6) (see table 2) of CD20 contains the double substitution Cys111Ser and Cys220Ser.

CD20 variants can be generated by any known methods of substituting, deleting, or inserting one or more amino acids, for example by mutating nucleic acid sequences encoding CD20. In an embodiment, "native" CD20 structure sufficient to retain antibody binding to loop B is maintained Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the CD20 sequence) can range from about 1 to 10 residues, 1 to 5 residues, or 1 to 3 residues, for example Amino acid sequence deletions can range from 1 to 30 residues, or 1 to 10 residues, for example, and typically are contiguous.

Guidance in determining amino acid residue(s) to be inserted, substituted, or deleted without adversely affecting the binding of antibody or antibody fragment, such as rituximab for CD20, can be found by comparing the sequence of the membrane-spanning polypeptide, for example, CD20, with that of known, homologous protein molecules, for example, having similar structure and/or functional domains, and minimizing the number of amino acid sequence changes made in regions of high homology, for example, greater than 50%, 55%, or 60% amino acid identity. For example, human and murine CD20 share 72% amino acid sequence identity with 63% identity in the extracellular loop between membrane-spanning domains three and four (loop B). Reference sequences such as the human CD20 (SEQ ID NO: 1) and murine CD20 (SEQ ID NO: 3) are used for alignment and comparison of identity regions of high and low homology.

Functional domains can also be identified in polypeptides known to have homology to the membrane spanning polypeptide, such as CD20. Sequences of functional domains can be compared and aligned to other known sequences, for example of CD20 or MS4A family polypeptides. CD20, IgE receptor β chain, and HTm4 have a common tetra-membrane-spanning structure with N- and C-terminal domains. An extracellular loop of approximately 50 amino acids is another common motif within the MS4A gene family. Additionally, this structure is common between different species, for example human and mouse. These three genes are localized to 11q12-q13.1 in humans and chromosome 19 in the mouse (Adra et al., 1989, *Proc. Natl. Acad. Sci. USA*, 91: 10178-10182; Hupp et al., 1989, *J. Immunol.*, 143: 3787-3791; Tedder et al., 1988, J. Immunol., 141: 4388-4394; Tedder et al., 1989, J. Immunol., 142: 2555-2559). The three genes are believed to have evolved from a common precursor (Liang et al., 2001, Supra).

Candidate positions for amino acid substitution are identified as those positions that show a high degree of variability in amino acids, i.e. at least 3 different amino acids are found at that position when different sequences are aligned and compared or have a lower percentage of sequence identity, i.e. less than 90% sequence identity. When sequences are aligned, positions that show variability can have conservative or non-conservative amino acid substitutions. Positions that have conservative amino acid substitutions may be substituted with the same type of substitution observed at the same positions in naturally occurring proteins. Examples of such substitutions are shown in Table 1.

TABLE 1

| Original Residue | Substitutions | Exemplary Substitutions |
|---|---|---|
| Ala (A) | val; leu; ile | val |
| Arg (R) | leu; gln; asn | lys |
| Asn (N) | gln; his; asp; lys; arg | gln |
| Asp (D) | glu; asn | glu |
| Cys (C) | ser; ala | ser |
| Gln (Q) | asn; glu | asn |
| Gly (G) | Ala | ala |
| his (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | Ala | ala |
| Ser (S) | thr; cys | cys |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of polypeptides such as CD20 are accomplished by selecting substitutions that differ significantly in their effect on maintaining (a) the structure of the polypeptide backbone in the area of the substitution, for example, as a sheet conformation, helical conformation, or loop structure, (b) the charge of hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions entail exchanging a member of one of these classes for another class. Such substituted residues also can be introduced into conservative substitution sites or into the remaining (non-conserved) sites.

Membrane-spanning polypeptide variants, such as CD20 variants can be made using known recombinant methods such as oligonucleotide-mediated (site-directed) mutagenesis, alanine scanning, PCR mutagenesis, site-directed mutagenesis (Zoller et al., 1987, Nucl. Acids Res., 10: 6487-6500), cassette mutagenesis (Wells et al., 1985, Gene, 34:315), restriction selection mutagenesis (Wells et al., 1986, Philos. Trans. R. Soc. London SerA, 317:415), and the like.

B. Expression Systems

1. Host Cells

The present invention provides methods for producing membrane-spanning polypeptides in host cells, and particularly in bacterial cells. Bacteria hosts useful to produce the membrane-spanning polypeptides include *Escherichia, Enterobacter, Bacillus, Pseudomonas, Klebsiella, Proteus, Salmonella, Serratia, Shigella*, and the like. Suitable bacterial hosts include *Enterobacteria*, such as *Escherichia coli, Shigella dysentariae, Klebsiella pneumoniae*, and the like. Suitable *Escherichia coli* hosts include strains W3110 (ATCC Accession No. 27,325), 294 (ATCC Accession No. 31,446), B, X1776 (ATCC accession 31,537), 58F3, and the like. Mutant cells of any of the above-mentioned bacteria may also be employed. Exemplified herein is the host cell *E. coli* strain 58F3 (W3110-fhuAΔ (tonAΔ) phoAΔE15 lonΔ galE rpoHts (htpRts) ΔclpP lacIq ΔompTΔ(nmpc-fepE) ΔslyD). It is expected that vectors, promoters, and the like can be similarly utilized and modified to permit efficient production of membrane-spanning proteins such as CD20 in other bacterial hosts.

Replicability of the replicon in the bacteria is taken into consideration when selecting bacteria for use in the methods of the invention. For example, *E. coli, Serratia*, and *Salmonella* species can be suitably used as the host when well known plasmids such as pBR322, pBR325, pACYC177, pKN410, and the like are used to supply the replicon.

2. Promoters

To effectively and efficiently produce complex membrane-spanning polypeptides in host cells such as in bacterial cells, a promoter is selected for low basal activity. Because the membrane-spanning polypeptides are generally toxic to host cells, even a low expression due to basal activity of a promoter may impact the health of the host cells, resulting in reduced cell growth, reduced protein production, and reduced yield. It is desirable to have the promoter "turned on" only for a short period of time while the host cells are sufficiently grown to permit a high production and good yield of protein. Accordingly, the promoter is selected and/or engineered herein for minimal basal activity.

Two commonly used promoters that are strong and allegedly tightly controlled, for example, in bacterial cells, are based on the native T7 and lambda PL promoters.

The strong T7 promoter is commercially available in pET vectors (Novagen, Stratagene, and others) and is used in a strain having a T7 RNA polymerase gene integrated into the chromosome (Lambda DE3 lysogenic strains). T7 RNA polymerase is under the control of the lac promoter/operator, and ultimately the T7 promoter operably linked to a gene of interest is induced with IPTG. This system by itself is rather leaky and toxic proteins such as multi-transmembrane proteins cause problems, including lack of growth prior to induction. To tighten control and reduce basal-level expression, an inhibitor of the T7 RNA polymerase, T7 lysozyme, can be co-expressed on a separate compatible plasmid (pLysS and pLysE by Novagen) in the same cell. The resulting expression system (pET/DE3strain/pLys) is still induced on addition of IPTG, whereby the high level of T7 RNA polymerase overpowers the lower level of T7 lysozyme inhibitor, turning on the T7 promoter.

The lambda PL promoter is another strong promoter, less commonly used. It is available on the commercial vector, pLEX (Invitrogen). The PL promoter operably linked to a gene of interest is positioned in the pLEX plasmid and the cI repressor that controls the PL promoter is integrated into the strain chromosome. The cI repressor is under the control of the trp promoter/operator.

Known inducible bacterial promoters can be used in the method of the invention, provided the promoter has low basal activity or is engineered to reduce basal activity, as described herein. Some examples include the beta-lactamase, lactose, and tryptophan promoters. Other promoters suitable for use in particular host cell systems are generally known and available, and can be engineered to reduce basal activity as described herein.

3. Control Elements

The phoA promoter is a tightly controlled promoter with low basal activity in *E. coli*. The phoA promoter is positively regulated via a pho box that binds the activator phoB (see Table 5). Promoter activity is turned on by phosphate depletion in the media, for example, by diluting into a limited phosphate medium. Despite its control mechanisms, the phoA promoter does exhibit some basal activity.

The promoter can be selected or engineered to contain one or more negative control element and one or more positive control element. See, for example, positive and negative control elements recited in Neidhardt, Ed., 1996, *Escherishia coli and Salmonella*, Second Ed., ASM Press, Washington D.C.

Promoters with both positive and negative control elements are rare. One example is the metE promoter. See, for example, Neidhardt, Ed., 1996, *Escherishia coli and Salmonella*, Second Ed., pages 1300-1309. Descriptions of known positive and negative control elements can be found, for example, in this reference. In some embodiments, the promoter has at least one positive and at least one negative control element that provide for direct control of basal expression. Positioning of a positive or negative control element within or adjacent to the promoter to achieve added regulation of the promoter is known, and is described, for example, in *Escherishia coli and Salmonella* (Supra) at pages 1232-1245.

Negative control elements include, for example, the lac repressor/lac operator, *E. coli* trp repressor/trp operator, lambda repressor/operator, and the like. Positive control elements include, for example, the pho box of the phoA promoter and variations that bind phoB, the MalT DNA binding site of the maltose operon promoter, the AraC DNA binding site of the arabinose operon promoter, and the like. For example, the phoA promoter, having the pho box as a positive control element, may be engineered to comprise a heterologous negative control element such as the lac operator. The lac operator is induced by addition of IPTG.

Two commonly used positive control elements for promoters are the PhoB/pho box and the AraC/araI DNA binding site. These and numerous other positive and negative transcriptional regulatory sequences are described, for example, in Neidhardt, Supra. Commonly used negative control elements include the lac repressor/lac operator, the trp repressor/trp operator, and the lambda repressor/lambda operator.

4. Transcription Terminators

To preclude read through from a different promoter system, one or more transcription terminators can be positioned to stop transcription read-through before it reaches the promoter operably linked to the nucleic acid sequence to be expressed. For example, the Lambda transcription terminator sequence AACG CTCGGTTGCC GCCGGGCGTT TTT-TATT (SEQ ID NO: 17) can be inserted upstream of the phoA promoter. Additional transcriptional terminator sequences are known, such as the His operon terminator, and can be used. Inserted control elements are positioned such that they are operatively linked with other promoter elements for controlled expression of the membrane-spanning polypeptide.

Induction of the promoter with an agent that affects a rapid and tightly controlled "on" and does not harm the host cells is also a desirable characteristic of the promoter system. For expression in *E. coli* and related bacteria, the phoA promoter provides tight control on expression. When mutated to add a negative control element such as, the lac operator and upstream Lambda transcription terminators, basal expression from the promoter was virtually eliminated, as shown in the Examples below.

Useful phoA promoters include native phoA promoter (SEQ ID NO: 5) and mutated phoA containing one or more negative control element, such as in the mutant promoter phac (SEQ ID NO: 15) and/or one or more upstream transcription terminator, such as in the mutant promoter tphac (SEQ ID NO: 16). Mutated promoters engineered to reduce basal promoter activity can be used.

In bacterial hosts other than *E. coli*, it may be useful to replace the phoA promoter with a functionally equivalent inducible promoter, selected or engineered for low basal activity, and known to be compatible with the selected bacterial host. Suitable promoters include, but are not limited to, beta-lactamase and lactose promoter systems, tryptophan promoter systems, or hybrid promoters such as the tac or trc promoter, that may be mutated to reduce basal promoter activity. The selected promoter may also be mutated to contain both positive and negative regulatory elements. For example, a naturally negatively regulated promoter can be engineered to add positive regulation by replacing the −35box sequence with a non-−35 consensus sequence, then adding a positive regulatory sequence element such as a pho box. It may be useful to replace the optional rare-codon tRNA genes with rare-codon tRNA genes known to be compatible with the selected bacterial host.

5. Vectors

Vectors useful to express membrane-spanning polypeptides generally contain a tightly controlled promoter operably linked to a polynucleotide encoding a membrane-spanning polypeptide. Plasmids such as, for example, pBR322, pBR325, pACYC177, or pKN410 can be used as the backbone of the vectors. In an embodiment, plasmid pBR322 forms the backbone.

Vectors for expressing membrane-spanning polypeptides generally include a strong promoter, negative and positive control elements, transcription terminators, and additional elements for tight control and efficient expression and translation.

Vectors can include a short sequence encoding an amino acid leader positioned just prior to the first codon of the encoded polypeptide. The leader sequence aids proper translation initiation, and generally contains about 6 to 12 amino acids, and may contain, for example, 6, 7, 8, 9, 10, 11, or 12 amino acids, although it can contain more. One example is the sequence MKHQHQQ (SEQ ID NO: 7), for example, encoded by the nucleic acid sequence: (ATG)AAACAC-CAACACCAACAA (SEQ ID NO: 28), as shown in FIG. 21. A longer leader sequence, for example, 30-50 or more amino acids, is useful to aid translation elongation of membrane-spanning polypeptides. See, for example, the trpLE leaders LE and sLE shown in FIG. 22, that contain a translation initiation sequence (TIS) and a spacer sequence to aid translation elongation.

The vector can also include rare-codon tRNA genes for the host cell. Examples of rare-codon tRNA genes for *E. coli* include, but are not limited to, argU, glyT, and pro2.

6. Leader Sequence

In a preferred embodiment for expressing membrane-spanning polypeptides, the leader sequence contains a strong translation initiation sequence (TIS) and a spacer sequence positioned between the TIS and the first transmembrane segment (TM-1). One useful leader for expression of multi-membrane spanning polypeptides in *E. coli* contains a portion of the trpLE leader. See, for example, the LE and sLE leaders encoding a portion of the N-terminal region of the *E. coli* trpE protein disclosed in the Examples below.

7. Translation Initiation Sequence

Known translation initiation sequences can be used to enhance the efficiency of initiation of translation of a gene. A translation initiation enhancer sequence can extend to include sequences 5' and 3' to the ribosome binding site. The ribosome binding site is defined to include, minimally, the Shine-Dalgarno region and the start codon, in addition to any bases in between. In addition, the translation initiation enhancer sequence can include an untranslated leader or the end of an upstream cistron, and thus a translational stop codon. See, for example, U.S. Pat. No. 5,840,523.

There are numerous ways to obtain high level rates of translation initiation, including use of approximately the first 6-12 or so codons of a protein highly expressed in the host cell. For example, in *E. coli*, several protein leaders having good translation initiation regions at the beginning of the coding sequence include beta-galactosidase (Ruther et al., 1983, *EMBO J.*, 2:1791-1794), Protein A (Nilsson et al., 1990, *Methods Enzymol.*, 185:144-161), Glutathione-S-transferase (Smith et al, 1988, *Gene*, 67:31-40), and the like. Another example is the sequence MGSSHHHHHH(SEQ ID NO: 33), for example, encoded by the nucleic acid sequence: ATGGGCAGCAGCCATCATCATCATCATCAT (SEQ ID NO: 34). See also a general review of such leaders: Lavallie et al., 1995, *Current Biology*, 6:501-506.

Alternatively, a strong TIS can be designed, for example, as described in 1990, *Methods in Enzymol.*, 185:89-119. A strong TIS can also be selected, for example, as described in Yansura et al., 1992, *Methods: A companion to Methods in Enzymology*, 4:151-158.

A "strong translation initiation sequence" is generally a sequence of codons that encode about 6 to about 12 amino acids (for example, 6, 7, 8, 9, 10, 11, or 12 amino acids). The sequence can be natural or engineered, and permits a high rate of translation initiation.

In one embodiment, a strong translation initiation sequence contains the first nine amino acids of the trp leader (M)KAIFVLKGS (SEQ ID NO: 27) encoded by the nucleic acid sequence: ATGAAAGCAATTTTCGTACTGAAAG-GTTCA (SEQ ID NO: 35). Others include the nucleotide sequence encoding the first 6-12 amino acids of β-galactosidase.

8. Spacer Sequence

A spacer sequence separating the TIS from the TM-1 of the translated protein is useful to aid translation elongation of membrane-spanning polypeptides. A useful spacer sequence contains minimal barriers to elongation, for example, minimal rare amino acids, binds poorly to ribosomes, and is typically unstructured, for example, does not fold to permit translocation across the membrane if necessary, and thus permits a rapid rate of translation elongation. It is hypothesized that the "spacer sequence" functions as a buffering space to accommodate a slowing of translation at the first transmembrane segment without loss of ribosomal loading at the TIS and continuing elongation. The spacer must be long enough to efficiently separate the TIS from the TM-1, yet not so long as to permit folding of the translated polypeptide. The spacer sequence permits efficient and rapid translation elongation, without disrupting normal protein insertion into the membrane.

The spacer sequence may comprise, for example, a sequence of 50 or more amino acids, for example 60 or more, 70 or more, 80 or more amino acids, and is preferably fewer than 120 amino acids. In one embodiment, the "spacer sequence" is hydrophilic, and may contain about 20% to about 50% charged amino acids, for example about 30% to about 40% charged amino acids.

In another embodiment, the spacer sequence comprises at least a portion of a bacterial gene, and may be derived from a sequence naturally found in the host cell, for example, the E gene of the *E. coli* trp operon for expression of polypeptides in *E. coli* cells. As described in the Examples below, the LE and sLE leaders contain a portion of the trpE gene.

9. Expression Tag

In general, an expression tag may be a component of the vector, or be a part of the polypeptide DNA inserted into the vector. Expression tags serve to identify and isolate the expressed protein. Examples include, but are not limited to, poly-His tags (U.S. Pat. No. 4,569,794), HisGln tag, biotin, avidin, and the like. Such tags are well known and commercially available (See, for example, Qiagen, Valencia, Calif.). A poly-His tag comprises multiple histidine residues, generally 6-10 histidine residues. His-tagged polypeptides can be detected by applying a sample to a column coupled to an anti-His tag antibody or to a nickel column.

FIGS. 8, 21, and 22 diagrammatically represent exemplary expression constructs containing sequences useful in the methods of the invention to express membrane-spanning polypeptides. Shown, for example, in FIG. 8 are operably-linked sequences of a promoter, leader sequence, membrane-spanning protein gene, expression tag, transcription terminator (lambda $t_o$) and tRNA genes. The Examples below demonstrate the use of such expression constructs for the expression of CD20, RA1c, GPR73, and MS4A4A.

C. Expression of Membrane-Spanning Polypeptides in Bacterial Cells

Expressed membrane-spanning polypeptides associate with the bacterial cell membrane in a native conformation. Localization of membrane-spanning polypeptides to the bacterial cell membrane can be determined, for example, by density gradient centrifugation or other known methods.

Bacterial hosts are cultured in known, suitable media. Any media supplements besides carbon, nitrogen, and inorganic phosphate sources are included at appropriate concentrations introduced alone or as a mixture with another supplement or medium such as a complex nitrogen source. The host cells are cultured at suitable temperatures. For example, *E. coli* can be grown at temperatures from about 20° C. to about 39° C., for example 25° C. to 37° C., or about 30° C. The pH of the culture medium may be any pH from about 5-9, depending on the host organism. The culture medium for *E. coli* can have a pH of about 6.8 to about 7.4, for example, about 7.0.

Polynucleotides encoding membrane-spanning polypeptides are prepared by known recombinant methods. These methods include, but are not limited to, isolation from a natural source, PCR, oligonucleotide-mediated (site-directed) mutagenesis, alanine scanning, PCR mutagenesis, site-directed mutagenesis (Zoller et al., 1987, *Nucl. Acids Res.*, 10: 6487-6500), cassette mutagenesis (Wells et al., 1985, *Gene*, 34:315), restriction selection mutagenesis (Wells et al., 1986, *Philos. Trans. R. Soc. London SerA*, 317:415), and the like.

A polynucleotide encoding a membrane-spanning polypeptide may be expressed directly, or as a fusion with another polypeptide, or as a polypeptide having a specific cleavage site at the C-terminus of the mature polypeptide, for example.

The methods of the invention utilize standard recombinant procedures to produce membrane-spanning-polypeptides. A heterologous polynucleotide encoding a membrane-spanning-polypeptide (e.g., cDNA or genomic DNA) is inserted into a replicable vector for expression in the bacterium. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: origin of replication, one or more marker gene, and inducible promoter. Examples of suitable vectors are described herein. In an embodiment of the invention, vectors contain a promoter under high regulation operably linked to a gene encoding a membrane-spanning polypeptide. Examples of suitable promoters are described herein, and include the phoA, phac, and tphac promoters, and other such promoters under tight control, for example, by both positive and negative control elements. As described herein, the vectors can also contain strong translation initiation sequences and spacer sequences to enhance elongation of multi-membrane spanning polypeptides.

In general, plasmid vectors containing replicon and control sequences derived from species compatible with the bacterial host cell are used. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., 1977, *Gene*, 2: 95). The plasmid pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacillus* spp. One example of a selection scheme utilizes a drug to arrest growth of a host cell. Those cells that are successfully transformed with a heterologous gene produce a protein conferring drug resistance and thus survive the selection regimen.

Promoters can be induced utilizing standard methods. See, for example, Sambrook et al., Molecular Cloning: A Laboratory Manual (New York: Cold Spring Harbor Laboratory Press, 1989). In general, bacterial cells are cultured until a certain optical density is achieved, at which point induction is initiated by addition of an inducer, by depletion of a medium component, or both, as required by the selected promoter. The phoA promoter is induced by phosphate depletion, as described, for example, in: Chang et al., 1987, *Gene*, 55: 189-196; Simmons et al., 2002, *J. Immunol. Methods*, 263: 133-147; and/or U.S. Pat. Nos. 5,304,472 and 5,342,763.

When the promoter contains both positive and negative control elements, for example the pho box and the lac operator contained in the mutant promoters phac and tphac, it is desirable to coordinate induction of the promoter via both control elements. For example, induction via removal of the negative control element at the lac operator by addition of IPTG can be coordinated with a low point in phosphate depletion of the medium, so that both control elements "turn on" the promoter activity simultaneously, or as close in time as possible. The duration of promoter directed expression is generally limited in time to maintain health of the expressing cells, for example less than 3 hours, less than 2 hours, or some time in the range of 1 to 2 hours. The duration of expression can vary with the host cells and with the specific polypeptide being expressed.

Cells are lysed, soluble and insoluble fractions are separated, and the membrane-spanning polypeptides are extracted from the insoluble membrane fraction. Exemplary solubilization methods are discussed below.

Gene expression can be measured in a sample indirectly, for example, by conventional northern blotting to quantitate the transcription of mRNA (Thomas, 1980, *Proc. Natl. Acad. Sci. USA*, 77: 5201-5205). Various labels may be employed, most commonly radioisotopes, particularly $^{32}$P. Other techniques may also be employed, such as biotin labeling. Biotin-modified nucleotides introduced into a polynucleotide can serve as the site for binding to avidin or antibodies that can be labeled with a wide variety of labels, such as radionucleotides, fluorescers, enzymes, or the like. Gene expression can also be measured directly, by analysis of expressed polypeptides, for example by Western blot.

D. Isolation and Purification of Membrane-Spanning Polypeptides

Membrane-spanning polypeptides can be isolated from host cells such as bacterial cells free of the cells or cellular membranes, by the methods described herein, and are soluble in detergent, retaining sufficient "native" conformation such that the polypeptides can be recognized as an immunogen or bound by a ligand. The isolated polypeptide retains sufficient "native" conformation so as to bind a ligand whose binding is dependent upon a structural feature present in the native conformation of the polypeptide. For example, rituximab binding of CD20 is dependent on extracellular loop B in the native conformation of CD20 (e.g. when CD20 is expressed on a cell membrane). CD20 solubilized in non-ionic or zwitterionic detergent as described herein contains sufficient "native" loop B structure in the detergent so as to bind rituximab or an antigen-binding fragment thereof, such as a Fab fragment.

1. Host Cell Disruption

Host cells harboring the expressed membrane-spanning polypeptides can be disrupted by various physical or chemical methods including, but not limited to, freeze-thaw cycling, sonication, mechanical disruption, cell lysing agents, and the like. The membrane-spanning polypeptide can be released from the cell or cellular membrane using a suitable detergent or by enzymatic cleavage. The membrane-spanning polypeptides are recovered from the disrupted cells by solubilizing in detergent.

2. Mild Non-Denaturing Detergents

A common method of solubilizing membrane proteins is through the use of mild non-denaturing detergents such as Dodecyl-maltoside, n-Dodecyl-N,N,-Dimethylamine-N-Oxide, n-Dodecylphosphocholine (FOS-Choline-12) and triton X-100, A variant of this method is the use of mixed micelles composed of detergent and lipid (typically in a ratio of 10:1). Such a methodology was applied recently in the isolation and crystallization of the Kv1.2 potassium channel. (Long et al., 2005, *Science* 309(5736):897-903 and Long et al., 2005, *Science* 309(5736):903-8). Strong denaturing detergents such as SDS, while not preferred, can be used to solubilize and denature polypeptides. The protein is then typically re-constituted, into a more mild detergent, or liposome or other non-detergent environment prior to biochemical study. It can be difficult, however, to restore normal function after exposing proteins to denaturing detergents.

3. Non-Ionic and Zwitterionic Detergent

In one embodiment, the membrane-spanning polypeptides are solubilized in a non-ionic or zwitterionic detergent. Examples of non-ionic detergents useful to solubilize complex membrane-spanning polypeptides such as CD20 include, but are not limited to, TRITON® and dodecyl maltoside. Examples of zwitterionic detergents useful to solubilize complex membrane-spanning protein such as CD20 include, but are not limited to, zwittergents, such as zwittergent 3-08, 3-10, 3-12, 3-16, (Cal Bio Chem), ASB-14, ASB-16, ASB-C80 (Anatrace), PMAL-B 100, and phosphocholine derivatives, such as, dodecyl phosphocholine (DDPC), and the like. Phosphocholine detergents contain choline, having a quaternary amine with a positive charge bound to phosphate that is ionic and polar. Derivatives contain non-polar hydrocarbon chains attached to the phosphate, for example, dodecyl for DDPC. Useful phosphocholine derivatives include lysophospholipids DDM, DM, LADO, DDPC, DHPC, LOPC, LMPC, DLPC, LLPG (available from Avanti Polar Lipids (Alabaster, Ala.) and or Anatrace Inc. (Maumee, Ohio)), and n-decyl-N,N-dimethylamine-N-oxide, for example.

4. Ionic or Denaturing Detergent

Extractions with ionic or denaturing detergents may not yield isolated membrane-spanning polypeptides that retain sufficient useful "native" conformation. Resuspending the isolated polypeptides in a non-ionic or zwitterionic detergent permits reshaping of the polypeptide and yields membrane-spanning polypeptides with useful "native" conformation. For example, membrane-spanning polypeptides can be extracted from cell membranes using an ionic detergent. To be useful, for example, in an immunoassay, the ionic detergent can be exchanged for a non-ionic or zwitterionic detergent.

5. Small Scale Purification

The methods of solubilization and purification may vary depending on the scale of the extraction and purification. For small scale extractions and purification, for example, up to about 1 g of cells, the cell pellet can be incubated in detergent and the detergent soluble and insoluble fractions can be recovered without further purification steps.

6. Large Scale Purification

For large scale extractions and purification, for example, of about 100 g or more of cells, the cells can be mixed with detergent and centrifuged. The resulting supernatant can be purified using know methods including, but not limited to, fractionation on an ion-exchange column; affinity chromatography, for example, anti-His-Tag or anti-CD20 antibody, for example; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex® G-75; Protein A Sepharose® columns to remove contaminants such as IgG; metal chelating columns to bind epitope-tagged forms of the polypeptides, hydrophobic affinity resins, ligand affinity using an appropriate ligand immobilized on a matrix, sucrose density gradient centrifugation, and the like. Various methods of protein purification are known and may be employed. See, for example, Deutscher, 1990, *Methods in Enzymology*, 182; Scopes, 1982, In: *Protein Purification: Principles and Practice*, Springer-Verlag, New York; Ausubel et al. (ed.), 1998, In: *Current Protocols in Molecular Biology*, John Wiley & Sons.

7. His-Tag

In an embodiment, the membrane-spanning polypeptides are His-tagged. Purification of His-tagged polypeptides can be achieved, for example, by passing the solubilized detergent fraction over a metal chelating column, such as for example a metal chelating Ni-NTA column, or a column containing immobilized anti-His antibodies. Following capture, the His-tagged polypeptides are eluted with an appropriate buffer. In an embodiment the buffer contains 0.1% n-dodecyl-β-D-maltoside, 150 mM NaCl, and 20 mM sodium citrate, pH 3.5.

8. Affinity Purification

In another embodiment, the membrane-spanning polypeptides are affinity purified from the solubilized detergent fraction by passing the fraction over a column with immobilized ligand that binds the "native" structure of the polypeptide. For example, CD20 can be purified from detergent using rituximab. The eluted fractions containing the membrane-spanning polypeptide can be further concentrated and purified by gel filtration, affinity purification, and the like. Protein concentrations can be determined by various well-known methods, such as for example BCA determination (Smith et al., 1985, Anal. Biochem., 150: 76-85).

9. Non-Detergent Manipulation

Once proteins have been purified they may be manipulated in a non-detergent environment if desired. The most common non-detergent environment is a liposome, which more closely mimics the native cellular environment than do detergent micelles. Liposomes are composed primarily of long chain lipids. See, for example, Rigaud et al., 1995, Biochim Biophys Acta. 1231(3):223-46 and Ollivon et al., 2000, Biochim Biophys Acta. 1508(1-2):34-50. Bicelles are a variant of liposomes that are formed primarily from bilayer forming lipid mixed with a short chain lipid. See, for example, Czerski and Sanders, 2000, Anal Biochem. 284(2):327-33.

E. Methods Using the Isolated Proteins

1. Affinity Maturation/Antibody Selection

Membrane-spanning polypeptides, expressed, isolated and/or purified as described herein, having useful "native" conformation, can be used as target antigens for selection of antibody variable domains using phage display and for affinity maturation of antibodies. Methods are known for phage display of antibody variable domains and selection of specific binders for the antigen. An "affinity matured" antibody contains one or more alteration in one or more hypervariable region that results in improved affinity of the antibody for antigen, as compared to a parent antibody that does not possess the alteration(s). Affinity matured antibodies can have nanomolar or even picomolar affinities for the target antigen.

Phage display is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, Curr. Opin. Struct. Biol., 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, Methods: A companion to Methods in Enzymology, 3:205-0216 (1991). Exemplary methods for phage display of antibody variable domains can be found in US Application Publication No. 2005-0119455-A1, which is hereby incorporated by reference.

Marks et al., 1992, Bio/Technology, 10:779-783, describes affinity maturation by VH and VL domain shuffling. Random mutagenesis of CDR and/or framework residues is described by Barbas et al., 1994, Proc. Nat. Acad. Sci. USA, 91:3809-3813; Scier et al., 1995, Gene, 169: 147-155; Yelton et al., 1995, J. Immunol., 155: 1994-2004; Jackson et al., 1995, J. Immunol., 154: 3310-3319; and Hawkins et al., 1992, J. Mol. Biol., 226: 889-896.

"Affinity maturation using phage display" (AMPD) refers to a process described in Lowman et al., 1991, Biochemistry 30(45): 10832-10838. See also Hawkins et al., 1992, J. Mol. Biol. 226, 889-896 and U.S. Pat. No. 6,172,213. While not strictly limited to the following description, this process can be described briefly as follows: Several hypervariable region sites (e.g. 6-7 sites) are mutated to generate all possible amino acid substitutions at each site. The antibody mutants thus generated are displayed in a monovalent fashion from filamentous phage particles as fusions to the gene III product of M13 packaged within each particle. The phage expressing the various mutants can be cycled through rounds of binding selection, followed by isolation and sequencing of those mutants that display high affinity. This method is also described in WO92/09690. A modified procedure involving pooled affinity display is described in Cunningham, et al., 1994, EMBO J. 13(11), 2508-2515.

Affinity maturation by phage display provides for selecting novel binding polypeptides, for example, using the following steps:

a) constructing a replicable expression vector comprising a first gene encoding a polypeptide, a second gene encoding at least a portion of a natural or wild-type phage coat protein wherein the first and second genes are heterologous, and a transcription regulatory element operably linked to the first and second genes, thereby forming a gene fusion encoding a fusion protein;

b) mutating the vector at one or more selected positions within the first gene thereby forming a family of related plasmids;

c) transforming suitable host cells with the plasmids;

d) infecting the transformed host cells with a helper phage having a gene encoding the phage coat protein;

e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle;

f) contacting the phagemid particles with a target molecule so that at least a portion of the phagemid particles bind to the target molecule; and g) separating the phagemid particles that bind from those that do not.

Affinity maturation methods can further comprise transforming suitable host cells with recombinant phagemid particles that bind to the target molecule and repeating steps d) through g) one or more times.

Alternatively, the method includes polypeptides that are composed of more than one subunit, wherein the replicable expression vector comprising a transcription regulatory element operably linked to DNA encoding the subunit of interest is fused to the phage coat protein.

Alternatively, multivalent phage (McCafferty et al., 1990, Nature 348, 552-554; Clackson et al., 1991, Nature 352, 624-628) can also be used to express random point mutations for example, generated by use of an error-prone DNA polymerase, to generate a library of phage antibody fragments that could then be screened by affinity to antigen (Hawkins et al., 1992, J. Mol. Biol. 226: 889-896).

2. Screening Assays

Accurate and highly sensitive screening for identifying and/or quantifying a target molecule of interest, such as a human, human-chimeric, or humanized antibody, or a fragment of such antibodies can be achieved. Membrane-spanning polypeptides prepared as described herein, as target-specific capture reagents, for example.

One useful assay method generally comprises the following steps: (1) reacting membrane-spanning polypeptide to target molecule present in the sample; and (2) quantitating the bound target molecule. The membrane-spanning polypeptide can be immobilized on a surface as a capture reagent.

3. ELISA

Immunoassay systems include, for example, solid-phase ELISA and capture ELISA. In a capture ELISA, immobilization of the membrane-spanning polypeptides to a solid phase is accomplished by known methods. The polypeptide may be absorbed onto a solid phase that comprises an assay surface or matrix (see, for example, U.S. Pat. No. 3,720,760). The polypeptide can be coupled, non-covalently or covalently to an assay surface, with or without prior activation of the support. Deposit of the membrane-spanning polypeptide as a capture reagent can also be by immunoprecipitation, for example, after binding the sample antibody. In one embodiment, the membrane-spanning polypeptide is immobilized by diluting the polypeptide solution to below the critical micelle value. Deposition of the soluble protein onto an assay surface can be achieved in slightly denaturing conditions, for example, mildly basic or acidic conditions. Alternatively, the protein can be captured by a covalent linkage at the assay surface, or bound by a protein such as an antibody disposed on the assay surface.

In an embodiment, the capture reagent is a membrane-spanning polypeptide such as CD20, in its isolated, native conformation produced by the methods of the invention.

Fragments of the polypeptide can also be used. The membrane-spanning polypeptide binds an antibody from a sample.

The solid phase used for immobilization may be any inert support or carrier that is essentially water insoluble and useful in immunoassays, including supports in the form of, for example, surfaces, particles, porous matrices, and the like. Examples of commonly used supports include small sheets, Sephadex, polyvinyl chloride, plastic beads, microparticles, assay plates, test tubes manufactured from polyethylene, polypropylene, polystyrene, and the like. Such supports include 96-well microtiter plates, as well as particulate materials such as filter paper, agarose, cross-linked dextran, and other polysaccharides. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are suitably employed for capture reagent immobilization. The immobilized capture reagent can be coated on a microtiter plate. The solid phase can be a multi-well microtiter plate that can be used to analyze several samples at one time.

The solid phase is coated with the capture reagent that may be linked by a non-covalent or covalent interaction or physical linkage, as desired. Techniques for attachment include those described in U.S. Pat. No. 4,376,110 and the references cited therein.

If polystyrene or polypropylene plates are utilized, the wells in the plate can be coated with the capture reagent (typically diluted in a buffer such as 0.05 M sodium carbonate) by incubation for at least about 10 hours, for example, overnight, at temperatures of about 4-20° C., for example 4-8° C., and at a pH of about 8-12, for example in the range of 9-10 or about 9.6. If shorter coating times (1-2 hours) are desired, the plate can be coated at 37° C. or contain nitrocellulose filter bottoms, for example, Millipore MULTI-SCREEN™ (Billerica, Mass.) can be used. The membrane-spanning proteins may be applied to an assay surface as soluble proteins in detergent. Dilution of the detergent to below the critical micelle value will cause the polypeptide to precipitate on the assay surface.

The coated plates are typically treated with a blocking agent that binds non-specifically to and saturates the binding sites to prevent unwanted binding of free ligand to excess binding sites on the wells of the plate. The blocking treatment typically takes place under conditions of ambient temperatures for about 1-4 hours, for example, in the range of 1.5 to 3 hours.

After coating and blocking, the serum sample to be analyzed is diluted as necessary and added to the immobilized phase. The dilution rate is generally about 5-15%, for example 10%, by volume. For sufficient sensitivity, the immobilized capture reagent can be in molar excess of the maximum molar concentration of the analyte anticipated in the sample after appropriate dilution. Conditions for incubation of sample and capture reagent are selected to maximize sensitivity of the assay and to minimize dissociation. Incubation time depends primarily on the temperature.

The sample is separated from the immobilized capture reagent with a wash solution to remove uncaptured analyte from the system. The wash solution is generally a buffer.

In general, the system can be washed three times. The temperature of the wash solution is typically from about 0-40° C., for example, in the rage of 4-30° C. An automated plate washer may be utilized. A cross-linking agent or other suitable agent may be added to the wash solution to covalently attach the captured analyte to the capture reagent.

Following removal of uncaptured analyte molecules from the system, the captured analyte molecules are contacted with a detection reagent, such as an antibody, for example, at room temperature.

The temperature and time for contacting the analyte with the detecting agent is dependent primarily on the detection means employed. For example, when horseradish peroxidase (HRP) conjugated to sheep anti-mouse IgG is used as the means for detection, the detecting agent can be incubated with the captured analyte for about 0.5-2 hours, for example, about 1 hour. The system is washed as described above to remove unbound detecting agent from the system and developed by adding peroxidase substrate and incubating the plate for about 5 minutes at room temperature or until good color is visible.

A molar excess of the detection reagent can be added to the system after the unbound analyte has been washed from the system. The detection reagent may be a polyclonal or monoclonal antibody, or mixture thereof. The detection reagent may be directly or indirectly detectable The affinity of the detection reagent is sufficiently high such that amounts of analyte can be detected. A fluorimetric or chemiluminescent label moiety has greater sensitivity in immunoassays compared to a conventional colorimetric label. The binding affinity of the selected detection reagent must be considered in view of the binding affinity of the capture agent such that the detection reagent does not strip the analyte from the capture reagent.

The label moiety is any detectable functionality that does not interfere with the binding of the captured analyte to the detecting agent. Examples of suitable label moieties include moieties that may be detected directly, such as fluorochrome, chemo-luminescent, luminescent and radioactive labels, as well as moieties, such as enzymes, that must be reacted or derivatized to be detected. Examples of such labels include, but are not limited to radioisotopes $^{32}P$, $^{14}C$, $^{125}I$, $^{3}H$, and $^{131}I$, fluorophores such as rare earth chelates or fluorescein and its derivatives, rhodamine and its derivatives, luceriferases, e.g., firefly luciferase and bacterial luciferase (U.S. Pat. No. 4,737,456), horseradish peroxidase (HRP), alkaline phosphatase, an enzyme that employs hydrogen peroxide to oxidize a dye precursor such as HPP, biotin/avidin, biotin/streptavidin, and the like.

Conjugation of the label moiety to the detecting agent, such as for example an antibody, is a standard manipulative procedure in immunoassay techniques. See, for example, O'Sullivan et al. 1981, *Methods in Enzymology,* 73:147-166. Conventional methods are available to bind the label moiety covalently to proteins or polypeptides.

The amount of analyte bound to the capture reagent can be determined by washing away unbound detecting agent from the immobilized phase and measuring the amount of detecting agent bound to the analyte using a detection method appropriate to the label. In an embodiment, the label moiety is an enzyme. In the case of enzyme moieties, the amount of developed color is a direct measurement of the amount of captured analyte. For example, when HRP is the label moiety, color is detected by quantifying the optical density (O.D.) at 650 nm absorbance. In another embodiment, the quantity of analyte bound to the capture reagent can be determined indirectly.

4. Antibody Preparation

A membrane-spanning polypeptide such as CD20, solubilized in detergent, can be directly used as an immunogen to generate anti-membrane-spanning antibodies. Other methods for generating antibodies can also be utilized including phage display methodologies as described herein.

The antibody is raised against the antigen derived from a first mammalian species, for example, the first mammalian species can be human. However, other mammals are contemplated such as farm, pet, or zoo animals, e.g. where the antibody is intended to be used to treat such mammals.

To generate an antibody mutant, one or more amino alterations (e.g. substitution, deletion, addition) are made to the amino acid sequence, as known.

(i) Antigen preparation. A membrane-spanning antigen to be used for production of antibodies can be, for example, a soluble form of the full-length polypeptide or a fragment thereof, such as the solubilized full length molecule or a fragment such as the extracellular domain of a membrane-spanning polypeptide.

(ii) Polyclonal antibodies. Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, and the like.

Animals can be immunized against the antigen, immunogenic conjugates, or derivatives by combining, for example, 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. For example, the animal can be boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal antibodies. Monoclonal antibodies may be made using the hybridoma method first described by Kohler et al., 1975, *Nature*, 256: 495, or by recombinant DNA methods for example, as described in U.S. Pat. No. 4,816,567, or other known methods.

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Lymphocytes then are fused with myeloma cells using a suitable fusing agent, such as polyethylene glycol, to form a hybridoma cell (Goding, 1986, Monoclonal Antibodies: Principles and Practice, pp. 59-103, Academic Press). The hybridoma cells thus prepared are seeded and grown in a suitable culture medium, for example, containing one or more substances that inhibit the growth or survival of the unfused, parental myeloma cells.

After hybridoma cells are identified that produce antibodies of the desired specificity, affinity, and/or activity, the clones may be subcloned by limiting dilution procedures and grown by standard methods (Goding, 1986, Supra). Monoclonal antibodies secreted by the subclones are suitably separated from the culture medium, ascites fluid, or serum by conventional immunoglobulin purification procedures such as, for example, protein A-Sepharose®, hydroxylapatite chromatography, gel electrophoresis, dialysis, affinity chromatography, or the like.

DNA encoding the monoclonal antibodies is readily isolated and sequenced using conventional procedures. In one example, oligonucleotide probes capable of binding specifically to genes encoding the heavy and light chains of the monoclonal antibodies are used. Hybridoma cells can serve as a source of such DNA.

The binding affinity of the monoclonal antibody can be determined for example, by Scatchard analysis as described in Munson et al., 1980, *Anal. Biochem.*, 107: 220.

(iv) Humanization and amino acid sequence variants. Examples of methods for humanization of antibodies are provided in U.S. Pat. No. 6,037,454 (anti-CD11a antibodies), U.S. Pat. No. 6,329,509 (anti-IgE antibodies), U.S. Pat. No. 5,821,337 (anti-p185$^{HER2}$ antibodies), and WO 98/45331 anti-vascular endothelial growth factor (anti-VEGF antibodies), and are hereby incorporated by reference.

As described previously, a number of methods may be utilized to select antibodies specific for the membrane-spanning proteins described herein such as phage display, conventional immunization, affinity maturation, and other methods.

All publications, patents, and patent documents are incorporated by reference herein, as though individually incorporated by reference. The disclosure has been described with reference to various specific and preferred embodiments and techniques. However, it should be understood that many variations and modifications can be made while remaining within the spirit and scope of the disclosure.

EXAMPLES

The invention may be better understood with reference to the following Examples that are exemplary and do not serve to limit the invention in any way.

Example 1

Cloning and Expression of CD20 with phoA Promoter

Materials

All detergents were obtained from Anatrace Inc., Maumee, Ohio. Unless otherwise mentioned all chemicals were obtained from Sigma-Aldrich, St. Louis, Mo. Full length rituximab antibody was obtained from Genentech Manufacturing. Rituximab Fab was expressed in *E. coli* and purified by Protein A and cation exchange chromatography. Expression constructs used in the Examples below are diagrammatically shown in FIGS. 8 and 21, and useful leader sequences are shown in FIG. 22. *E. coli* cells were strain 58F3, unless otherwise indicated.

Cloning & Expression

The cDNAs for human and murine CD20 were sub-cloned, using standard molecular biology techniques (Ausubel et al. eds., 2003, *Current Protocols in Molecular Biology*, 4 Vols., John Wiley & Sons), into a BR322-derived plasmid containing the β-lactamase gene and tRNA genes for three rare *E. coli* codons (argU, glyT and pro2). Short polynucleotides were added to encode a leader sequence, MKHQHQQ (SEQ ID NO: 7) at the N-terminus of CD20 to ensure high translation initiation, and to encode a tag sequence, octa-His (SEQ ID NO: 8) at the C-terminus to aid in detection and purification of the expressed protein. Gene transcription was under control of the phoA promoter, and expression was induced by limiting phosphate. A saturated LB carbenicillin culture was diluted into C.R.A.P. phosphate limiting media (Simmons et al., 2002, *J. Immunol. Methods*, 263:133-147). The culture was then grown at 30° C. for 24 hours.

Mutant CD20 was produced, replacing residues Cys111 and Cys220 with serine by site directed mutagenesis to form the C2S mutant. The mutant was tested for improved protein behavior as compared with non-mutated CD20, including aggregation, expression, solubility, and retention of native conformation. Fermenter expression of CD20 was performed as described in Simmons et al., 2002, Supra.

Protein Isolation

To analyze various detergents for their ability to solubilize His-tagged human CD20 expressed in *E. coli*, 5 g of cells were resuspended using a Polytron (Brinkmann, Westbury, N.Y.) in 50 mL buffer A (20 mM Tris, pH 8.0, 5 mM EDTA) and centrifuged at 125,000×g for 1 hour. The cell pellet was then resuspended in buffer A, lysed by cell disruption using a microfluidizer (Microfluidics Corp, Newton, Mass.), and centrifuged at 125,000×g for 1 hour. The pellet was washed once in the same buffer without EDTA and pelleted as before. The pellet was resuspended in 20 mL buffer B (20 mM Tris, pH 8.0, 300 mM NaCl), aliquoted and test detergents were added to individual aliquots at the following concentrations:

1% SDS;
1% n-lauryl sarcosine
1% n-dodecyl-N,N-dimethylamine-N-oxide (LADO);
1% dodecylphosphocholine (DDPC, Fos-Choline® 12);
1% n-dodecyl-β-D-maltoside (DDM);
1% Triton® X-100;
2.5% CHAPS.

Pellets were extracted overnight at 4° C., except for the SDS sample that was extracted at room temperature. The following day the samples were centrifuged and the supernatants removed. Pellets and supernatants were re-suspended in reducing SDS loading buffer to equal volumes and analyzed by SDS-PAGE and immunoblots on nitrocellulose membranes probed with horseradish peroxidase-conjugated anti-His antibodies (Roche Applied Science, Indianapolis, Ind.).

For large-scale extraction, 100 to 200 g of cells were lysed and the insoluble fraction prepared as previously described. To extract CD20 from the insoluble fraction, the final pellet was re-suspended in buffer B at approximately 1:2.5 wt/vol from the starting wet cell weight, DDPC was added to 1% and the solution was stirred overnight at 4° C. The next day the detergent insoluble fraction was pelleted by ultracentrifugation at 125,00×g for 1 hour. The supernatant was loaded onto a Ni-NTA SUPERFLOW™ column (Qiagen Inc. Valencia, Calif.) that had been pre-equilibrated with buffer B and 5 mM DDPC. The column was washed with 10 column volumes of buffer A containing 20 mM imidazole and bound protein was eluted with buffer A containing 250 mM imidazole. All of the purification steps through column loading were performed at 4° C.

Eluant fractions containing CD20 were concentrated and loaded onto a SUPERDEX™ 200 column (Amersham Biosciences, Piscataway, N.J.) pre-equilibrated in buffer A with 5 mM DDPC. His-tagged human CD20 and murine CD20 were further purified over a 5 mL HITRAP HP Q™ column (Amersham Biosciences, Piscataway, N.J.) prior to gel filtration. For detergent exchange, samples were passed over a Superdex 200 column in buffer C, (0.1% DDM, 150 mM NaCl, 20 mM HEPES, pH 7.2.) Alternatively, samples were bound to a small Ni-NTA column, washed with buffer C and eluted with buffer C containing 300 mM imidazole. These samples were then dialyzed against buffer C to remove imidazole.

For affinity purification of human CD20, rituximab was immobilized at 6 mg/ml on 10 mL of Actigel ALD SUPERFLOW™ resin (Sterogene, Carlsbad, Calif.) This resin was placed in a column and equilibrated in buffer (0.1% DDM, 150 mM NaCl, 20 mM HEPES, pH 7.2). The human mutant CD20, C2S, was expressed and purified as described above for native human CD20. The purified C2S mutant was passed over the column and unbound protein was removed by extensive washing in buffer B. Protein was eluted in 0.1% DDM, 150 mM NaCl and 20 mM sodium citrate, pH 3.5. Eluted samples were immediately neutralized, concentrated and dialyzed against buffer C. Protein concentration was determined by BCA, as described in Smith et al., 1985, *Anal. Biochem.*, 150:76-85 (Pierce Biotechnology, Rockford, Ill. 61101). Samples were stored at −80° C. prior to use.

Density Gradient Centrifugation

A discontinuous sucrose gradient was generated by layering 1.9 M, 1.4 M, and 0.8 M sucrose solutions buffered with 150 mM NaCl and 20 mM HEPES, pH 7.2, in centrifuge tubes. Cells expressing the CD20 protein were lysed in buffer A containing 1 mM EDTA by cell disruption. The insoluble fraction was isolated by centrifugation at 38,000×g for 1 hour. The supernatant was discarded and the pellet resuspended in the lysis buffer with the addition of 0.25 M sucrose at a 1:5 wt/vol, 100 μL (microliter) of this resuspension was mixed with 0.9 mL of the 1.9 M sucrose solution. The resulting mixture had a final concentration of 1.75 M sucrose. This mixture was then placed at the bottom of a centrifuge tube and 1 mL of the remaining two sucrose solutions layered above. A final 200 μL (microliter) layer of the 0.25 M sucrose solution was then added to the top of the tubes. Samples were loaded into an SW55 rotor and spun for 1 hour at 100,000×g. Samples were then carefully unloaded in 200 μL (microliter) aliquots from the top of the tube and analyzed by SDS-PAGE, transferred to nitrocellulose, and probed with horseradish peroxidase conjugated anti-His antibody.

ELISA Assays

CD20 protein was coated onto 96 well plates overnight at 4° C. using 100 μL (microliter) of CD20 at 1 microgram/mL in PBS containing a solubilizing detergent diluted to below its critical micelle concentration. Plates were then washed three times with PBS containing 0.05% Tween-20 (PBST) and blocked for 45 minutes at room temperature with 200 μL of PBST containing 0.5% BSA (blocking and assay buffer). Plates were again washed three times with PBST and then probed with the primary antibody. A volume of 150 μL (microliter) of rituximab at 60 μg/mL microgram/mL in assay buffer was added to the appropriate wells and three fold serial dilutions were performed in the subsequent wells by taking 50 μL from the first well and mixing with 100 μL (microliter) of assay buffer in the next and subsequent wells to a final concentration of approximately 2 ng/mL.

After 90 minutes incubation at room temperature, the plates were washed with PBST and bound rituximab was detected with 100 μL of horseradish peroxidase conjugate goat anti-human F(ab')2 (Jackson ImmunoResearch Laboratories Inc, West Grove, Pa.) diluted 1:2000 in assay buffer, washed six times with PBST and developed with 100 μL/well of TMB Microwell Peroxidase Substrate System (KPL, Gaithersburg, Md.) mixed according to the manufacturers instructions. The reaction was halted by the addition of 100 μL/well of 1.0 M phosphoric acid and the absorbance measured at 450 nm using a plate reader.

Reduced and alkylated CD20 samples were prepared by reduction with 10 mM DTT and alkylation by addition of 25 mM iodoacetamide. The reaction was halted by a further addition of 100 mM DTT. Following each step, the reaction was allowed to proceed for 30-60 minutes at room temperature at pH 8.0. For reduction and re-oxidation, the CD20 sample was reduced with 10 mM DTT prior to plating and allowed to re-oxidize in the absence of DTT for several hours on the plate before antibody binding.

Surface Plasmon Resonance

Rituximab affinities and binding kinetics for isolated human CD20 proteins were determined using a BIAcore™-3000 instrument (BIAcore, Inc. Piscataway, N.J.). A CM5 sensor chip was activated for covalent coupling of rituximab or rituximab-Fab using N-ethyl-N'-(3-dimethylaminopropyl)-carbodiimide hydrochloride and N-hydroxysuccinimide according to the supplier's instructions. Rituximab or rituximab-Fab were diluted 5-10 fold to a concentration of 100 µg/mL in 10 mM sodium acetate, pH 5.0, and injected onto the activated chip. The remaining active coupling sites were blocked with 1 M ethanolamine. Intact rituximab was deposited at 8000-12000 RU and the rituximab-Fab was deposited at 4000-7000 RU.

For kinetic measurements, seven, two-fold dilutions (a total of eight samples) of human CD20 from a starting concentration of 5 µM in 0.1% DDM, 150 mM NaCl, and 20 mM HEPES, pH 7.2 at 25° C. were injected with a flow rate of 30 µL/minute for 100 seconds. Bound protein was allowed to dissociate for 720 seconds. At the end of each sample measurement, the sensor surfaces were regenerated by injection of 20 µL, of 10 mM HCl. After sensograms were corrected for signals from a reference flow, kinetics were calculated using a simple 1:1 model with BIAevaluation 3.0 (BIAcore).

Circular Dichroism (CD)

Detergent solutions of CD20 in either 0.1% DDPC or 0.1% DDM were prepared by dialysis against 100 mM sodium phosphate, pH 7.2, and either 0.1% DDPC or 0.1% DDM. Circular dichroism data were collected using an AVIV202 instrument on 2 to 5 µM protein samples in a 1 mm quartz cuvette; wavelength scans were performed at 25° C. over the indicated regions in 2 nm increments with 10 seconds averaging time. Data were plotted over the range from 185 to 285 nm except for samples containing β-mercaptoethanol. Since β-mercaptoethanol interferes with data collection at lower wavelengths, these data were truncated at 200 nm.

Scatchard Analysis of Rituximab IgG and Fab Binding to Normal Human B Cells

Equilibrium dissociation constants ($K_d$) were determined for rituximab IgG and for rituximab Fab fragment binding to B cells using radiolabeled protein. All dilutions were performed in binding assay buffer (DMEM media containing 0.5% bovine serum albumin, 25 mM HEPES, pH 7.2, and 0.01% sodium azide). Aliquots (0.05 mL) of rituximab $^{125}$I-IgG iodinated with Iodogen or $^{125}$I-Fab iodinated with Iodogen or lactoperoxidase were dispensed into test wells of a V-bottom 96-well microassay plate at a concentration of 0.005 or 0.05 nM respectively. Serial dilutions (0.05 mL) of cold antibody were added and mixed. Purified human B-cells (125,000 in 0.05 mL) were then added to the wells. The plates were sealed and incubated at room temperature for 24 hours, then centrifuged for 15 minutes at 2,500 RPM. The supernatant was aspirated and the cell pellet was washed and centrifuged. The supernatant was again aspirated, and the pellets were dissolved in 1N NaOH and transferred to tubes for gamma counting. The data were used for Scatchard analysis as described in Munson et al., 1980, *Anal. Biochem.*, 107:220-239 using the program Ligand as described in McPherson, 1983, *Comput. Programs. Biomed.*, 17:107-113.

Normal human B cells were isolated from 100 mL of heparinized normal human blood by negative selection using the RosetteSep™ B Cell Enrichment Cocktail (Stemcell Technologies, Vancouver, Canada) according to the manufacturer's protocol. B cells were further separated over Ficoll-Paque (Amersham Biosciences, Peapack, N.J.), and then isolated and washed in phosphate buffered saline. Any remaining red cells were lysed by a 30 second exposure to a hypotonic solution. The purified B cells were then adjusted to a concentration of 1-2 million cells per milliliter in binding buffer.

Expression of Membrane-Bound Human CD20 in *E. coli*

The primary structure of human CD20 is shown in FIG. 1. The proposed topology of CD20 is that of a tetra-spanning membrane protein with both termini in the cytoplasm. The two extracellular loops of CD20 are strikingly different in size. The first loop between helix one and helix two is extremely small and seems unlikely to protrude extensively from the membrane. The size of this loop is highly conserved in other members of the MS4A family (See, for example, Ishibashi et al., 2001, *Gene*, 264:87-93 and Liang et al., 2001, *Genomics*, 72:119-127).

The second loop between helix three and helix four is approximately 46 amino acids in length extending from the region of residue 140 to the region of residue 185 and contains one possible disulfide bond between residues 167 and 183. The size of this loop varies widely among the amino acid sequences of the genes in the MS4A family, although most of these sequences retain the ability to form an extracellular disulfide bond (Ishibashi et al., 2001, Supra and Liang et al., 2001, Supra). On the cytoplasmic side of the membrane in resting B cells, CD20 is phosphorylated (Valentine et al., 1989, 1989, *J. Biol. Chem.*, 264:11282-11287). Phosphorylation is increased in response to antibody crosslinking (Tedder et al., 1988, *J. Biol. Chem.*, 263:10009-10015). No other posttranslational modifications have been identified on CD20, and the human protein lacks any consensus N-glycosylation sites in the extracellular region.

To ascertain the structure of CD20 and the potential role of disulfide bond formation in antibody binding, His-tagged human CD20 protein was expressed in *E. coli* as described above. The potential for native expression of the protein in *E. coli* was evaluated by localizing the cellular expression of CD20 to the membrane by density gradient centrifugation and by testing protein solubility in native detergents.

Figure 2:
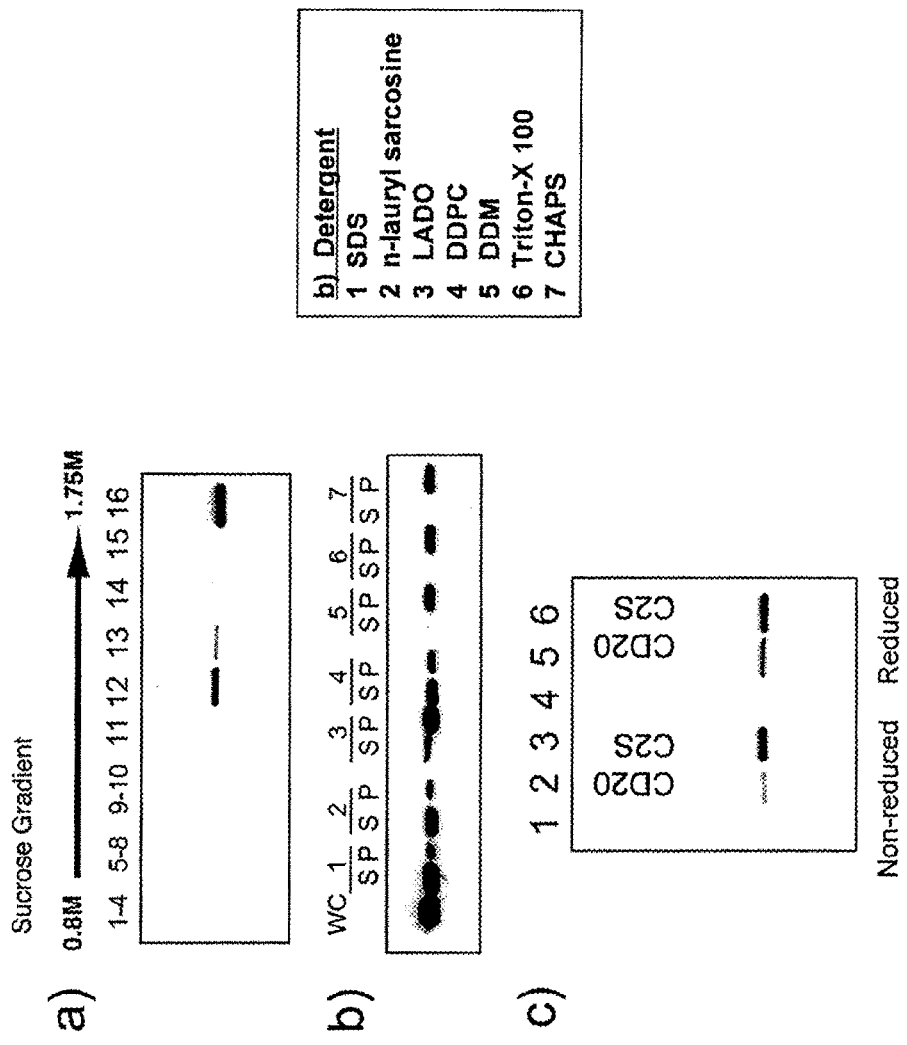
FIG. 2 shows anti-His-tag Western blot analysis of His-tagged CD20. Shown in panel a) are CD20-containing fractions following sucrose gradient flotation of *E. coli* cell membranes. Aliquots from the fractions (indicated by the top numbers) from the sucrose gradient were electrophoresed on an SDS-PAGE gel. The gel was blotted and probed with anti-His tag antibody. The fractions are from lowest sucrose density to highest. Panel b) shows levels of His-tagged CD20 on a Western blot after extraction of *E. coli* membranes with different detergents. Supernatants from the different detergent extractions are labeled (S) and pellets are labeled (P). (WC) denotes whole cell extract (control). Numbers 1-7 denote the different detergents tested, and are SDS (1), n-lauryl sarcosine (2), n-dodecyl-N,N-dimethylamine-N-oxide (LADO) (3), n-dodecylphosphocholine (DDPC) (4), n-dodecyl-β-D-maltoside (DDM) (5), Triton-X 100 (6), and 3-[(3-cholamidopropyl) dimethylammonio]-1-propanesulfonate (CHAPS) (7). Panel c) shows levels of His-tagged CD20 polypeptide detected from a Western blot with an anti-His tag antibody for *E. coli* cells expressing the His-tagged native human CD20 and C2S mutant CD20. Lanes 1 and 4 show control, empty vector, lanes 2 and 5 show His-tagged human CD20, and lanes 3 and 6 show C2S mutant CD20. Samples in lanes 1, 2, and 3 were run under non-reducing conditions; Samples in lanes 4, 5, and 6 were reduced with 100 mM DTT. Each lane contains an equal volume of cells normalized by optical density.

FIG. 2 shows the localization of isolated CD20 in the sucrose gradient. Fraction numbers 1-16 are indicated above the gel in panel a. Aliquots from the fractions from the sucrose gradient were electrophoresed on an SDS-PAGE gel. The gel was blotted and probed with anti-His tag antibody. The fractions are from lowest sucrose density (1) to highest (14). Approximately half of the total protein expressed in bacteria was found to be localized in a sucrose fraction (12) having a density less than 1.28 g/cm$^2$ (1.75 M sucrose) as shown in FIG. 2, panel a, while the remainder was found in the pellet (fraction 16).

Typical soluble proteins have a density of 1.33-1.42 g/cm$^2$ (Creighton, 1993, *Proteins Structures and Molecular Properties*, 2 Ed., W.H. Freeman and Company, New York, USA), which is greater than the density of the bottom layer of sucrose (1.28 g/cm$^2$, 1.75 M). Soluble proteins would be found at the bottom of the gradient, while membrane bound proteins float to a lower density due to the presence of lipid around the protein. These data shown in FIG. 2, panel a, are consistent with localization of human CD20 to a cellular membrane fraction of the bacteria, since *E. coli* membranes have a reported density of 1.15-1.25 g/cm$^2$ (Ishidate et al., 1986, *J. Biol. Chem.*, 261:428-443). These observations are also consistent with previous reports describing expression of other eukaryotic membrane proteins in a native conformation in the cellular membranes of bacteria (Bertin et al., 1992, *J. Biol. Chem.*, 267:8200-8206; Grisshammer et al., 1993, *Biochem J.*, 295(Pt2):571-576).

Detergent-Solubilization of CD20

Detergents useful for solubilization of CD20 were determined by screening an array of non-denaturing and denaturing detergents using the methods described above. Pellets and supernatants from *E. coli* cell membranes following detergent extraction were probed with anti-His antibody. FIG. 2, panel b shows the results of this screening. In the Western blot of human CD20, supernatants from the different detergents are labeled (S) while the pellets are labeled (P). (WC) denotes whole cell extract (control).

The various detergents used to extract protein from membranes are SDS (1), n-lauryl sarcosine (2), n-dodecyl-N,N-dimethylamine-N-oxide (LADO) (3), n-dodecylphosphocholine (DDPC) (4), n-dodecyl-β-D-maltoside (DDM) (5), Triton-X 100 (6), and CHAPS (7). As shown in the Western blot, soluble protein was obtained using a variety of detergents. A substantial fraction of CD20 was soluble in the non-denaturing zwitterionic detergent dodecyl phosphocholine (DDPC) (4). This detergent was selected for further work in extraction and purification of CD20.

His-tagged human CD20 was extracted from *E. coli* membranes with DDPC and purified by metal chelating, size exclusion, and anion exchange chromatographies as described above. Approximately 10-20 μg of purified His-tagged CD20 protein was obtained from one gram of bacterial cells.

Figure 3:
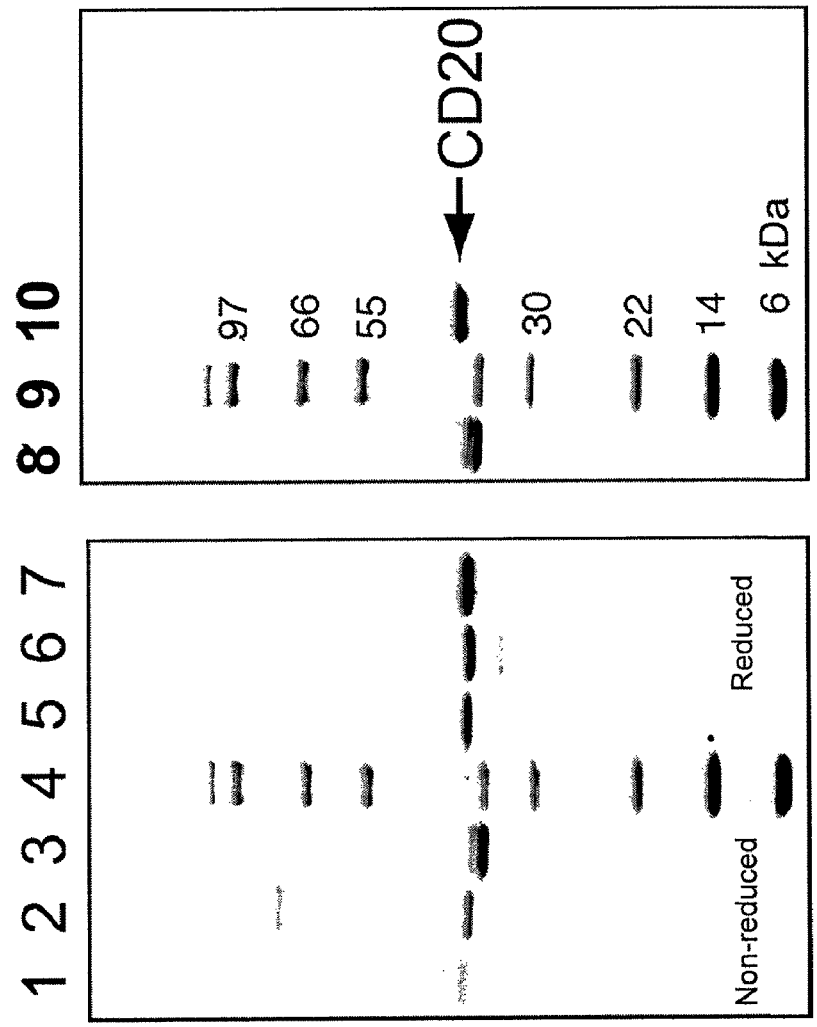
FIG. 3 shows Comassie-stained SDS gel lanes of purified human His-tagged human CD20, C2S mutant, and murine CD20. Lanes 1, 2, and 3 of panel a) contain non-reduced proteins: human CD20 (lane 1), C2S mutant (lane 2), and murine CD20 (lane 3). Lane 4 contains molecular weight markers (Mark 12, Invitrogen) Lanes 5, 6, and 7 show reduced proteins: human CD20 (lane 5), C2S mutant (lane 6), and murine CD20 (lane 7). Lanes 8 and 10 show non-reduced and reduced purified murine CD20, respectively. Lane 9 contains molecular weight markers. Each lane contains 2 μg (micrograms) of protein. Molecular weights of protein markers are 200, 116, 97, 66, 55, 36, 30, 22, 14, and 6 kDa.

FIG. 3 shows Coomassie-stained SDS gels lanes of the extracted and purified human His-tagged human CD20, C2S mutant, and murine CD20 Lanes 1, 2, and 3 show non-reduced proteins: human CD20 (lane 1), C2S mutant (lane 2), and murine CD20 (lane 3). Lane 4 contains molecular weight markers (Mark 12, Invitrogen). Lanes 5, 6, and 7 show reduced proteins: human CD20 (lane 5), C2S mutant (lane 6), and murine CD20 (lane 7). Lanes 8 and 10 show non-reduced (lane 8) and reduced (lane 10) murine CD20 adjacent to molecular weight markers (lane 9). Each lane contains 2 μg (micrograms) of protein. Molecular weights of protein markers are 200, 116, 97, 66, 55, 36, 30, 22, 14, and 6 kDa. A representative SDS-PAGE of the purified His-tagged human CD20 is shown in FIG. 3 (lanes 1 and 5.) The protein migrates with an apparent molecular weight of approximately 38 kDa under reducing conditions, which is in reasonable agreement with the calculated molecular weight of 35 kDa.

Purified CD20 also shows a modest change in mobility under non-reducing and reducing conditions on SDS-PAGE. This is clearly seen in FIG. 3, where reduced (lane 10) and non-reduced (lane 8) murine CD20 were run in neighboring lanes for emphasis. This change suggests that non-reduced CD20 exists in a more compact, faster migrating structure than the reduced form, due to the disulfide bond positioned in the large extracellular loop. This disulfide bond is abolished upon addition of reducing agent.

Although the detergents dodecyl maltoside (DDM) and LADO demonstrated only limited ability to solubilize CD20, large-scale purification was also attempted with these detergents to assess if detergent solubilization from *E. coli* was indeed accurately quantitated by Western blots using the conditions described above and shown in FIG. 2, panel b. Briefly, insoluble fractions of *E. coli* expressed, His-tagged human CD20 were extracted with 1% of the indicated detergent. The samples were centrifuged, and the pellets and supernatants were suspended in equal volumes of SDS buffer. Equal volumes of each sample were electrophoresed on SDS-PAGE under reducing conditions. For comparison, an equal volume of a whole cell fraction (WC) was suspended in SDS buffer after lysis, but without any manipulation.

Protein purified using either DDM or LADO was significantly less pure and the procedures yielded significantly less protein than purifications performed with DDPC. However, CD20 could be successfully exchanged into non-ionic detergents following purification, indicating that DDPC does not possess a unique ability to solubilize CD20.

Expression of Murine CD20

Murine CD20 was expressed and purified under similar conditions to those used to purify human CD20. Results of this purification are shown in FIG. 3, (lanes 3 and 7). The murine protein material was significantly better behaved than human CD20, showing less aggregation on non-reducing SDS gels (compare lanes 1 and 3, FIG. 3, and providing a higher final protein yield. Inspection of the primary sequence of murine and human CD20 showed that cysteine residue 111 (FIG. 1) in the human sequence is substituted with a serine in the murine protein. This substitution implies that Cys 111 is not essential for activity of CD20. Additionally, it has been shown that cysteine 220 is not essential for the activity of CD20, since substitution of Cys220 with alanine resulted in similar expression and antibody-dependent lipid raft association as compared to wild type protein when expressed in eukaryotic cells. See, for example, Polyak et al., 1998, *J. Immunol.*, 161:3242-3248.

TABLE 2

Human and Murine CD20

```
                10          20          30          40
hCD20   MTTPRNSVNG  TFPAEPMKGP  IAMQSGPKPL  FRRMSSLVGP
hC2S    MTTPRNSVNG  TFPAEPMKGP  IAMQSGPKPL  FRRMSSLVGP
muCD20  -------MSG  PFPAEPTKGP  LAMQPAPKVN  LKRTSSLVGP 50          60          70          80
hCD20   TQSFFMRESK  TLGAVQIMNG  LFHIALGGLL  MIPAGIYAPI
hC2S    TQSFFMRESK  TLGAVQIMNG  LFHIALGGLL  MIPAGIYAPI
muCD20  TQSFFMRESK  ALGAVQIMNG  LFHITLGGLL  MIPTGVFAPI 90         100         110         120
hCD20   CVTVWYPLWG  GIMYIISG-SL LAATEKNSRK  CLVKGKMIMN
hC2S    CVTVWYPLWG  GIMYIISG-SL LAATEKNSRK  SLVKGKMIMN
muCD20  CLSVWYPLWG  GIMYIISGSLL AAAAEKTSRK  SLVKAKVIMS 130         140         150         160
hCD20   SLSLFAAISG  MILSIMDILN  IKISHFLKME  SLNFIRAHTP
hC2S    SLSLFAAISG  MILSIMDILN  IKISHFLKME  SLNFIRAHTP
muCD20  SLSLFAAISG  IILSIMDILN  MTLSHFLKMR  RLELIQTSKP 170         180         190         200
hCD20   YINIYNCEPA  NPSEKNSPST  QYCYSIQSLF  LGILSVMLIF
hC2S    YINIYNCEPA  NPSEKNSPST  QYCYSIQSLF  LGILSVMLIF
muCD20  YVDIYDCEPS  NSSEKNSPST  QYCNSIQSVF  LGILSAMLIS 210         220         230         240
hCD20   AFFQELVIAG  IVENEWKRTC  SRPKSNIVLL  SAEEKKEQTI
hC2S    AFFQELVIAG  IVENEWKRTS  SRPKSNIVLL  SAEEKKEQTI
muCD20  AFFQKLVTAG  IVENEWKRMC  TRSKSNVVLL  SAGEKNEQTI 250         260         270         280
hCD20   EIKEEVVGLT  ETSSQPKNEE  DIEIIPIQEE  EEEETETNFP
hC2S    EIKEEVVGLT  ETSSQPKNEE  DIEIIPIQEE  EEEETETNFP
muCD20  KMKEEIIELS  GVSSQPKNEE  EIEIIPVQEE  EEEEAEINFP 290         298
hCD20   EPPQDQESSP  IENDSSP  (SEQ ID NO: 1)
hC2S    EPPQDQESSP  IENDSSP  (SEQ ID NO: 6)
muCD20  APPQEQESLP  VENEIAP  (SEQ ID NO: 3)
```

C2S Mutation

To assess expression and antibody binding of CD20, residues Cys111 and Cys220 were both mutated to substitute serine at these positions, forming the C2S mutant. The C2S mutant was expressed and purified as described above for His-tagged human CD20. The C2S mutant demonstrated improved protein behavior relative to the native protein, including decreased aggregation and increased yield.

Shown in panel c of FIG. 2 are samples of *E. coli* cell extracts demonstrating expression of His-tagged human CD20 and of the C2S mutant CD20. Lanes 1 and 4 contain control, empty vector; Lanes 2 and 5 contain human CD20; and Lanes 3 and 6 contain C2S mutant CD20. Samples in lanes 1, 2, and 3 were run under non-reducing conditions; Samples in lanes 4, 5, and 6 were reduced with 100 mM DTT. Each lane contains an equal volume of cells normalized by optical density.

The C2S mutant (lanes 3 and 6) was expressed at a higher level in *E. coli* and showed less disulfide-dependent aggregation than the native human CD20 (lanes 2 and 5). Less aggregation and approximately two-fold higher protein yield of the C2S mutant is also demonstrated in FIG. 3, panel a, where lanes 2 and 6 containing C2S are compared with native human CD20 (lanes 1 and 5) and murine CD20 (lanes 3 and 7).

Expressed rCD20 Binds Rituximab

Figure 4:
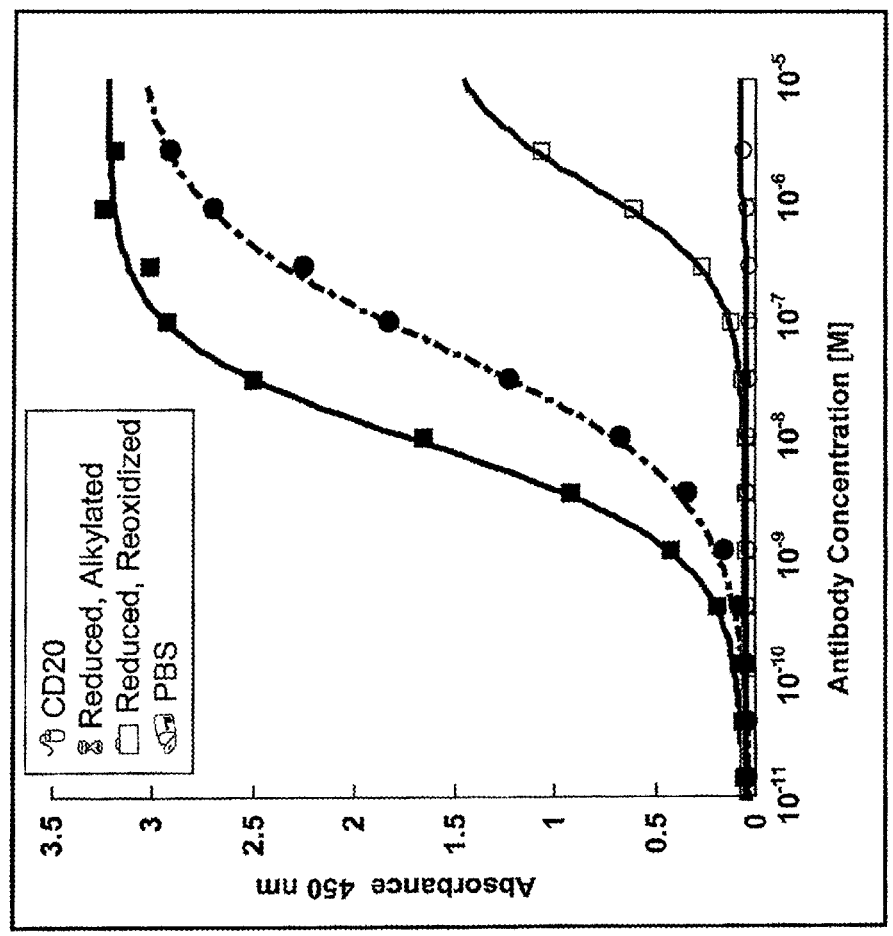
FIG. 4 is a graph showing disulfide-dependent rituximab antibody binding to His-tagged human CD20 (filled squares), reduced and alkylated hCD20 (filled circles), reduced and re-oxidized hCD20 (open squares), and PBS control (open circles).

To assess whether purified, recombinant CD20 adopts a native conformation, the ability of the purified protein to bind the chimeric anti-CD20 antibody rituximab was analyzed. This antibody is known to bind to a structurally-constrained extracellular loop of human CD20 expressed on the surface of B cells (Polyak et al., 2002, *Blood,* 99:3256-3262). An ELISA assay was developed based on binding of rituximab to purified human CD20. Results are shown in FIG. 4, a graph showing disulfide-dependent rituximab antibody binding to His-tagged human CD20 (filled squares), reduced and alkylated hCD20 (open squares), reduced and re-oxidized hCD20 (filled circles), and PBS control (open circles). The curves through the points for rituximab binding were determined from a 4-parameter fit analysis.

As shown in FIG. 4, rituximab binds His-tagged human CD20 with nanomolar affinities in this assay. An $EC_{50}$ of 9.4 nM was determined from a 4-parameter fit of the data.

Reduced rCD20 Fails to Bind Rituximab in ELISA

Rituximab binding has been localized to the extracellular loop of CD20 between residues K142 and Y184 (Polyak et al., 2002, Supra). Two residues in this region, C167 and C183, are thought to form a disulfide bond (Einfeld et al., 1988, *EMBO J.,* 7:711-717). Rituximab binding, in turn, is thought to be critically dependent upon the presence of this disulfide bond. To evaluate the importance of any disulfide bond in CD20 for the binding of rituximab, CD20 was reduced and alkylated and assayed for rituximab binding. This procedure substantially reduced the ability of rituximab to bind CD20. As an additional control, CD20 was reduced, DTT was removed and the protein was allowed to re-oxidize. Rituximab binding was partially restored in this procedure, consistent with the reformation of the disulfide bond in CD20, thus demonstrating that antibody binding is dependent on disulfide bond formation. As antibodies for the extracellular region of murine CD20 are currently unavailable, it was not possible to develop a similar assay for murine CD20.

BIAcore Assay of rhCD20 and C2S Mutant

The ELISA assay of CD20 described above could allow for avidity effects in antibody binding. In order to evaluate the binding of rituximab to human CD20 independent of such effects surface plasmon resonance analysis was performed. This technique has the added advantage of providing both kinetic binding information and equilibrium binding constants. In these experiments, rituximab or rituximab Fab was deposited on a BIAcore sensor chip and soluble human CD20 was passed over the chip at various concentrations. Full length rituximab was deposited at 10,000 RU and human CD20 at the indicated concentrations was applied to the sensor chip at a flow rate of 20 μL/minute in 150 mM NaCl, 20 mM HEPES (pH 7.2), and 0.1% DDM.

Interestingly, although CD20 could be isolated in DDPC, binding of CD20 to immobilized rituximab was significantly reduced in the presence of this detergent (data not shown.) Therefore, affinities from surface plasmon resonance experiments were determined in the presence of DDM.

Figure 5:
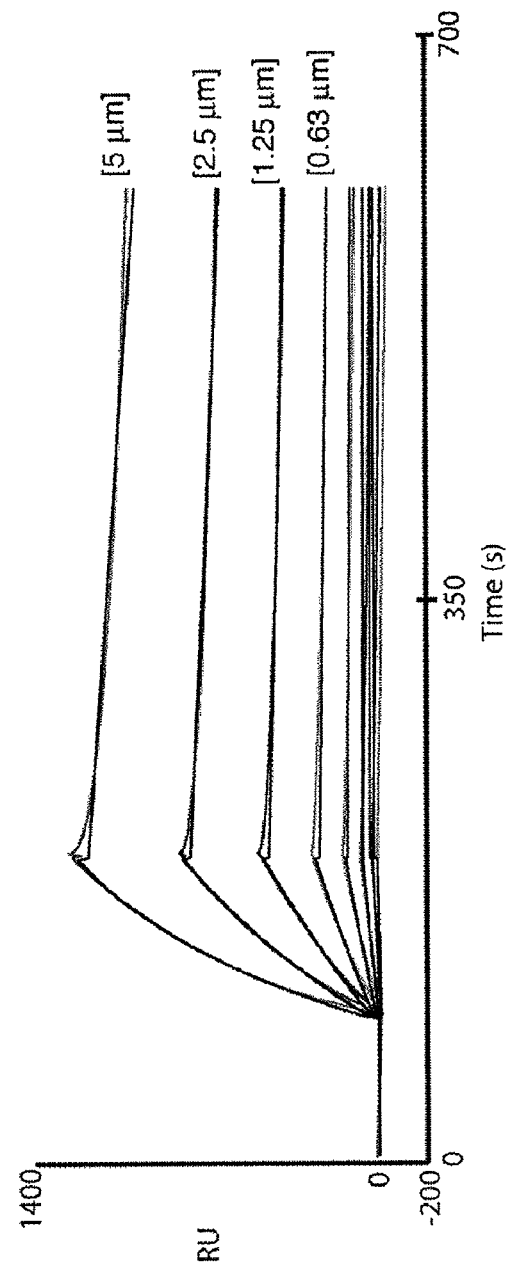
FIG. 5 is a BIAcore sensogram showing binding between rituximab and human His-tagged CD20. Binding of human CD20 to immobilized rituximab occurs at CD20 concentrations of 5 μM, 2.5 μM, 1.25 μM, 0.63 μM, 0.31 μM, 0.16 μM, 0.08 μM, and 0.04 μM. Concentrations for the first 4 samples are labeled on the sensogram. The calculated theoretical fit to a non-cooperative model is shown at each concentration.

Representative data from these experiments can be seen in FIG. 5, a BIAcore sensogram showing binding between rituximab and human His-tagged CD20. Binding of human CD20 to immobilized rituximab occurs at CD20 concentrations ranging from 0.04 μM to 5.0 μM, and including 5 μM, 2.5 μM, 1.25 μM, 0.63 μM, 0.31 μM, 0.16 μM, 0.08 μM, and 0.04 μM. Concentrations for the first 4 samples are labeled on the sensogram. Binding of rituximab is shown for non-reduced CD20 (filled squares), reduced and alkylated CD20 (filled circles), reduced CD20 that was permitted to reoxidize (open squares) and control PBS (open circles). The binding curves were determined from a four parameter fit analysis. The calculated theoretical fit to a non-cooperative model is shown at each concentration.

In Table 3, the binding parameters of rituximab IgG or Fab with human CD20, C2S mutant, and affinity purified C2S mutant are shown. Data are representative of multiple experiments and are fit to a single binding site model. $K_d$ and $K_a$ values are calculated from association and dissociation rates. From this table it can be seen that both His-tagged human CD20 and the C2S mutant of human CD20 exhibit approximately the same binding properties with both full-length rituximab antibody and the Fab fragment. The data demonstrate that the Cys-to-Ser mutations of CD20 did not alter antibody binding, for example, did not alter "native" conformation needed for antibody binding.

TABLE 3

| CD20 sample | $k_{on}/10^3$ ($M^{-1} s^{-1}$) | $k_{off}/10^{-4}$ ($s^{-1}$) | $K_a/10^6$ ($M^{-1}$) | $K_d/10^{-9}$ (M) |
| --- | --- | --- | --- | --- |
| Rituximab full length antibody | | | | |
| CD20 | 2.5 | 4.1 | 6.6 | 160 |
| C2S-CD20 | 4.5 | 7.6 | 5.9 | 170 |
| affinity purified C2S-CD20 | 8.7 | 7.3 | 12 | 84 |
| Rituximab Fab | | | | |
| CD20 | 1.7 | 4.8 | 3.5 | 280 |
| C2S-CD20 | 4.9 | 11 | 4.4 | 230 |
| affinity purified C2S-CD20 | 7.4 | 14 | 5.4 | 190 | hCD20 Expressed in *E. coli* is in "Native" Conformation

In order to determine the percentage of CD20 that is present in our preparations with the proper conformation for antibody binding, we further purified the C2S mutant of human CD20 over a rituximab affinity column. Although the yields were low, the binding data before and after affinity purification are in general agreement, demonstrating that the majority of purified human CD20 is in a conformation capable of binding rituximab. A modest improvement in antibody binding was demonstrated after affinity purification with immobilized rituximab. This improved affinity may be due to either improved purity of CD20 or removal of inactive CD20 molecules. A small difference in affinity of CD20 for full-length antibody relative to the Fab was observed. This slight difference may be accounted for by surface effects due to coupling of the smaller Fab fragment to the sensor chip or to minor changes in the structure of the Fab after removal of the Fc region.

It is possible that any CD20 aggregated in the detergent micelle may contribute an avidity effect to the affinity of both IgG and Fab binding. Although the influence of avidity effects are difficult to rule out, these are not believed to contribute significantly to the binding observed in this assay for two reasons. First, affinities of the soluble CD20 for intact rituximab IgG or Fab fragment show less than two fold differences. Even if Fab binding were to allow for some avidity effects due to proximity of the Fab fragments on the sensor chip, it is unlikely that random coupling and orientation of the Fab fragment would allow for such a close agreement in measurement. In addition, both the IgG data and the Fab data show excellent agreement to the theoretical fit predicted for monovalent binding. Divergence from theoretical monovalent binding should be particularly evident for the IgG BIAcore experiment, however, as shown in FIG. 5, the theoretical monovalent fit and the actual experimental data for CD20 binding to rituximab IgG are in very close agreement. Thus, no additional binding modes need be postulated to account for the experimental data.

Figure 7:
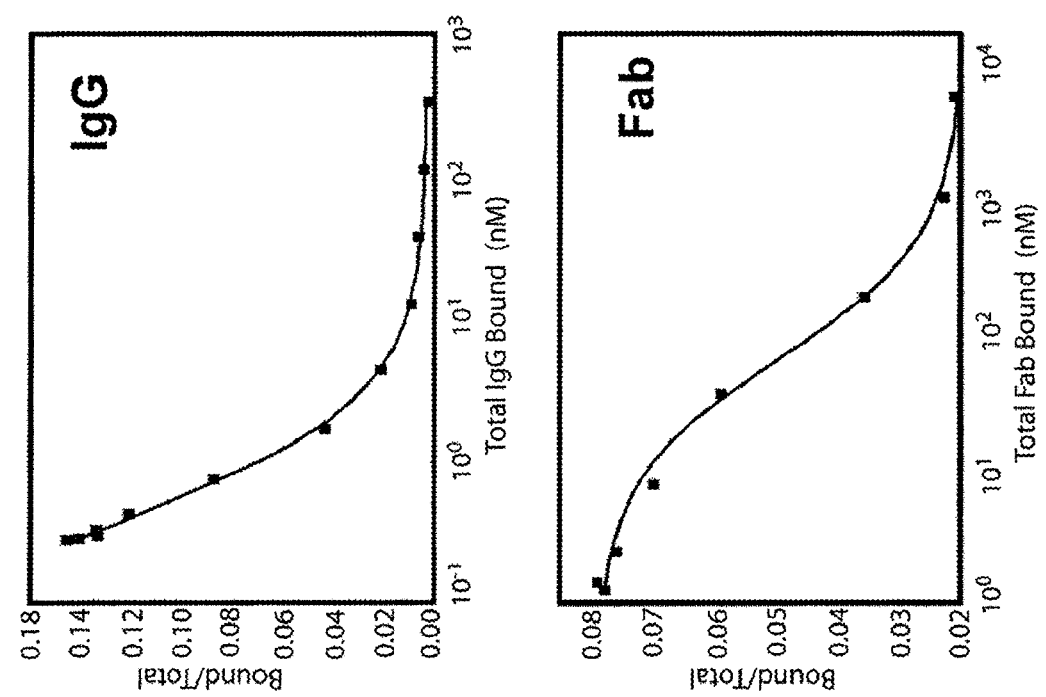
FIG. 7 shows typical displacement plots of rituximab IgG and Fab binding to isolated normal human B cells. The $EC_{50}$ for native CD20 in this assay was 9.5 nM.

Second, affinity measurements of both the rituximab IgG and Fab fragment, as determined by BIAcore, are in close agreement to the affinity measurements of the rituximab Fab fragment determined from Scatchard analysis of binding on normal human B cells. Binding of rituximab IgG or Fab to normal human B cells was determined by competition for unlabeled rituximab IgG or Fab against $^{125}$I-IgG or $^{125}$I-Fab. The data shown are the average of analysis on normal cells from two donors. Typical displacement plots of the binding experiments of rituximab IgG and Fab are shown in FIG. 7. Binding was determined by competition of unlabeled rituximab IgG against $^{125}$I-IgG for donor 1 (upper panel) or unlabeled rituximab Fab against $^{125}$I-Fab for donor 4 (lower panel). Each measurement was performed in triplicate on cells from a single donor. Table 4 shows affinities and number of receptors from each donor. The $EC_{50}$ for native CD20 in this assay was 9.5 nM.

TABLE 4

Rituximab IgG

| Human B cells | Rituximab IgG $K_d/10^{-9}$ (M) | Number of Receptors per cell ($10^3$) |
|---|---|---|
| Donor 1 | 0.32 +/− 0.053 | 160 +/− 12 |
| Donor 2 | 0.72 +/− 0.21 | 35 +/− 4.8 |
| Donor 3 | 1.27 +/− 0.39 | 45 +/− 8.1 |

Rituximab Fab

| Human B cells | Rituximab Fab $K_d/10^{-9}$ (M) | Number of Receptors per cell ($10^3$) |
|---|---|---|
| Donor 4 | 52 +/− 5.1 | 570 +/− 52 |
| Donor 5 | 63 +/− 23 | 230 +/− 75 |

The data demonstrates a small, three to four fold difference exists between the monovalent affinity of rituximab Fab for isolated human CD20 as determined by BIAcore and the monovalent affinity of rituximab Fab for CD20 expressed on isolated human B-cells (190-280 nM affinities in the BIAcore experiments verses 50-60 nM affinities from Scatchard analysis). This small difference may represent inherent differences in the assay methods, physical differences in the protein environment, the presence of detergent, or the lack of CD20 binding partners in the isolated material, among other causes. It is interesting to note the large difference between rituximab IgG and Fab binding to B cells. This suggests that avidity effects may play a role in the binding of rituximab to B cells.

As would be expected from the Kd of rituximab for human CD20 (84-170 nM), the association and dissociation binding rates are relatively rapid, particularly in comparison to high affinity antibodies such as the affinity-matured anti-VEGF antibody (Chen et al., 1999, *J. Mol. Biol.*, 293:865-881 that has a Kd of less than 0.15 nM, a kon of 3.6×104 (M−1 s−1), and a koff of less than or equal to 0.05×10−4 (s−1) at 25° C. However, as the affinities of rituximab IgG or rituximab Fab fragment determined by BIAcore for isolated CD20 are in close agreement with the rituximab Fab affinity determined from Scatchard analysis on normal B cells, it seems likely that the low monovalent affinity value is realistic and does not result from significant amounts of misfolded or non-native conformations being present in isolated hCD20 preparations.

Analysis of Secondary Structure by Circular Dichroism

Figure 6:
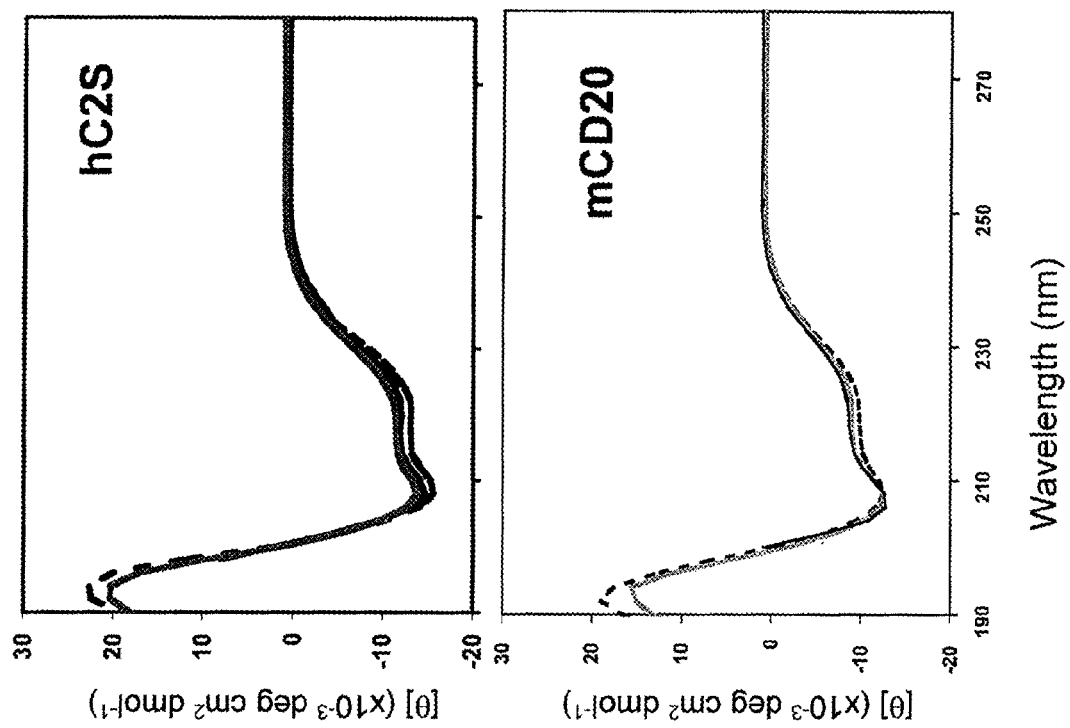
FIG. 6 shows far-ultraviolet circular dichroic spectra of CD20 proteins. Shown in panel (a) are spectra for human CD20 mutant C2S in the presence of 0.1% DDPC (black line); in 0.1% DDPC and 10 mM β-mercaptoethanol (dashed line), and after thermal scan to 95° C. in the presence of 1% SDS (gray line). Shown in panel (b) are spectra for murine CD20 in the presence of 0.1% DDPC (dashed line), 0.1% dodecyl-maltoside (DDM) (gray line); and in 0.1% DDM with the addition of 1% SDS and β-mercaptoethanol and after heating for 2 minutes at 95° C. (black line). Data are expressed as molar ellipticities.

CD20 was further analyzed for secondary structure by circular dichroism spectroscopy (CD) of human C2S, and murine CD20. Sample spectra from this analysis are shown in FIG. 6.

Shown in the upper panel are spectra for the human CD20 mutant C2S in the presence of 0.1% DDPC (black line); in 0.1% DDPC and 10 mM β-mercaptoethanol (dashed line), and after thermal scan to 95° C. in the presence of 1% SDS (dotted line). Shown in the lower panel are spectra for murine CD20 in the presence of 0.1% DDPC (dashed line), 0.1% dodecyl-maltoside (DDM) (dotted line); and in 0.1% DDM with the addition of 1% SDS and ε-mercaptoethanol and after heating for 2 minutes at 95° C. (black line). Data are expressed as molar ellipticities.

On the basis of the predicted topology of CD20 as a tetraspanning membrane protein, CD20 should have a helical content of approximately 35%. It can be seen that both the C2S mutant of human CD20 (FIG. 6, upper panel) and murine CD20 (FIG. 6, lower panel) demonstrate a significant signal in the 222 nm region of the spectra as would be expected for proteins with significant alpha helical component. The addition of reducing agent did not significantly alter the secondary structure of either murine (lower panel b, black line) or the C2S mutant of human CD20 in either the presence of DDPC (upper panel, dashed line) or SDS (upper panel, thin line). Further, the secondary structure of CD20 appears to be very stable in a broad variety of detergents and temperatures. CD spectra of the C2S mutant of human CD20 in the presence of SDS (upper panel, thin line) or murine CD20 in the presence of SDS and reducing agent (lower panel, black line), after a thermal scan or brief heating, are almost identical to spectra of the native proteins (see FIG. 6). Data are expressed as molar ellipticities.

A temperature scan from 25° C. to 95° C. demonstrates that human CD20 loses approximately 35% of the 222 nm helical signal at 95° C. (data not shown). Although there is no evidence of cooperative unfolding or cooperative refolding, the majority of this signal is recovered when the sample is returned to lower temperatures, at least following brief heating (FIG. 6.) The small difference in heated and unheated human CD20 samples may indicate that some structure is lost permanently and, the amount of permanently denatured protein could potentially increase with longer exposure to heat. Addition of reducing agent to murine CD20 did not significantly affect thermal stability of the protein in SDS (panel b, black line). It is possible that the disulfide bond, positioned outside the regions of CD20 that are predicted to have alpha helical structure, may contribute very little to the over all structural stability of CD20. It is also likely that changes to the structure of CD20 resulting from reduction of the disulfide bond are simply not observable by CD. It has been previously noted that reduction of the disulfide bond of the β2 adrenergic receptor also had limited effects on secondary structure as measured by CD (Lin et al., 1996, *Biochemistry*, 35:14445-14441). Similarly, the secondary structure of diacylglycerol kinase is not affected by SDS under conditions similar to those used here (Lau et al., 1997, *Biochemistry*, 36:5884-5892).

Example 2

Expression of MS4A Proteins with phoA Promoter

Additional members of the MS4A family of tetra-membrane-spanning polypeptides were expressed in *E. coli* under control of the phoA promoter in the manner described above for Example 1. The gene products MS4A4A (SEQ ID NO: 10), MS4A6A (SEQ ID NO: 12), and MS4A7 (SEQ ID NO: 14) were expressed in *E. coli* according to the methods described above for Example 1. High quantities of protein were obtained from the cells, as detected using anti-His immunoblots. As shown in FIG. 8, the detected MS4A polypeptides were close in molecular weight to the predicted molecular weights posited by Liang and Tedder (2001, *Genomics* 72: 119-127):

| MS4A4A | MS4A6A | MS4A7 |
|---|---|---|
| 27 kDa | 29 kDa | 23 kDa |

Example 3

Mutation of the phoA Promoter

The *E. coli* promoter, phoA, was selected for use in expressing complex membrane-spanning proteins including the MS4A family of tetra-membrane-spanning proteins such as CD20. As shown below in Table 5, the phoA promoter includes typical promoter elements such as the translation initiation site

ATG,

-10 TATA box

TATAGT, and a pho box

GCTGTCATAA AGTTGTCAC (SEQ ID NO: E20).

The expression of mammalian multi-spanning membrane proteins in *E. coli* is generally considered challenging (see, for example, Grisshammer, R., 1998, In: *Identification and Expression of G Protein-Coupled Receptors*, pp 133-150, Ed. K. R. Lynch, Wiley-Liss Inc.; Laage et al., 2001, *Traffic* 2:99-104). Some of these proteins are very toxic to bacterial cells even when expressed at very low levels, which adds further complexity to their production and isolation. Simply transforming expression constructs for these proteins into pertinent expression strains often results in colonies of abnormally small or variable size, suggesting toxicity to the cell even when the promoter is turned off. Basal level expression of these proteins due to low levels of transcription can also lead to poor bacterial growth in rich media, resulting in poor cell physiology prior to fully turning on the promoter. The end result is often variable expression from one experiment to the next, as well as low protein yields. As shown below, production of such proteins in a host cell requires a tightly controlled promoter to limit the extent of basal protein expression in the cells.

To preclude basal level transcription, two new controllable promoters were created from the basic sequence and regulatory elements of the *E. coli* phoA promoter (Kikuchi, et al., 1981, *Nucl. Acids Res.* 9:5671-5678). The wild type phoA promoter is normally controlled by the binding of the protein phoB in its phosphorylated form to the pho box just upstream of the −10 or Pribnow box. Binding leads RNA polymerase to also bind and start the transcription process from this promoter. PhoB in turn is phosphorylated at the cytoplasmic membrane in response to low phosphate concentrations in the periplasm and the media (Wanner, 1996, *Escherichia coli and Salmonella*, Neidhardt (ed.), p. 1357-1381). The binding of phosphorylated phoB to the promoter in response to low levels of phosphate in the media represents positive regulation of the phoA promoter. In the absence of phosphorylated phoB, RNA polymerase may still bind weakly to the phoA promoter using the −10 sequence and some weak −35 sequence for contact instead, resulting in low basal levels of transcription.

To inhibit RNA polymerase from binding to the phoA promoter in the absence of phosphorylated phoB, a negative regulatory element, here the lac operator sequence AATTGT-GAG CGGATAACAA (SEQ ID NO: 18) (Gilbert et al., 1973, *Proc. Natl. Acad. Sci. USA* 70:3581-3584), was inserted upstream from the +1 transcription start position, as shown in Table 5. This addition reduced transcription from the phoA promoter when phosphate was present (or absent) in significant concentrations in the media (See FIG. 9).

The newly created promoter, phac, has both positive and negative regulation via the positive control element (phoB binding pho box) and the added negative control element, the lac operator. The phac promoter must be induced by phosphate starvation, as well as relieved from lac repressor control by the addition of inducers such as isopropyl β-D-thiogalactoside (IPTG). The addition of the lac operator control sequence to other promoters has been reported (De Boer et al. 1983, *Proc. Natl. Acad. Sci, USA,* 80:21-25; Yansura et al., 1984, *Proc. Natl. Acad. Sci. USA,* 81:439-443), however, in these promoters the lac operator sequence was used to replace a negative control elements that was difficult to manipulate, or was added to constitutive promoters to provide new controls.

A second possible source of basal transcription to be controlled is from promoters upstream of the promoter used to drive expression of the membrane protein of interest. Such promoters have been mapped, for example, on the plasmid pBR322, most often used for construction of E. coli vectors. Promoters upstream of phoA can potentially cause basal levels of transcription due to "read-through". To prevent upstream transcription from proceeding through the phac promoter and coding sequence of some membrane protein, a transcriptional terminator, here the lambda $t_0$ transcriptional terminator:
AACGCTCGGTTGCCGCCGGGCGTTTTTTATT(SEQ ID NO: 17) (Scholtissek et al., 1987, Nucl. Acids Res., 15: 3185) was inserted upstream of the pho box in the correct orientation within the added upstream sequence: AGGCCT AACGCTCGGTTGCCGCCGGGCGTTTTTTATTGTT AACCATGGA (SEQ ID NO. 19). The new promoter, tphac, is induced in the same way as the phac promoter, for example, by dilution into phosphate-limiting media and by addition of IPTG (data not shown). Basal level transcription was further reduced using tphac as compared with phac.

TABLE 5

Comparison of phoA promoter and mutants phoA . . .

phac . . .

tphac AGGCCTAACG CTCGGTTGCC GCCGGGCGTT TTTTATTGTT AACCATGGA

```
                      60
phoA  GCGATTACGT AAAGAAGTTA TTGAAGCATC CTCGTCAGTA
AAAAGTTAAT CTTTTCAACA phac  GCGATTACGT AAAGAAGTTA TTGAAGCATC CTCGTCAGTA
AAAAGTTAAT CTTTTCAACA tphac GCGATTACGT AAAGAAGTTA TTGAAGCATC CTCGTCAGTA
AAAAGTTAAT CTTTTCAACA
                      120
phoA  GCTGTCATAA AGTTGTCAC G GCCGAGACT T ATAGT CGCTT
TGTTTTTATT TTTTAATGTA phac  GCTGTCATAA AGTTGTCAC G GCCGAGACT T ATAGT CGCTT
TAATTGTGAG CGGATAACAA tphac GCTGTCATAA AGTTGTCAC G GCCGAGACT T ATAGT CGCTT
TAATTGTGAG CGGATAACAA
                      167
phoA  TTTGTAACTA GTACGCAAGT TCACGTAAAA AGGGTATCTA
GAATT ATG (SEQ ID NO:5)

phac  TTTGTAACTA GTACGCAAGT TCACGTAAAA AGGGTATCTA
GAATT ATG (SEQ ID NO: 15)

tphac TTTGTAACTA GTACGCAAGT TCACGTAAAA AGGGTATCTA
GAATT ATG (SEQ ID NO:16)
```

TABLE 5-continued

Comparison of phoA promoter and mutants

ATG_start of translation

TATAGT -10 box

GCTGTCATAA AGTTGTCAC Pho Box (SEQ ID NO: 20)

AATTGTGAG CGGATAACAA lac operator for negative control (SEQ ID NO:18)

AACG CTCGGTTGCC GCCGGGCGTT TTTTATT Lambda transcriptional terminator (SEQ ID NO:17)

Example 4 phoA vs. phac for Expressing RA1c

To test the impact of the phoA mutant promoter phac on expression and yield of complex membrane-spanning polypeptides in bacterial host cells, recombinant RA1c with an N-terminal leader, MKHQHQQ (SEQ ID NO: 7) for efficient translation initiation, and two C-terminal tags, Flag and 6-His were engineered into expression vectors and operably linked to the phoA promoter (vector pEfRA1c) and to the phac promoter (vector pEfRA1cr). RA1c is a membrane-spanning polypeptide having seven transmembrane segments.

Transformation

Both plasmids expressed human RA1c (Kretschmer et al., 2001, Gene 278:41-51). Plasmids were transformed into the E. coli strain 58F3 (W3110-fhuAΔ(tonAΔ) phoAΔE15 IonΔ galE rpoHts(htpRts) ΔclpP lacIq ΔompTΔ(nmpc-fepE) ΔslyD) and selected transformant picks were inoculated into 5 mL Luria-Bertani medium supplemented with carbenicillin (50 μg/mL) and grown at 30° C. on a culture wheel for approximately 14-16 hours. The $OD_{600}$ of the culture with pEfRA1c (phoA promoter) was 1.55 and the culture with pEfRA1cr (phac promoter) was 3.57. A 1 $OD_{600}$-mL sample from the LB inoculum was collected.

Shake flask inductions were carried out. Each culture was then diluted (1:100) into C.R.A.P. phosphate-limiting media (Simmons et al., 2002, J. Immunol. Methods 263:133-147) with 50 μg/mL of carbenicillin. All cultures were grown at 30° C. in a two liter baffled flask with the 500 mL final induction volume on a shaker with approximately 200 rpm speed. A 1 $OD_{600}$-mL sample was collected at 10, 12, 14, 16, 18, 22, and 24 hours post inoculation into the C.R.A.P. media for the pEfRA1c culture (phoA promoter). For cultures expressing pEfRA1cr (phac promoter), 1 mM IPTG was added into the C.R.A.P. media at 10 and 12 hours post inoculation to release the lac repressor control. Respective $OD_{600}$ of the culture at IPTG inductions were 2.79 and 2.97. A 1 $OD_{600}$-mL sample was collected before IPTG addition and every two hours post IPTG addition up to the $24^{th}$ hour for all the IPTG induced cultures.

For Western blot analysis, reduced whole cell lysates of the 1 $OD_{600}$-mL samples were prepared as follows:

1 $OD_{600}$-mL samples were centrifuged in a microfuge tube.

Each pellet was resuspended in 100 μL TE (10 mM Tris pH 7.6, 1 mM EDTA).

To reduce disulfide bonds, 10 µL of 1M dithiothreitol (Sigma D-5545) was added to each sample.

20 µL of 20% SDS was added to each sample.

The samples were vortexed, heated at 90° C. for 5 minutes and then vortexed again. After the samples had cooled to room temperature, 800 µL acetone was added to precipitate the protein. The samples were vortexed and left at room temperature for 15 minutes. Following centrifugation for 5 minutes in a microcentrifuge, the supernatant of each sample was aspirated off and each protein pellet was resuspended in 10 µL 1M dithiothreitol plus 40 µL dH$_2$O and 50 µL 2× NOVEX SDS sample buffer. The samples were then heated for 5 minutes at 90° C., vortexed well and allowed to cool to room temperature. A final 5 minute centrifugation was then performed, and the supernatants were transferred to clean tubes.

Following SDS sample preparation, inoculum samples of 8 µL of the pre-induction samples were loaded onto a 10 well, 1.0 mm NOVEX16% Tris-Glycine SDS-PAGE and electrophoresed at approximately 120 volts for about 1.5 hours. Samples induced in C.R.A.P. media (pEfRA1c) were prepared in the same manner. For samples induced both in C.R.A.P. media and with IPTG (pEfRA1cr samples), 5.3 µL was loaded onto a 15 well gel. The resulting gels were then used for Western blot analysis.

Western Blot Analysis

The SDS-PAGE gels were electroblotted onto nitrocellulose membranes (NOVEX) in 20 mM Sodium Phosphate buffer, pH 6.5. Membranes were then blocked using a solution of 1×NET (150 mM NaCl, 5 mM EDTA, 50 mM Tris, pH 7.4, 0.05% Triton X-100)+0.5% gelatin for approximately 30 minutes to one hour on a rocker at room temperature. Following the blocking step, membranes were placed in a solution of 1×NET+0.5% gelatin+anti-His antibody (Anti-his6 Peroxidase conjugated mouse monoclonal antibody from Roche Diagnostics) for anti-His Western blot analysis. The anti-His antibody dilution was 1:5000 and the membranes were left in the antibody solution overnight at room temperature with rocking. The next morning, the membranes were washed a minimum of 3×10 minutes in 1×NET and then 1×15 minutes in TBS (20 mM Tris pH 7.5, 500 mM NaCl). The protein bands bound by the anti-His antibody were visualized using Amersham Pharmacia Biotech ECL detection and exposing the membrane to X-Ray film.

The effect of the phac promoter is shown as early as the plasmid transformation step. Transformants from pEfRA1c (phoA) and pEfRA1cr (phac) were compared after overnight growth on LB plates. Cells transformed with pEfRA1cr (phac) were significantly larger than the cells with pEfRA1c (data not shown). FIG. 9 shows anti-His Western blot analysis for samples of colonies streaked from the plates and inoculated in LB/Carb for approximately 14-16 hours. As shown in the middle lane of the blot, expression of RA1c from the non-induced phoA promoter (pEfRA1c), suggests leakage from the phoA promoter when phosphate was not limiting. In contrast, no detected RA1c expression was seen from the tightly controlled phac promoter (pEfRA1cr).

Basal level expression of the multi-transmembrane protein RA1c from the phoA promoter was toxic to the cell, causing poor growth in LB, and resulting in overall low cell density. The OD$_{600}$ reading of the overnight LB inoculums improved from 1.55 in pEfRA1c to 3.57 in pEfRA1cr, indicating healthier cells with the phac promoter.

The time course of expression results for pEfRA1c (phoA promoter) are shown in FIG. 10. The phosphate in the culture was expected to deplete by about 2.0 OD$_{600}$. Expression was detected as early as the 10$^{th}$ hour, with an OD$_{600}$ reading of 1.73. A very narrow production window of approximately 2 hours occurred from 12$^{th}$ to 14$^{th}$ hour post induction, but production thereafter slowly disappeared. By the 24$^{th}$ hour post induction, the monomeric band of expressed protein had completely disappeared. In addition, as the monomeric band disappeared over time, the non-reducible aggregate in the smear accumulated. The highest cell density while maintaining the most protein in the monomeric band was 2.51 OD$_{600}$ at the 14$^{th}$ hour (* in FIG. 10).

Optimally, the phac promoter should be completely shut off until the time of induction by phosphate depletion in the C.R.A.P. media. The time course of RA1c expression resulting from IPTG-induced phac promoter (pEfRA1cr) cultures is shown in FIG. 11. The maximum protein production was reached within two hours post IPTG addition and a similar expression pattern of the monomeric band and the smear was observed. The culture induced at the 12th hour showed better expression than that induced at the 10$^{th}$ hour, indicating the importance of the induction time. Most importantly, the phac promoter provided the advantage of keeping the cells healthier so they could grow to a higher density by keeping the promoter totally turned off until needed. Upon induction, cells undergo stress and stop growing, and eventually the cell density drops. The 12$^{th}$ hour culture before adding IPTG had already started to express RA1c, presumably due to partial induction of the phac promoter as a result of phosphate depletion. If IPTG were to be added any later than the 12$^{th}$ hour, the phac promoter may become less useful. Thus, under these culture conditions, IPTG addition at the 12$^{th}$ hour appears to be the latest point to take advantage of the phac promoter. Maximum protein production was achieved two hours post IPTG induction (12$^{th}$ hour) at hour 14. The OD$_{600}$ at hour 14 was 2.97 with the phac promoter, greater than 2.51 obtained with the phoA promoter.

A comparison of overall expression of RA1c with the phoA promoter and phac promoter is shown in FIG. 12. The best expression results from the phoA and phac promoters are presented on the same blot to make a direct comparison. It is clear that the two-hour induction of RA1c with the phac promoter at the 12$^{th}$ hour (right lane) yields higher protein expression and higher cell density than the highest expression from the phoA promoter at the 14th hour (left lane).

Example 5 phoA vs. phac Expressing Human G Protein-Coupled Receptor 73 (GPR73)

To further analyze the impact of the phoA mutant promoter phac on expression and yield of the EG-VEGF receptor (GPR73), shake flask inductions were carried out using the plasmids pST239.EGVEGFr1.Flag.H8.1270 (phoA promoter) and pR1FHr (phac promoter). Both plasmids express the human G protein-coupled receptor 73 protein (hGPR73) (Lin, et al., 2002, *J. Biol. Chem.* 277:19276-19280) with an N-terminal leader sequence (MKHQHQQ, SEQ ID NO: 7) for efficient translation initiation and two C-terminal tags, Flag and octa-His. Plasmids were transformed into the *E. coli* strain 58F3 (W3110-fhuAΔ (tonAΔ) phoAΔE15 lonΔ galE rpoHts (htpRts) ΔclpP lacIq ΔompTΔ(nmpc-fepE) ΔslyD). Selected transformant picks were inoculated into 5 mL Luria-Bertani medium supplemented with carbenicillin (50 µg/mL) and grown at 30° C. on a culture wheel for approximately 14-16 hours. The optical density (OD$_{600}$) of the overnight culture with pST239.EGVEGFr1.Flag.H8.1270 containing the phoA promoter was 0.84, while the culture with pR1FHr containing the phac promoter was 3.19.

A 1 $OD_{600}$-mL sample from the overnight LB inoculum was collected. Each culture was then diluted (1:100) into C.R.A.P. phosphate-limiting media (Simmons et al., 2002, *J. Immunol. Methods*, 263:133-147), with 50 µg/mL of carbenicillin. All cultures were grown at 25° C. in a two liter baffled flask with the 500 mL final induction volume on a shaker with approximately 200 rpm speed. A 1 $OD_{600}$-mL sample was collected at 14, 15, 16, 17, and 24 hours post inoculation into the C.R.A.P. media for the pST239.EGVEGFr1.Flag.H8.1270 (phoA) culture. For the cultures expressing pR1FHr (phac), 1 mM IPTG was added at 14 and 15 hours post inoculation into the C.R.A.P. media. Respective $OD_{600}$ of the cultures at IPTG inductions were 2.37 (14 hour) and 3.21 (15 hour).

A 1 $OD_{600}$-mL sample was collected before IPTG addition, two, three, and ten hours post IPTG addition for the 14th hour induction. For the $15^{th}$ hour induction, a 1 $OD_{600}$-mL sample was collected before IPTG addition, and two and nine hours post IPTG addition.

Reduced whole cell lysates of the 1 $OD_{600}$-mL samples were prepared as described above for RA1c in Example 4. Following SDS sample preparation, 8 µL of the reduced whole cell lysates of all samples were loaded onto a 10 well, 1.0 mm NOVEX manufactured 16% Tris-Glycine SDS-PAGE and electrophoresed at around 120 volts for about 1.5 hours. The resulting gels were then used for Western blot analysis as described above for RA1c in Example 3.

The anti-His Western blot results for expression of GPR73 from the phoA promoter and from the phac promoter are shown in FIG. 13. Human GPR73 was expressed from the phoA promoter (pST239.EGVEGFr1.Flag.H8.1270) prior to induction (middle lane), indicating leakage of the phoA promoter when phosphate was not limiting. In contrast, no hGPR73 expression was detected with the tightly controlled phac promoter (right lane). As noted for RA1c expression in Example 3, basal level expression of the multi-transmembrane protein with the phoA promoter was toxic to the cell, causing poor growth in LB, and resulting in overall low cell density. The $OD_{600}$ reading of the overnight LB inoculums improved from 0.84 in pST239.EGVEGFr1.Flag.H8.1270 (phoA promoter) to 3.19 in pR1FHr (phac promoter), indicating healthier cells and growth of cells containing the phac promoter.

The time course of expression results for GPR73 from the phoA promoter is shown in FIG. 14. Expression was detected with a dimer band present at the $15^{th}$ hour with an $OD_{600}$ reading of 3.14, and the protein had completely disappeared by the $24^{th}$ hour. In contrast, the cells continue to grow as noted by the increasing $OD_{600}$ reading. This continual growth is an example of the variable results observed with the expression of some multi-transmembrane proteins using the phoA promoter, and suggests that some of the cells have down-regulated the expression by some means. Regardless, the expression pattern of GPR73 was similar to that seen in Example 3 for RA1c, or for other multi-transmembrane proteins. Expression peaked at the $16^{th}$ hour and the corresponding $OD_{600}$ was 3.46.

Optimally the phac promoter should be completely shut off until the time of induction by phosphate depletion in the C.R.A.P. media. IPTG induced expression of GPR73 is shown in FIG. 15. No detectable expression of hGPR73 was seen without IPTG induction, suggesting the tightness of the phac promoter. Maximum protein production was reached within two hours post IPTG addition. A similar expression pattern was observed with the monomeric and dimeric bands appearing early, while the smear came late in the induction. Upon induction, cells undergo stress and stop growing, and eventually the cell density drops. The culture induced at the 15th hour showed better expression than that induced at the 14th hour. Maximum production was achieved two hours post IPTG induction (15th hour) at hour 17, and the OD600 was 2.41.

The overall expression of hGPR73 with phoA and phac promoters is compared in FIG. 16. The best expression results from each promoter are presented on the same blot for direct comparison. No detectable hGPR73 expression was seen with the phoA promoter (middle lane) when compared to the phac promoter (right lane), except with a longer film exposure. It is clear that the two-hour induction of the hGPR73 with the phac promoter at the $15^{th}$ hour yielded much higher protein expression. Expression results using the phoA promoter also tended to be variable, whereas expression results using the phac promoter were relatively constant.

Example 6 phoA vs. tphac for the Membrane Protein MS4A4A

To analyze the impact of the mutant phoA promoter, tphac, for expression and yield of MS4A family polypeptides, shake flask inductions were carried out in using the plasmids pMS4A4A.8His.32 with the phoA promoter and pMS4A4ArT with the tphac promoter. Both plasmids express human immunoglobulin E receptor-like protein, (hIGERB) (hMS4A4A) (Liang, et al., 2001, *Genomics* 72:119-127) with an N-terminal leader, MKHQHQQ, for efficient translation initiation and a C-terminal 8×-his tag. Plasmids were transformed into the *E. coli* strain 58F3 (W3110-fhuAΔ(tonAΔ) phoAΔE15 IonΔ galE rpoHts(htpRts) ΔclpP lacIq ΔompTΔ (nmpc-fepE) ΔslyD) and selected transformant picks were inoculated into 5 mL Luria-Bertani medium supplemented with carbenicillin (50 µg/mL) and grown at 30° C. on a culture wheel for approximately 14-16 hours. The $OD_{600}$ of the culture with pMS4A4A.8His.32 (phoA) was 2.4 and the culture with pMS4A4ArT (tphac) was 2.5. A 1 $OD_{600}$-mL sample from the overnight LB inoculum was collected.

Each culture was then diluted (1:100) into C.R.A.P. phosphate-limiting media (Simmons et al., 2002, Supra) with 50 µg/mL of carbenicillin. All cultures were grown at 30° C. in two liter baffled flasks with a 500 mL final induction volume on a shaker at approximately 200 rpm speed. A 1 $OD_{600}$-mL sample was collected at 10, 11, 12, 14, and 15 hours post inoculation into the C.R.A.P. media for the pMS4A4A.8His.32 culture (phoA). For the cultures expressing pMS4A4ArT (tphac), 1 mM IPTG was added at 10 and 10.5 hours post inoculation into the C.R.A.P. media. Respective $OD_{600}$ of the culture at IPTG inductions were 2.1 and 2.6.

A 1 $OD_{600}$-mL sample was collected before IPTG addition, one, two, four, and five hours post IPTG addition for the pMS4A4ArT culture (10th hour IPTG addition). For pMS4A4ArT 10.5th hour IPTG addition culture, a 1 $OD_{600}$-mL sample was collected before IPTG addition, one, and four hours post IPTG addition.

Reduced whole cell lysates of the 1 $OD_{600}$-mL samples were prepared as described for Example 4. Following SDS sample preparation, 8 µL of pMS4A4A.8His.32 (phoA) and pMS4A4ArT (tphac) samples were loaded onto a 10 well, 1.0 mm NOVEX manufactured 16% Tris-Glycine SDS-PAGE and electrophoresed at around 120 volts for about 1.5 hours. Induced samples in the C.R.A.P media were loaded onto a 15 well gel. The resulting gels were then used for Western blot analysis as described for Example 3.

The anti-His Western blot results showing expression of MS4A4A the pMS4A4A.8His.32 (phoA) and pMS4A4ArT (tphac) vectors in liquid LB media are shown in FIG. 17. Human immunoglobulin E receptor-like protein (hIGERB) was expressed from the phoA promoter (pMS4A4A.8His.32) without induction, indicating leakage of the phoA promoter when phosphate is not limiting. In contrast, no protein expression was detected prior to induction of hMS4A4A with the tightly controlled tphac promoter. The $OD_{600}$ reading of the overnight LB inoculums improved slightly from 2.4 in pMS4A4A.8His.32 (phoA) to 2.5 in pMS4A4ArT (tphac).

The time course of MS4A4A expression from the phoA promoter are shown in FIG. 18. Expression was detected at the 11th hour with an $OD_{600}$ reading of 2.24. The protein was relatively stable over time; however, protein expression did not improve over time. Maximum production was reached within one hour at the 11th hour. Cell density dropped thereafter.

The results of IPTG induced MS4A4A expression from pMS4A4ArT (tphac) cultures are shown in FIG. 19. No detectable protein expression of hIGERB was seen without IPTG addition, suggesting the tightness of the tphac promoter. Expression was detected within an hour after IPTG induction. The culture induced at the 10th hour with OD600 of 2.1 showed slightly better expression than that induced at the 10.5th hour with OD600 of 2.6. Maximum production was achieved two hours post IPTG induction, 12th hour (IPTG added at 10th hour), and the OD600 was 2.36.

Overall expression of hMS4A4A is compared for the phoA promoter and tphac promoter in FIG. 20. The best expression results from the phoA and tphac promoter are presented on the same blot for direct comparison. The 12th hour sample of the IPTG induced pMS4A4ArT (IPTG added at the 10th hour) showed significant improvement in expression over the 11th hour sample of pMS4A4A.8His.32 with the phoA promoter. The $OD_{600}$ of the tphac driven culture was 2.19, while the $OD_{600}$ for the peak expression with the phoA promoter was 2.24.

Example 7

Increasing CD20 Expression with the trpLE Leader

The trp LE sequence has been used for many years as an N-terminal fusion partner to express particularly problematic proteins that accumulate poorly (see, for example, Yansura, 1990, *Methods in Enzymology*, Vol. 185:161-166, Academic Press Inc., San Diego, Calif.). The trpLE proteins generally represent in-frame deletions of the trp leader at one end, and distal parts of the trpE gene. Two versions, ΔtrpLE1417 and ΔtrpLE1413, have been reported (see, for example, Bertrand et al., 1976, *J. Mol. Biol.* 103:319-337 and Miozzari et al., 1978, *J. Bacteriol.* 133:1457-1466). ΔtrpLE1413, has been used to construct vectors for expression of several human proteins (see, for example, U.S. Pat. No. 5,888,808). However, attempts to express the membrane-spanning protein hepatitis B surface antigen with a similar vector, pHS94, were reported with negative results (see, for example, U.S. Pat. Nos. 4,803,164 and 4,741,901).

High-level expression of proteins fused to the trpLE is generally attributed to the strong trp promoter, strong translation initiation region that includes the first several codons of the trp leader, and the resulting push of heterologous proteins into proteolytically stable refractile bodies. To determine if a trpLE leader could push multi-membrane-spanning proteins into refractile bodies and/or otherwise increase expression and yield of heterologous multi-spanning membrane proteins in *E. coli*, several constructs were made using two versions of the trpLE sequence leader, designated LE (SEQ ID NO: 25) and sLE (SEQ ID NO: 26). These constructs were made with the more-tightly controlled phoA and phac/tphac promoters, as described for the Examples above.

The longer of the two leaders, LE, contained just the first nine amino acids ((M)KAIFVLKGS, SEQ ID NO: 27) of the *E. coli* trp E protein, described, for example in the expression vector pNCV (ΔtrpLE1413) (Maniatis et al., In *Molecular Cloning: A Laboratory Manual*, p 426, Cold Spring Harbor Laboratory, Cold Spring Harbor, N.Y., 1982.), followed by amino acids 339-408 of the trpE polypeptide (SEQ ID NO: 25), as shown in FIG. 22. A smaller trpLE sequence leader (sLE) containing the same first nine amino acids of the trp leader, followed by a sequence of discontinuous amino acids from the trpE polypeptide (SEQ ID NO: 26), is also shown in FIG. 22. These two trpLE leaders behaved similarly in terms of membrane insertion, although the expression level was approximately two fold higher with the longer LE leader.

Cloning & Expression of LE CD20

A mutant CD20 having Cys111 and Cys220 each replaced with serine and having Cys81 replaced with alanine was sub-cloned, using standard molecular biology techniques (Ausubel et al. (eds.), 2003, *Current Protocols in Molecular Biology*, 4 Vols., John Wiley & Sons), into a pBR322-derived plasmid containing the beta-lactamase gene and tRNA genes for three rare *E. coli* codons (argU, glyT, and pro2). The 79 amino acid trpLE spacer sequence (SEQ ID NO: 25) and a GS linker sequence were added at the N-terminus A thrombin cleavage recognition site was added after the ninth amino acid of CD20 to cleave the trpLE leader, and after the 236th amino acid of CD20 to cleave the intracellular hydrophilic tail. To encode a tag sequence at the C-terminus, octa-His (SEQ ID NO: 8) was added to aid in detection and purification of the expressed protein. The resulting plasmid was designated pLEfGKiSArT. Gene transcription was under the control of the phoA promoter, and expression was induced by limiting phosphate in *E. coli* strain 58F3, as described for Example 4 above. A saturated LB carbenicillin culture was diluted into C.R.A.P. phosphate limiting media (Simmons et al., 2002, *J. Immunol. Methods*, 263:133-147). The culture was then grown at 30° C. for 24 hours.

For expression analysis, reduced whole cell lysates of 1 $OD_{600}$-mL samples were prepared as follows:

1 $OD_{600}$-mL samples were centrifuged in a microfuge tube.

Each pellet was resuspended in 70 μL TE (10 mM Tris pH 7.6, 1 mM EDTA).

To reduce disulfide bonds, 10 μL of 1M dithiothreitol (Sigma D-5545) was added to each sample.

20 μL of 20% SDS was added to each sample.

The samples were vortexed, heated at 90° C. for 5 minutes and vortexed again. After the samples had cooled to room temperature, 100 μL 2× NOVEX SDS sample buffer was added. The samples were then heated for 5 minutes at 90° C., vortexed well, and allowed to cool to room temperature. A final 5-minute centrifugation was then performed, and the supernatants were transferred to clean tubes.

Following SDS sample preparation, 16 μL induction samples were loaded onto a 10 well, 1.0 mm NOVEX 16% Tris-Glycine SDS-PAGE and electrophoresed at approximately 120 volts for about 1.5 hours. The resulting gel was stained with Coomassie blue having 10% acetic acid added. For Western blot analysis, 1 μL of the whole cell lysate was loaded and the resulting gel was electroblotted onto a nitrocellulose membrane (NOVEX) in 1× Tris-glycine Buffer (Invitrogen, CA), 0.01% SDS, 5% methanol. Membranes were then blocked using a solution of 1× NET (150 mM NaCl, 5 mM EDTA, 50 mM Tris, pH 7.4, 0.05% Triton X-100) and 0.5% gelatin for approximately 30 minutes to one hour on a rocker at room temperature. Following the blocking step, membranes were placed in a solution of 1×NET, 0.5% gelatin, containing anti-His antibody (anti-His6 Peroxidase conjugated mouse monoclonal antibody from Roche Diagnostics) for anti-His Western blot analysis. The anti-His antibody dilution was 1:5,000 and the membranes were washed a minimum of 3×10 minutes in 1×NET and then 1×15 minutes in TBS (20 mM Tris pH 7.5, 500 mM NaCl). The protein bands bound by the anti-His antibody were visualized using Amersham Pharmacia Biotech ECL detection and exposing the membrane to X-Ray film.

FIG. 23 shows the construct diagram for LE.CD20 and CD20 expression results from LE.CD20 compared with expression from the PhoA promoter without the trpLE leader, but under control of the phoA promoter with the leader sequence MKHQHQQ (SEQ ID NO: 7), as described for Example 1. Expression and production of CD20 protein in *E. coli* cells, using the trpLE was greatly enhanced to a level that was detectable on a Coomassie blue-stained gel. Western blot analysis showed approximately ten times better expression yield of CD20 with the trpLE leader than without the trpLE leader (data not shown). The estimated expression level was about 30 milligrams of trpLE fused CD20 per 1 liter of culture.

LE CD20 Membrane Protein Extraction

To analyze the solubility of the trpLE fusion CD20, a cell pellet was resuspended using a Polytron (Brinkmann, Westbury, N.Y.) in 10 mL of native lysis buffer (20 mM Tris pH 7.5, 300 mM NaCl) per each 1 g of paste, lysed by cell disruption using a microfluidizer (Microfluidics Corp, Newton, Mass.), and centrifuged at 391,000×g for 1 hour using the ultracentrifugation rotor TLA-100.3 (Beckman, Fullerton, Calif.). The supernatant containing soluble proteins (Sup 1) was separated from the pellet containing membrane proteins and insoluble proteins (pellet 1). Pellet 1 was then resuspended using a Polytron in native lysis buffer with non-denaturing neutral detergent, 1% Fos-Choline 12, and extracted overnight at 4° C. The following day, the sample was again ultracentrifugated, and the supernatant containing membrane-bound proteins in micellular form (Sup 2) was isolated from insoluble proteins (pellet 2). The pellets and supernatants were re-suspended in reducing SDS loading buffer to equal volumes and analyzed by SDS-PAGE and immunoblot on nitrocellulose membrane probed with horseradish peroxidase-conjugated anti-His antibodies (Roche Applied Science, Indianapolis, Ind.).

Results demonstrate near complete trpLE.CD20 extraction from membranes was obtained, as shown in both the Coomassie blue-stained gel and immunoblot (FIG. 24).

LE CD20 Density Gradient Centrifugation

A discontinuous sucrose gradient was generated by layering 1.9 M and 1.4 M sucrose solutions buffered with 150 mM NaCl and 20 mM HEPES, pH 7.2, in centrifuge tubes. Cells expressing the LE CD20 protein were lysed in native lysis buffer. The membrane and insoluble fraction was isolated by ultracentrifugation at 391,000×g (85K rpm) for 1 hour using the ultracentrifugation rotor TLA100.3 (Beckman, Fullerton, Calif.). The supernatant was discarded and the pellet was resuspended in 1.9 M sucrose solution. A 100 μl aliquot of the resuspension was mixed again with 0.9 mL of 1.9 M sucrose solution. This mixture was then placed at the bottom of a centrifuge tube and 1 mL of the 1.4 M sucrose solution was layered above. Sample was loaded into an SWTi55 rotor and spun for 1 hour at 128,356×g (32.5K rpm). The fractionated sample was then carefully unloaded in 200 μL aliquots from the top of the tube and each fraction (10 top, 1 bottom) was analyzed by SDS-PAGE, transferred to a nitrocellulose membrane, and probed with horseradish peroxidase conjugated anti-His antibody. The Western blot analysis demonstrated the trp LE fusion CD20 polypeptide is found in the membrane layer positioned at the interface of the 1.4 M and 1.9 M sucrose solutions (fractions 5 and 6), with most of the polypeptide in fraction 5 (data not shown), indicating that most of the trpLE fusion CD20 polypeptide appears to be inserted in the *E. coli* membrane.

LE CD20 Thrombin Cleavage

Thrombin with 1 mM calcium chloride was added to the 1% Fos-Choline 12 soluble membrane extracts from the solubility analysis in 1:1000 dilution and left at room temperature for overnight. Reduced SDS prepared samples were analyzed by SDS-PAGE. The Coomassie blue-stained gel showed good cleavage of the two thrombin cleavage sites engineered on the fusion protein, resulting in three protein bands, including a truncated CD20 transmembrane domain (26 kDa), trpLE (11 kDa), and the hydrophilic C-terminal tail of CD20 (8 kDa) (data not shown). The N-termini of the peptides from each of the three bands was sequenced to confirm identity.

Example 8

Increasing RA1c Expression with the trpLE Leader

Cloning & Expression of LE RA1c

DNA encoding RA1c was sub-cloned, using standard molecular biology techniques as described above, into a pBR322-derived plasmid containing the beta-lactamase gene and tRNA genes for three rare *E. coli* codons (argU, glyT, and pro2). The trpLE leader followed by a flag tag (DYKD-DDDK, SEQ ID NO: 32) and a thrombin recognition site (thrX) (LVPRGS, SEQ ID NO: 31) were added at the N-terminus of RA1c to ensure high translation initiation, detection, and cleavage, respectively. Ten Histidine residues were added at the C-terminus to aid in detection and purification of the expressed protein. The resulting plasmid was designated pLEfRA1CnFcHrT. Gene transcription was under the control of the tphac promoter, and expression was induced by limiting phosphate and the addition of 1 mM IPTG at around cell density of 2 to 3 $OD_{600}$, as described for the Examples above. A saturated LB carbenicillin culture was diluted into C.R.A.P. phosphate limiting media (Simmons et al., 2002, *J. Immunol. Methods*, 263:133-147). The culture was then grown at 30° C. for 6 hours post IPTG addition.

For expression analysis, reduced whole cell lysates of 1 $OD_{600}$-mL samples were prepared as described previously for Example 7. Following SDS sample preparation, 5 μL induction samples were loaded onto a 10 well, 1.0 mm NOVEX 16% Tris-Glycine SDS-PAGE and electrophoresed at approximately 120 volts for about 1.5 hours. For Western blot analysis, the resulting gel was electroblotted onto a nitrocellulose membrane (NOVEX) in 1× Tris-glycine Buffer (Invitrogen, CA), 0.01% SDS, 5% Methanol). Membranes were then blocked using a solution of 1× NET (150 mM NaCl, 5 mM EDTA, 50 mM Tris, pH 7.4, 0.05% Triton X-100) and 0.5% gelatin for approximately 30 minutes to one hour on a rocker at room temperature. Following the blocking step, membranes were placed in a solution of 1×NET, 0.5% gelatin, and anti-His antibody (Anti-His6 Peroxidase conjugated mouse monoclonal antibody from Roche Diagnostics) for anti-His Western blot analysis. The anti-His antibody dilution was 1:5,000 and the membranes were washed a minimum of 3×10 minutes in 1×NET followed by 1×15 minutes in TBS (20 mM Tris pH 7.5, 500 mM NaCl). Protein bands bound by the anti-His antibody were visualized using Amersham Pharmacia Biotech ECL detection and exposing the membrane to X-Ray film.

FIG. 25 shows the construct diagram for LE.RA1c (47.6 kDa) and compares RA1c expression results from LE.RA1c with that of RA1c expressed from a construct that lacks the trpLE leader, and contains the leader sequence MKHQHQQ (SEQ ID NO: 7), both under control of the tPhac promoter as described for Example 4. Western blot analysis using anti-HIS antibody demonstrated a greatly improved expression level for LE.RA1c containing the LE leader sequence over that of RAIc without the trpLE leader (See FIG. 25).

RA1c Membrane Protein Extraction

To analyze the solubility of the trpLE fusion RA1c, a cell pellet was resuspended using a Polytron (Brinkmann, Westbury, N.Y.) in 10 mL of native lysis buffer (20 mM Tris pH 7.5, 300 mM NaCl) per each 1 g of paste, and lysed by cell disruption using a microfluidizer (Microfluidics Corp, Newton, Mass.), and centrifuged at 391,000×g for 1 hour using the ultracentrifugation rotor TLA-100.3 (Beckman, Fullerton, Calif.). The supernatant containing soluble proteins (sup 1) was separated from the pellet containing membrane proteins and insoluble proteins (pellet 1). Pellet 1 was then resuspended using a Polytron in native lysis buffer with non-denaturing detergent, 1% Fos-Choline 12 and extracted overnight at 4° C. The following day, the sample was again ultracentrifuged, and the supernatant containing the membrane bound proteins in micellular form (sup 2) was isolated from insoluble proteins (pellet 2). Pellets and supernatants were re-suspended in reducing SDS loading buffer to equal volumes and analyzed by SDS-PAGE and immunoblot on nitrocellulose membrane probed with horseradish peroxidase-conjugated anti-His antibodies (Roche Applied Science, Indianapolis, Ind.). As shown in FIG. 26, near complete LE.RA1c extraction from the membrane was observed in both the Coomassie blue-stained gel and the immunoblot. The yield of RA1c protein was sufficient to view in the Coomassie-blue stained gel after 1% Fos-Choline 12 extraction.

LE RA1c Density Gradient Centrifugation

LE RA1c was subjected to density gradient centrifugation using the method described above for CD20 in Example 7. Briefly, a discontinuous sucrose gradient was generated by layering 1.9 M and 1.4 M sucrose solutions as described above. In the same manner as described for Example 7, the results of Western blot analysis demonstrated most of the LE.RAc polypeptide appeared to be inserted in the $E.\ coli$ membrane (data not shown).

LE RA1c Protein Isolation

To isolate the LE.RA1c protein, the 1% Fos-Choline 12 soluble membrane extract described above in the solubility analysis was loaded onto a Ni-NTA PhyTip column (Phynexus, San Jose, Calif.), washed with 50 mM Imidazole and 0.5% Fos-Choline 12 in native lysis buffer, and eluted with 250 mM Imidazole and 0.75% Fos-Choline 12 in native lysis buffer. The eluate fractions were re-suspended in reducing SDS loading buffer and analyzed by SDS-PAGE. The SDS PAGE gel showed purified LE.RA1c at a molecular weight of 47.6 kDa (data not shown).

It is known that G protein-coupled receptors oligomerize, for example, dimerize, even in the presence of reducing agent and SDS (Bouvier, 2001, $Nature\ Reviews\ Neuroscience$, 2: 274-286). Upper bands seen in the gel appear to be such dimers and oligomers of RA1c, judging by the molecular weights (data not shown). Purified protein was confirmed as LE.RA1c by N-terminal protein amino acid sequencing.

Approximately 10 milligrams of trpLE RA1c can be isolated from the whole cell extract from 1 liter of shake flask culture, as calculated from the intensity of the protein band after Coomassie blue-staining.

LE RA1c Thrombin Cleavage

To isolate the RA1c polypeptide, thrombin with 1 mM calcium chloride was added to the purified RA1c eluate at a 1:1000 dilution and left at room temperature overnight to effect thrombin enzymatic activity. Samples were reduced, prepared, and analyzed by SDS-PAGE. The resulting Coomassie blue-stained gel showed good cleavage of the fusion protein at the inserted thrombin cleavage sites, producing two protein bands that included the truncated RA1c fusion (37 kDa) and the trpLE with flag tag (10.6 kDa) (data not shown). The identity of the cleaved polypeptide bands was confirmed by N-terminal sequencing.

Example 9

Increased Expression of GPR 73 with the trp LE Leader

Cloning & Expression of LE Human G Protein-Coupled Receptor 73(hGPR 73)

DNA encoding human G protein-coupled Receptor 73 (GPR 73) was sub-cloned, using standard molecular biology techniques (Ausubel et al. (eds.), 2003, $Current\ Protocols\ in\ Molecular\ Biology$, 4 Vols., John Wiley & Sons), into a pBR322-derived plasmid containing the Beta-lactamase gene and tRNA genes for three rare $E.\ coli$ codons (argU, glyT, and pro2). As shown in FIG. 25, the trpLE leader followed by a flag tag (DYKDDDDK, SEQ ID NO: 32) and a thrombin recognition site (ThrX) (LVPRGS, SEQ ID NO: 31) were added at the N-terminus of GPR73 to ensure high translation initiation, detection, and cleavage, respectively. An octa-His tag (SEQ ID NO: 8) was added at the C-terminus to aid in detection and purification of the expressed protein. The resulting plasmid was designated pLEfR1nFcHrT. Gene transcription was under the control of the tphac promoter, as described above for Example 8, and expression was induced by limiting phosphate and the addition of 1 mM IPTG at a cell density of about 2 to 3 $OD_{600}$. A saturated LB carbenicillin culture was diluted into C.R.A.P. phosphate limiting media (Simmons et al., 2002, $J.\ Immunol.\ Methods$, 263:133-147). The culture was then grown at 30° C. for 6 hours post IPTG addition.

For expression analysis, reduced whole cell lysates of the 1 $OD_{600}$-mL samples were prepared as described above for Example 7. SDS induction samples of 5 µL were loaded onto a 10 well, 1.0 mm NOVEX 16% Tris-Glycine SDS-PAGE and electrophoresed at approximately 120 volts for about 1.5 hours. For Western blot analysis, the resulting gel was electroblotted onto a nitrocellulose membrane (NOVEX) in 1× Transfer Buffer (Invitrogen, CA), 0.01% SDS, 5% methanol. Membranes were then blocked using a solution of 1×NET (150 mM NaCl, 5 mM EDTA, 50 mM Tris, pH 7.4, 0.05% Triton X-100) and 0.5% gelatin for approximately 30 minutes to one hour on a rocker at room temperature. Following the blocking step, membranes were placed in a solution of 1×NET, 0.5% gelatin, and anti-His antibody (Anti-His6 Peroxidase conjugated mouse monoclonal antibody from Roche Diagnostics) for anti-His Western blot analysis. The anti-His antibody dilution was 1:5,000 and the membranes were washed a minimum of 3×10 minutes in 1×NET and then 1×15 minutes in TBS (20 mM Tris pH 7.5, 500 mM NaCl). The protein bands bound by the anti-His antibody were visualized using Amersham Pharmacia Biotech ECL detection and exposing the membrane to X-Ray film.

FIG. 25 shows the construct diagram and expression results compared to that of the GPR73 without the trpLE leader. The Western blot showed greatly improved expression and yield of LE.GPR73 level over that without the trpLE leader.

LE Human G Protein-Coupled Receptor 73 Membrane Protein Extraction

To analyze the solubility of the trpLE fusion GPR73, the protein was extracted from cellular membranes and analyzed as described above for similar analysis of LE.CD20 and LE.RA1c proteins in Examples 7 and 8. Membrane proteins (pellet 1) were separated from the supernatant containing soluble proteins (sup 1). Pellet 1 was then extracted with Fos-choline 12 and the membrane proteins in micelles (sup 2) were separated from insoluble proteins (pellet 2).

Pellets and supernatants were re-suspended in reducing SDS loading buffer to equal volumes and analyzed by SDS-PAGE and immunoblot on nitrocellulose membrane probed with horseradish peroxidase-conjugated anti-His antibodies (Roche Applied Science, Indianapolis, Ind.). Near complete extraction of the GPR73 protein from the *E. coli* cell membrane was observed, as shown in the immunoblot, FIG. 27.

LE Human G Protein-Coupled Receptor 73 Density Gradient Centrifugation

A discontinuous sucrose gradient was generated by layering 1.9 M and 1.4 M sucrose solutions buffered with 150 mM NaCl and 20 mM HEPES, pH 7.2, in centrifuge tubes, and utilized to separate the *E. coli* membrane fraction, as described above for Examples 7 and 8. Cells expressing the LE.GPR73 protein were lysed in native lysis buffer. The membrane and insoluble fraction was isolated by ultracentrifugation at 391,000×g for 1 hour using the ultracentrifugation rotor TLA100.3 (Beckman, Fullerton, Calif.). The supernatant was discarded and the pellet was resuspended in 1.9 M sucrose solution. A 100 µl aliquot of the resuspension was mixed again with 0.9 mL of 1.9 M sucrose solution. This mixture was then placed at the bottom of a centrifuge tube and 1 mL of the 1.4 M solution layered above. Sample was loaded into an SW55 rotor and spun for 1 hour at 128,356×g. The fractionated samples were then carefully unloaded in 200 µL aliquots from the top of the tube and analyzed by SDS-PAGE, transferred to a nitrocellulose membrane, and probed with horseradish peroxidase conjugated anti-His antibody. Results demonstrated that most of the trpLE fusion GPR73 protein appeared to be inserted in the *E. coli* membrane (data not shown).

LE Human G Protein-Coupled Receptor 73 Protein Isolation

To isolate the LE.GPR73 protein, a portion of the 1% Fos-Choline 12 soluble membrane extract from the solubility analysis described above was loaded onto a Ni-NTA PhyTip column (Phynexus, Calif.), washed with 50 mM Imidazole and 0.5% Fos-Choline 12 in native lysis buffer, and eluted with 250 mM Imidazole and 0.75% Fos-Choline 12 in native lysis buffer. Samples of the eluate fractions were re-suspended in reducing SDS loading buffer and analyzed by SDS-PAGE. The resulting gel showed the purified GPR73 protein at its molecular weight of 56.5 kDa (data not shown). The identity of the purified protein was confirmed by N-terminal sequencing. The protein yield calculations indicated that approximately 2 to 3 milligrams of the trpLE GPR73 could be isolated from the whole cell extract of 1 liter of shake flask culture.

LE Human G Protein-Coupled Receptor 73 Thrombin Cleavage

The GPR73 protein was cleaved from the fusion protein at the inserted thrombin cleavage sites. Thrombin with 1 mM calcium chloride was added to the purified GPR73 eluate at a 1:1000 dilution and left at room temperature overnight to effect enzymatic cleavage. A Sample of the cleaved protein was reduced with SDS and analyzed by SDS-PAGE. The Coomassie-blue stained gel showed good cleavage of the fusion protein at the inserted sites, resulting in two protein bands, including the cleaved GPR73 (45.9 kDa) and the trpLE with the flag tag (10.6 kDa) (data not shown). The identity of the cleaved proteins was confirmed by N-terminal sequencing.

Example 10

Purification of Membrane Proteins

Purification of LE and sLE Tagged Human CD20:

To isolate the LE and sLE proteins produced in *E. coli* as described above in Examples 7, 8, and 9, membrane fractions were prepared by resuspending whole cells using a Polytron (Brinkmann, Westbury, N.Y.), in 1:10 wt/vol lysis buffer (20 mM Tris, pH 7.5, 300 mM NaCl and 1 mM EDTA). Cells were then lysed by cell disruption using a microfluidizer (Microfluidics Corp., Newton, Mass.) and the mixture was centrifuged at 12,000×g for 1 hour. The cell pellet (P1) was then resuspended in lysis buffer without EDTA, and in the presence or absence of beta-mercaptoethanol, using a Polytron. Dodecylphosphocholine (DDPC, FOS—CHOLINE® 12) was added to a concentration of 1% and the samples were passed though a microfluidizer one to three times. The solution was then centrifuged at 125,000×g for about 45 minutes to 1 hour. The supernatant was loaded onto a Ni-NTA SUPERFLOW™ (Qiagen Inc. Valencia, Calif.) column pre-equilibrated in buffer (20 mM Tris, pH 7.5, 250-300 mM NaCl and 5 mM DDPC or 0.1% n-dodecyl-N,N-dimethylamine-N-oxide (LDAO)). The column was washed with 10 CV of the same buffer with 50 mM imidazole and eluted with the same buffer with 250 to 300 mM imidazole. All purification steps through column loading were performed at 4° C.

Protein purified in the presence of reducing agent was isolated from the membranes only as monomer (data not shown). Protein isolated in the absence of reducing agent was present in both monomeric and disulfide-linked dimeric forms.

To convert dimeric protein into the monomeric form, CD20 was reduced by the addition of beta-mercaptoethanol or DTT. The reducing agent was either removed by multiple rounds of dialysis against buffer containing 20 mM Tris pH 8.0, 300 mM NaCl, and detergent with no reducing agent present, or the reducing agent was neutralized by addition of an oxidized reducing agent such as oxidized DTT or oxidized glutathione.

The His-tag and the LE or sLE leader was cleaved from the protein by incubation with bovine thrombin. To isolate monomeric CD20 from any remaining dimer, leader (LE or sLE) and His-tags, the cleaved protein was loaded onto a Superdex 200 column (Amersham Biosciences, Piscataway, N.J.) pre-equilibrated in 20 mM Tris, pH 7.5, 300 mM NaCl, and 5 mM DDPC or 0.1% n-dodecyl-N,N-dimethylamine-N-oxide (LDAO) Fractions from the size exclusion column were collected and analyzed by gel chromatography to demonstrate location of the purified protein. The purified protein was used in binding assays described below.

Activity Assay by ELISA:

The functional integrity of expressed CD20 proteins was assessed by the ability of human CD20 polypeptides expressed with and without the LE and sLE sequences to bind the antibody rituximab. Rituximab recognizes only a folded conformation of human CD20 in which the native disulfide bond between cysteine residues 167 and 183 has been formed. An ELISA assay of human CD20 binding to rituximab was used to assay native refolding of CD20.

The purified CD20 protein was assayed by ELISA. 96 well plates were coated overnight at 4° C. with 100 μL of CD20 at 1 μg/mL in PBS with solubilizing detergent diluted to below its critical micelle concentration. Plates were then washed three times with PBS containing 0.05% TWEEN-20™ (PBST) and blocked for 45 minutes at room temperature with 200 μL of PBST containing 0.5% BSA (blocking and assay buffer). Plates were again washed three times with PBST and probed with the primary antibody. 150 μL of rituximab at 60 μg/mL in assay buffer was added to the appropriate wells and three fold serial dilutions were performed in the subsequent wells by taking 50 μL from the first well and mixing with 100 μL of assay buffer in the next and subsequent wells to a final concentration of approximately 2 ng/mL. After 90 minutes of incubation at room temperature, the plates were washed with PBST and bound rituximab was detected with 100 μL of horseradish peroxidase conjugate goat anti-human F(ab')2 (Jackson ImmunoResearch Laboratories Inc, West Grove, Pa.) diluted 1:2000 in assay buffer, washed six times with PBST and developed with 100 μL/well of TMB Microwell Peroxidase Substrate System (KPL, Gaithersburg, Md.) mixed according to the manufacturer's instructions. The reaction was halted by the addition of 100 μL/well of 1.0 M phosphoric acid and the absorbance measured at 450 nm using a plate reader.

FIG. 28 shows the results of the binding assay, comparing the response of rituximab binding to human CD20 expressed without the LE or sLE sequence to human CD20 expressed with the LE or sLE leader and isolated under various conditions. Each of the expressed human LE.CD20 and sLE.CD20 polypeptides demonstrated binding to the conformation-specific antibody, rituximab, similar to that of the control human CD20.

---

What is claimed is:

1. A method for expressing or producing a recombinant multiple-membrane-spanning 4-domain subfamily (MS4A) polypeptide in a bacterial host cell, comprising:
   (a) providing a nucleic acid comprising:
   (i) a polynucleotide encoding the MS4A polypeptide or a membrane-spanning fragment of the MS4A polypeptide;
   (ii) a phac promoter consisting of SEQ ID NO:15 or tphac promoter consisting of SEQ ID NO:16 operatively linked to the polynucleotide encoding the MS4A polypeptide of (i); and
   (iii) a polynucleotide encoding a translation initiation enhancer;
   (b) introducing the nucleic acid into the host cell; and
   (c) expressing the nucleic acid in the host cell to express and produce the MS4A polypeptide or the membrane-spanning fragment of the MS4A polypeptide.

2. The method of claim 1, wherein the MS4A polypeptide is selected from the group consisting of a CD20 polypeptide, a high-affinity IgE receptor beta chain polypeptide, a HTm4 polypeptide, a MS4A4A polypeptide, a MS4A7 polypeptide; a membrane-spanning fragment of a CD20 polypeptide, a membrane-spanning fragment of a high-affinity IgE receptor beta chain polypeptide, a membrane-spanning fragment of a HTm4 polypeptide, a membrane-spanning fragment of a MS4A4A polypeptide, and a membrane-spanning fragment of a MS4A7 polypeptide.

3. The method of claim 2, wherein the CD20 membrane-spanning polypeptide has an amino acid sequence having at least 80% sequence identity to SEQ ID NO: 1.

4. The method of claim 3, wherein the CD20 membrane-spanning polypeptide has an amino acid sequence comprising at least 90% sequence identity to SEQ ID NO: 1.

5. The method of claim 3, wherein the CD20 membrane-spanning polypeptide has an amino acid sequence comprising at least 95% sequence identity to SEQ ID NO: 1.

6. The method of claim 5, wherein the CD20 polypeptide has amino acid substitutions at residues corresponding to Cys81Ala, Cys111Ser, and Cys220Ser of SEQ ID NO:1.

7. The method of claim 5, wherein the CD20 polypeptide has an amino acid substitution at a residue corresponding to Cys111 of SEQ ID NO:1, corresponding to Cys220 of SEQ ID NO:1, or corresponding to both Cys111 and Cys220 of SEQ ID NO:1.

8. The method of claim 7, wherein the CD20 polypeptide consists of an amino acid substitution at a residue corresponding to Cys111Ser of SEQ ID NO:1, corresponding to Cys220Ser of SEQ ID NO:1, or corresponding to both Cys111Ser and Cys220Ser of SEQ ID NO:1.

9. The method of claim 2, wherein the nucleic acid encoding CD20 polypeptide comprises a the nucleotide sequence encoding amino acid sequence of SEQ ID NO:6, or the fragment of CD20 comprises residues K116 through N214 of SEQ ID NO: 1.

10. The method of claim 2, wherein the CD20 membrane-spanning polypeptide is encoded by a polynucleotide sequence encoding a polypeptide comprising an amino acid sequence having at least 90% sequence identity with SEQ ID NO:1, wherein one or more of residues corresponding to Cys81, Cys111, and Cys220 of SEQ ID NO:1 are substituted.

11. The method of claim 1, wherein the nucleic acid further comprises:
(a) at least one positive regulatory control element comprising a pho box; or
(b) at least one negative regulatory control element comprising a lac operator.

12. The method of claim 11, wherein the pho box positive control element comprises an *E. coli* pho box.

13. The method of claim 11, wherein the negative control element comprises a bacterial lac operator of an operator/repressor system.

14. The method of claim 13, wherein the negative control element comprises an *E. coli* lac operator.

15. The method of claim 11, wherein the nucleic acid further comprises a positive control element comprising a pho box and a negative control element comprising a lac operator.

16. The method of claim 1, wherein the nucleic acid further comprises one or more transcriptional terminators positioned to prevent read-through from the upstream phac promoter or tphac promoter.

17. The method of claim 16, wherein the transcriptional terminator comprises a lambda sequence:

AACGCTCGGTTGCCGCCGGGCGTTTTTTATT (SEQ ID NO:17)

or a His operon terminator.

18. The method of claim 1, wherein the phac or tphac promoter is induced by exposure of the host cell to a phosphate-limiting media, or by operatively linking the phac or tphac promoter to at least one heterologous regulatory control element to be induced by exposure of the host cell to a phosphate-limiting media.

19. The method of claim 1, wherein the phac or tphac promoter further comprises or is operatively linked to at least one heterologous regulatory control element to reduce basal activity.

20. The method of claim 1, wherein the translation initiation enhancer comprises a β-galactosidase translation initiation enhancer.

21. The method of claim 20, wherein the β-galactosidase translation initiation enhancer comprises the first 6 to about 12 codons of a β-galactosidase gene.

22. The method of claim 20, wherein the β-galactosidase translation initiation enhancer further comprises the first 6 to about 12 codons of a Protein A or glutathione-S-transferase gene.

23. The method of claim 20, wherein the β-galactosidase translation initiation enhancer comprises a nucleotide sequence

ATGGGCAGCAGCCATCATCATCATCATCAT. (SEQ ID NO: 34)

24. The method of claim 1, further comprising a nucleic acid sequence encoding an leader sequence positioned just prior (5') to the first codon of the encoded MS4A polypeptide.

25. The method of claim 24, wherein the leader sequence comprises the amino acid sequence MKHQHQQ (SEQ ID NO: 7).

26. The method of claim 1, wherein the translation initiation enhancer is positioned upstream of the nucleotide sequence encoding the MS4A polypeptide.

27. The method of claim 1, wherein the translation initiation enhancer sequence further comprises a polynucleotide sequence encoding a translation elongation spacer sequence.

28. The method of claim 27, wherein the polynucleotide sequence encoding the translation elongation spacer sequence further comprises at least a portion of a gene highly expressed in a bacterial cell.

29. The method of claim 28, wherein the polynucleotide sequence encoding the translation elongation spacer sequence comprises about 50 to about 120 codons of the highly expressed gene.

30. The method of claim 29, wherein the polynucleotide sequence encoding the translation elongation spacer sequence comprises about 50 to about 120 codons of the *E. coli* gene of the trp operon.

31. The method of claim 30, wherein the polynucleotide sequence encoding the translation elongation spacer sequence encodes SEQ ID NO:29.

32. The method of claim 1, further comprising a nucleic acid sequence encoding an expression tag.

33. The method of claim 32, wherein the expression tag is selected from a poly His tag, a HisGln tag, a biotin tag, an avidin tag, or a combination thereof.

34. The method of claim 1, wherein the nucleic acid further comprises a nucleic acid comprising one or more tRNA genes of a bacterial cell.

35. The method of claim 34, wherein the tRNA genes comprise argU, glyT, or pro2.

36. The method of claim 1, wherein the nucleic acid encoding the MS4A polypeptide or the membrane-spanning fragment of the MS4A polypeptide is contained in an expression construct.

37. The method of claim 36, wherein the expression construct is a vector, a phage or a recombinant phagemid particle.

38. The method of claim 37, wherein the vector is an expression vector or a cloning vector.

39. The method of claim 1, wherein the nucleic acid sequence further comprises a nucleic acid sequence encoding an expression tag.

40. The method of claim 39, wherein the expression tag comprises a poly His tag or HisGln tag.

41. The method of claim 1, wherein the nucleic acid sequence further comprises one or more tRNA genes of a bacterial cell.

42. The method of claim 41, wherein the tRNA genes is argU, glyT, or pro2.

43. The method of claim 1, further comprising isolating or purifying the expressed MS4A polypeptide or membrane-spanning fragment of the MS4A polypeptide.

44. The method of claim 43, wherein the host cell is mixed with a detergent and centrifuged, and the expressed MS4A polypeptide or membrane-spanning fragment of the MS4A polypeptide is isolated or purified from the resulting supernatant.

45. The method of claim 44, wherein the expressed MS4A polypeptide or membrane-spanning fragment of the MS4A polypeptide is isolated or purified by a protocol comprising a fractionation on an ion-exchange column; an affinity chromatography, an ethanol precipitation; a reverse phase HPLC; a chromatography on silica or on a cation-exchange resin; a chromato-focusing; an SDS-PAGE; an ammonium sulfate precipitation; a gel filtration column; a metal chelating column; a hydrophobic affinity resin; a ligand affinity isolation protocol using an appropriate ligand immobilized on a matrix; a sucrose density gradient centrifugation; or a combination thereof,
thereby purifying or isolating the expressed MS4A polypeptide or membrane-spanning fragment of the MS4A polypeptide.

46. The method of claim 45, wherein the affinity chromatography comprises use of an anti-His-Tag or an anti-MS4A polypeptide antibody; or the gel filtration comprises use of a SEPHADEX™ (crosslinked dextran), a G-75™ (crosslinked dextran bead); a Protein A SEPHAROSE™ (agarose beads) column; or a combination thereof.

47. The method of claim 46, wherein isolation or purification of a His-tagged polypeptide can be achieved by passing a solubilized detergent fraction over a metal chelating column or a column comprising immobilized anti-His antibodies.

48. The method of claim 1, further comprising:
(a) disrupting the host cell expressing the expressed MS4A polypeptide or membrane-spanning fragment of the MS4A polypeptide;
(b) separating soluble and insoluble fractions of the disrupted cells; and
(c) suspending the insoluble fraction in a detergent to solubilize the expressed MS4A polypeptide or membrane-spanning fragment of the MS4A polypeptide.

49. The method of claim 48, further comprising isolating or purifying the detergent comprising the suspended insoluble fraction.

50. The method of claim 49, further comprising isolating or purifying the expressed MS4A polypeptide or membrane-spanning fragment of the MS4A polypeptide from the detergent comprising the suspended insoluble fraction.

51. The method of claim 50, wherein the expressed MS4A polypeptide or membrane-spanning fragment of the MS4A polypeptide is isolated or purified by a protocol comprising a centrifugation step, a chromatography step, a gel filtration step and/or a precipitation step.

52. The method of claim 51, wherein the centrifugation step comprises a sucrose density gradient centrifugation.

53. The method of claim 51, wherein the chromatography step comprises a column chromatography, an affinity chromatography, a metal chelating chromatography, an HPLC, a cation exchange chromatography and/or a chromatofocusing.

54. The method of claim 48, wherein the detergent comprises a non-ionic or a zwitterionic detergent.

55. The method of claim 48, wherein the detergent comprises: (a) at least one zwittergent selected from the group consisting of 3-08™ (n-Octyl-N,N-dimethyl-3-ammonio-1-propanesulfonate), 3-10™ (n-Decyl-N,N-dimethyl-3-ammonio-1-propanesulfonate), 3-12™ (n-Dodecyl-N,N-dimethyl-3-ammonio-1-propanesulfonate), 3-16™ (n-Hexadecyl-N,N-dimethyl-3-ammonio-1-propanesulfonate), ASB-14™ (Tetradecanoylamidopropyl-dimethylammonio-propanesulfonate), ASB-16™ (Hexadedecanoylamidopropyl-dimethylammonio-propanesulfonate), ASBC80™ (4-n-Octylbenzoylamido-propyl-dimethylammonio Sulfobetaine) and PMAL-B 100™ (Poly(maleic anhydride-alt-1-tetradecene), 3-(dimethylamino)-1-propylamine derivative); (b) a derivative of phosphocholine; (c) a detergent selected from the group consisting of dodecyl phosphocholine (DDPC), decylmaltoside (DDM), decyl maltoside (DM), n-dodecyl-N,N-dimethylamine N-oxide (LADO), n-decyl-N,N-dimethylamine-N-oxide, 1,2-diheptanoyl-sn-glycero-3-phosphocholine (DHPC), 1,2-dilauroyl-sn-glycero-3-phosphocholine (DLPC), 2-methacryloyloxyethyl phosphorylcholine (MPC), 1-oleoyl-2-hydroxy-sn-glycero-3-[phospho-RAC-(1-glycerol)] (LOPC) and 1-palmitoyl-2-hydroxy-sn-glycero-3-[phospho-RAC-(1-glycerol)] (LLPG); (d) an nonyl phenoxylpolyethoxylethanol (NP40); or (e) a combination of any of the detergents of (a) to (d).

56. The method of claim 1, wherein the bacterial cell is a gram-negative bacteria.

57. The method of claim 1, wherein the bacterial cell is an *Escherichia* cell, a *Salmonella* cell, a *Shigella* cell, a *Serratia* cell, a *Klebsiella* cell, an *Enterobacter* cell, a *Bacillus* cell, a *Pseudomonas* cell or a *Proteus* cell.

58. The method of claim 57, wherein the bacterial cell is an *Escherichia coli* cell, a *Shigella dysentariae* cell or a *Klebsiella pneumoniae* cell.

* * * * *